(12) United States Patent
Hessen et al.

(10) Patent No.: US 7,390,861 B2
(45) Date of Patent: Jun. 24, 2008

(54) CATIONIC GROUP-3 CATALYST SYSTEM

(75) Inventors: Bart Hessen, Noordwijk (NL); Sergio De Araujo Bambirra, Groningen (NL)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/399,695

(22) PCT Filed: Sep. 20, 2001

(86) PCT No.: PCT/US01/29442

§ 371 (c)(1),
(2), (4) Date: Apr. 18, 2003

(87) PCT Pub. No.: WO02/32909

PCT Pub. Date: Apr. 25, 2002

(65) Prior Publication Data

US 2004/0033891 A1 Feb. 19, 2004

Related U.S. Application Data

(60) Provisional application No. 60/243,207, filed on Oct. 25, 2000, provisional application No. 60/241,652, filed on Oct. 19, 2000.

(51) Int. Cl.
*C07F 5/00* (2006.01)
*C08F 4/52* (2006.01)
*C07D 255/02* (2006.01)

(52) U.S. Cl. .................. 526/161; 526/160; 526/172; 502/117; 502/155; 502/162; 502/167; 534/15; 534/16

(58) Field of Classification Search ............ 502/117, 502/155, 162, 167; 526/161, 172, 160; 534/15, 534/16

See application file for complete search history.

(56) References Cited

U.S. PATENT DOCUMENTS

| | | | |
|---|---|---|---|
| 5,064,802 A | 11/1991 | Stevens et al. | |
| 5,312,881 A | 5/1994 | Marks et al. | |
| 5,318,935 A | 6/1994 | Canich et al. | |
| 5,455,317 A | 10/1995 | Marks et al. | |
| 5,464,906 A | 11/1995 | Patton et al. | |
| 5,563,219 A | 10/1996 | Yasuda et al. | |
| 5,707,913 A | 1/1998 | Schlund et al. | |
| 5,763,556 A | 6/1998 | Shaffer et al. | |
| 5,851,945 A | 12/1998 | Turner et al. | |
| 2003/0100441 A1* | 5/2003 | Ittel et al. | 502/103 |
| 2004/0024234 A1* | 2/2004 | Vaughan | 556/136 |

FOREIGN PATENT DOCUMENTS

| | | |
|---|---|---|
| EP | 0 765 888 | 8/1990 |
| WO | WO 96/13529 | 5/1996 |
| WO | WO 97/23493 | 7/1997 |
| WO | WO 97/42228 | 11/1997 |
| WO | WO 00/01663 | 1/2000 |
| WO | WO 00/01739 | * 1/2000 |

OTHER PUBLICATIONS

Booij, et al., "On the synthesis of monopentamethylcyclopentadienyl derivatives of yttrium, lanthanum, and cerium", J. Organomet. Chem., vol. 364, 1989, pp. 79-86.

Couglin, et al., "Iso-Specific Ziegler-Natta Polymerization of ά-Olefins with a Single-Component Organoyttrium Catalyst", J. Am. Chem. Soc., vol. 114, 1992, pp. 7606-7607.

Flassbeck, et a., "Synthesis of N-Phenolate-functionalized Macrocycles of 1,4,7-Triazacyclononane and of 1-Oxa-4,7-diazacyclononane and their Cordination Chemistry with Iron (III)", Z. Anorg. Allg. Chem., vol. 608, 1992, pp. 60-68.

Flassbeck, et al, "Coordination of 4,7-Bis (2-hydroxybenzyl)-1-oxa-4,7-diazacyclononane ($LH_2$) with Manganese (II) and -(III) and Zinc (II). Crystal Structure of $[LH]_2Zn_2(\mu-OH)]$ ($PF_6$ )-0.5$CH_3OH$", Inorg. Chem., 1992, vol. 31, pp. 21-26.

Hajela, et al., "Competitive Chain Transfer by β-Hydrogen and β-Methyl Elimination for the Model Ziegler-Natta Olefin Polymerization System $[Me_2Si(\eta^5-C_5Me_4)_2]Sc\{CH_2CH (CH_3)_2\}(PMe_3)^+$", Organometallics, vol. 13, 1994, pp. 1147-1154.

Hajela, et al., "Highly electron deficient Group 3 organometallic complexes based on the 1,4,7-trimethyl-1,4,7-triazacyclononane ligand system", J. Organomet. Chem., vol. 532, 1997, pp. 45-54.

Lee, et al., "Synthesis of Dialkylscandium Complexes Supported by β-Diketiminato Ligands and Activation with Tris(pentafluorophenyl)borane", Organometallics, vol. 18, 1999, pp. 2947-2949.

Male, et al., "Ansa-Linked Titanium Macrocycle-imido Complexes", New J. Chem., vol. 24, 2000, pp. 575-577.

Piers, et al., "ά "Agostic" Assistance in Ziegler-Natta Polymerization of Olefins. Deuterium Isotopic Perturbation of Stereochemistry Indicating Coordination of an ά C-H Bond in Chain Propagation", J. Am. Chem. Soc., vol. 112, 1990, pp. 9406-9407.

Qian, et al., "Synthesis and Structure of $Li[(C_5H_4)CH_2CH_2$ (TACN-$^iPr_2$)]. A Lithium Complex Supported by a Cp/TACN-$^iPr_2$ Ligand", Organometallics, vol. 19, 2000, pp. 2805-2808.

Ray, et al., "Structure and Physical Properties of Trigonal Monopyramidal Iron (II), Cobalt (II), Nickel (II), and Zinc (II) Complexes", Inorg. Chem., vol. 37, 1998, pp. 1527-1532.

(Continued)

Primary Examiner—Roberto Rábago

(57) ABSTRACT

A cationic Group 3 or Lanthanide metal complex for coordination polymerization of olefins is disclosed. The precursor metal complex is stabilized by an anionic multidentate ancillary ligand and two monoanionic ligands. The ancillary ligand and the transition metal form a metallocycle having at least five primary atoms, counting any π-bound cyclopentadienyl group in the metallocycle as two primary atoms. Olefin polymerization is exemplified.

30 Claims, No Drawings

OTHER PUBLICATIONS

Robson, et al., "An Unprecedented Coordination Mode for Hemilabile Pendant-arm 1,4,7-triazacyclononanes and the Synthesis of Cationic Organoaluminium Complexes", Chem. Commun., 2000, p. 1269, 1270.

Scollard, et al., "Polymerization of ά-Olefins by Chelating Diamide Complexes of Titanium", Macromolecules, vol. 29, 1996, pp. 5241-5243.

Shapiro, et al., "[$\{(\eta^{5+}\text{-}C_5Me_r)Me_2Si\eta^1\text{-}NCMe_3)\}(PMe_3)ScH]_2$: A Unique Example of a Single-Component ά-Olefin Polymerization Catalyst", vol. 9, 1990, pp. 867-869.

Shapiro, et al., "Model Ziegler-Natta ά -Olefin Polymerization Catalysts Derived from [$\{(\eta^5\text{-}C_5Me_4)SiMe_2(\eta^1\text{-}NCMe_3)\}(PMe_3)Sc(\mu_2\text{-}H)]_2$ and [$\{(\eta^5\text{-}C_5Me_4)SiMe_2(\eta^1\text{-}NCMe_3)\}Sc(\mu_2\text{-}CH_2CH_2CH_3)]_2$. Synthesis, Structures, and Kinetic and Equilibrium Investigations of the Catalytically Active Species in Solution", J. Am. Chem. Soc., vol. 116, 1994, pp. 4623-4640.

Zucchi, et al., "Structural and Photophyiscal Behaviour of Lanthanide Complexes with a Tetraazacyclododecane Featuring Carbamoyl Pendant Arms", J. Chem. Soc., Dalton Trans., 1999, pp. 931-938.

\* cited by examiner

CATIONIC GROUP-3 CATALYST SYSTEM

This application claims the benefit of U.S. provisional application 60/241,652, filed Oct. 19, 2000, and 60/243,207, filed Oct. 25, 2000.

FIELD

This invention relates to certain transition metal compounds from Group 3 of the Periodic Table of Elements, and to a catalyst system comprising Group-3 or Lanthanide transition metal compounds and alumoxane, modified alumoxane, non-coordinating anion activator, Lewis acid, or the like to form active cationic catalyst species for the production of polyolefins such as polyethylene, polypropylene and alpha-olefin copolymers of ethylene and propylene having a high molecular weight.

BACKGROUND

Neutral scandium compounds having two univalent ligands or a bidentate, divalent ligand are known from Shapiro et al., *Organometallics*, vol. 9, pp. 867-869 (1990); Piers et al., *J. Am. Chem. Soc.*, vol. 112, pp. 9406-9407 (1990); Shapiro et al., *J. Am. Chem. Soc.*, vol. 116, pp. 4623-4640 (1994); Hajela et al., *Organometallics*, vol. 13, pp. 1147-1154 (1994); and U.S. Pat. No. 5,563,219 to Yasuda et al. Similar yttrium, lanthanum and cerium complexes are disclosed in Booij et al., *Journal of Organometallic Chemistry*, vol. 364, pp. 79-86 (1989) and Coughlin et al., *J. Am. Chem. Soc.*, vol. 114, pp. 7606-7607 (1992). Polymerization with a metal scandium complex having a bidentate, divalent ligand using a non-ionizing cocatalyst is known from U.S. Pat. No. 5,464,906 to Patton et al.

Group-3-10 metallocyclic catalyst complexes are described in U.S. Pat. Nos. 5,312,881 and 5,455,317, both to Marks et al. U.S. Pat. No. 5,064,802 to Stevens et al.; and EP 0 765 888 A2. U.S. Pat. No. 5,763,556 to Shaffer et al. describes Group-3 olefin polymerization catalysts.

Polymerization of olefins with cationic Group-4 metal complexes is illustrated in WO 96/13529 and WO 97/42228. Boratabenzene complexes of Group-3-5 metals are disclosed in WO 97/23493.

Amidinato complexes of Group-3-6 metals are disclosed in U.S. Pat. No. 5,707,913 to Schlund et al. Group 4 bisamido catalysts are disclosed in U.S. Pat. No. 5,318,935 to Canich, et al., and related multidentate bisarylamido catalysts are disclosed by D. H. McConville, et al, *Macromolecules* 1996 29, 5241-5243.

S. Hajela, W. P. Schaefer, J. E. Bercaw, *J. Organomet. Chem.* vol. 532, pp. 45-53 (1997) describes the synthesis of Group-3 metal complexes $(Me_3\text{-TACN})M(CH_3)_3$ (M=Sc, Y) and reactions of the Sc species with activators ([PhNMe$_2$H] [B(C$_6$F$_5$)$_4$] and B(C$_6$F$_5$)$_3$) and subsequent polymerization of ethylene and oligomerization of 1-pentene (with unspecified catalyst activities).

L. W. M. Lee, W. E. Piers, M. R. Elsegood, W. Clegg, M. Parvez, *Organometallics* vol. 18, pp. 2947-2949 (1999) describes the synthesis of a scandium dibenzyl complex with a β-diketiminato ancillary ligand, and the generation, by reaction with the Lewis acid B(C$_6$F$_5$)$_3$, of an ionic derivative with a contact ion-pair structure (unreactive towards alkenes).

M. A. H. Male. M. E. G. Skinner, P. J. Wilson, P. Mountford, M. Schröder, *New J. Chem.* vol. 24, pp. 575-577 (2000) reports the synthesis of a substituted 1,4,7-triazacyclononane ligand, iPr$_2$-TACN-(CH$_3$)$_3$NH$_2$ and a corresponding titanium TACN-imido complex [iPr$_2$-TACN-(CH$_3$)$_3$N]TiCl$_2$ (in which the ligand is dianionic).

Monoanionic substituted TACN ligands (with pendant phenolate or alcoholate functions) can be found e.g. in C. Flassbeck, K. Wieghardt, *Z. Anorg. Allg. Chem.* vol. 608, pp. 60-68 (1992), and in D. A. Robson, L. H. Lees, P. Mountford, M. Schröder, *Chem. Commun.* pp. 1269-1270 (2000).

The synthesis and structure of a lithium salt of a substituted TACN ligand with a pendant cyclopentadienyl anion is reported in B. Quian, L. M. Henling, J. C. Peters, *Organometallics* vol. 19, pp. 2805-2807.

SUMMARY

The present invention encompasses a catalyst system for polymerization comprising a cationic Group-3 or Lanthanide metal stabilized by an anionic multidentate ligand and at least one other ligand. The multidentate ligand and the metal together form a metallocycle. Some embodiments select the metal from scandium, yttrium, or lanthanum, although other lanthanides are also suitable.

In some embodiments, the multidentate ligand, A, has the formula LTE wherein L is a bulky neutral ligand, some of those embodiments contain at least two Group-15-16 atoms, others at least three. The Group-15-16 atoms connect to the metal, M, using lone pair electrons. T is a covalent bridging group containing a Group-13-14, or -15 element. E is an anionic ligand containing a Group-14-16 element, including π-donating hydrocarbyl and heterohydrocarbyl ligands, substituted amido or phosphido ligands, oxygen or sulfur, or other ligands or atoms covalently bound to T. Alternatively, E is JR'$_z$ where J represents a Group-15 or -16 element. When J is a Group-15 element, z=1, and when J is a Group-16 element, z=0. Finally, each R' is independently selected from suitable organic ligands as defined below.

In a further embodiment, a polymerization process according to the present invention (invention polymerization process), such as the polymerization or copolymerization of olefins, comprising the steps of activating (ionizing) the Group-3 or Lanthanide metal component to a cation (the catalyst) and contacting it with suitable feedstocks. The catalyst can optionally be dissolved, suspended, or fluidized in a suitable liquid or gaseous polymerization diluent. The catalyst is activated with alumoxanes, modified alumoxanes, non-coordinating anion activators, Lewis acids, or the like, (alone or in combination), with an aluminium-to-non-coordinating-anion or Lewis-acid-to-transition-metal molar ratio of 1:10 to 20,000:1 or more. The catalyst reacts with the monomer(s) from −100° C. to 300° C. for one second to 10 hours to produce a polyolefin having from 1000 or less to 5,000,000 or more weight average molecular weight and from 1.5 to 15.0 or greater molecular weight distribution.

Definitions

Catalyst system encompasses a catalyst precursor/activator pair. When catalyst system is used to describe such a pair before activation, it means the unactivated catalyst together with the activator. When catalyst system is used to describe such a pair after activation, it means the activated catalyst and the NCA or other charge-balancing moiety.

Cp or cyclopentadienyl encompasses all substituted and unsubstituted ligands in which the 5-carbon-atom, planar aromatic cyclopentadienide ion can be found. This specifically includes fused ring systems in which the 5-carbon ring is fused with other 5-membered rings and fused with 6-and-greater-membered rings. It also specifically includes ligands in which ring carbon atoms are substituted with heteroatoms giving heterocyclic systems. The cyclopentadienyl ligand's 5-member, substantially planar ring should be preserved (heterocyclic or homocyclic), including the π-electrons used to coordinate, side on, to M. Some examples of Cp or cyclopentadienyl are fluorenyl, indenyl, and the cyclopentadiene monoanion itself.

Feedstocks are any desired mixture of ethylene, $C_3$-$C_{20}$ α-olefins, $C_4$-$C_{20}$ diolefins, acetylenically unsaturated monomers, or other unsaturated monomers. These feedstocks contain predominately one monomer for homopolymerization; they contain monomer mixtures for copolymerization reactions.

L' is a neutral Lewis base such as, diethyl ether, tetrahydrofuran, dimethylaniline, trimethylphosphine, lithium chloride, or the like, coordinated to the metal center. It also optionally binds to one or both X, with an appropriate X. L' can also be a second transition metal of the same type as the metal center giving a dimeric catalyst or catalyst precursor, if both of the transition metals are the same, or a bimetallic catalyst or catalyst precursor if the transition metals are different.

Monodentate means that a ligand is coordinated to an atom through substantially one, substantially discrete, ligand-atom connection, coextensive with the art-recognized meaning.

Bidentate means that a ligand is coordinated to an atom through substantially two, substantially discrete, ligand-atom connections. This definition of bidentate is coextensive with the art-recognized meaning.

Multidentate means that a ligand is substantially coordinated to an atom through more than one substantially discrete, ligand-atom connection, which is coextensive with the art-recognized meaning.

Noncoordinating anion (NCA) is art recognized to mean an anion that either does not coordinate to the metal cation or that does coordinate to the metal cation, but only weakly. Weakly enough that a neutral Lewis base, such as an olelinically or acetylenically unsaturated monomer can displace it. Any metal or metalloid that can form a compatible, weakly or negligibly coordinating complex may be used or contained in the noncoordinating anion. Suitable metals include, but are not limited to, aluminum, gold, and platinum. Suitable metalloids include, but are not limited to, boron, phosphorus, and silicon.

Polymerization encompasses any polymerization reaction such as homopolymerization and copolymerization. It encompasses polymer production including both homopolymers and copolymers with other α-olefin, α-olefinic diolefin, or non-conjugated diolefin monomers, for example $C_3$-$C_{20}$ olefins, $C_4$-$C_{20}$ diolefins, $C_4$-$C_{20}$ cyclic olefins, or $C_8$-$C_{20}$ styrenic olefins. Other olefinically unsaturated monomers besides those specifically described above may be polymerized using the invention catalysts, for example, styrene, alkyl-substituted styrene, ethylidene norbornene, norbornadiene, dicyclopentadiene, vinylcyclohexane, vinylcyclohexene, and other olefinically-unsaturated monomers, including other cyclic olefins, such as cyclopentene, norbornene, and alkyl-substituted norbornenes. Copolymerization can also incorporate α-olefinic macromonomers of up to 1000 or more mer units.

Q are abstractable ligands or leaving groups and olefin insertion ligands connected to the metal center. Usually, activation occurs when one or more Q are removed from the metal. Also, one or more Q remains and as part of the polymerization process, olefin monomer inserts into the metal-center-Q bond. Thus, the Q that remains on the metal center is known as an olefin insertion ligand. Qs independently include, but are not limited to, monoanionic ligands selected from, hydride, hydrocarbyl, alkoxide, aryloxide, amide, or phosphide radicals. Furthermore, both Q together may be an alkylidene, a cyclometallated hydrocarbyl, or any other divalent anionic chelating ligand, or Q can be a diene. Exemplary Q in the formulas are diethyl, propyl, butyl, pentyl, isopentyl, hexyl, isobutyl, heptyl, octyl, nonyl, decyl, cetyl, 2-ethylhexyl, phenyl, benzyl, trimethylsilylmethyl, triethylsilylmethyl and the like. Some embodiments limit at least one Q to trimethylsilylmethyl. Exemplary halogen atoms for Q include chlorine, bromine, fluorine, and iodine. Some embodiments select Q as chlorine. Exemplary alkoxides and aryloxides for Q are methoxide, phenoxide and substituted phenoxides such as 4-methyl-phenoxide. Exemplary amides for Q are dimethylamide, diethylamide, methylethylamide, di-t-butylamide, diisopropylamide, and the like. Exemplary arylamides are diphenylamide and any other substituted phenylamides. Exemplary phosphides for Q are diphenylphosphide, dicyclohexylphosphide, diethylphosphide, dimethylphosphide, and the like. Exemplary alkylidene radicals for both Q together are methylidene, ethylidene, and propylidene. Exemplary cyclometallated hydrocarbyl radicals for both Q together are propylene, and isomers of butylene, pentylene, hexylene, and octylene. Exemplary dienes for both Q together are 1,3-butadiene, 1,3-pentadiene, 1,4-pentadiene, 1,3-hexadiene, 1,4-hexadiene, 1,5-hexadiene, 2,4-dimethyl-1,3-butadiene, 2-methyl-1,3-pentadiene, 2-methyl-1,3-hexadiene, and 2,4-hexadiene. Qs can also be simple alky ligands substituted with at least one trialkyl silyl group. The most preferred Q is —$CH_2SiMe_3$.

R, R', and R" encompass:

(i) $C_1$-$C_{20}$ hydrocarbyl radicals;

(ii) $C_1$-$C_{20}$ substituted hydrocarbyl radicals in which a halogen atom, amido, phosphido, alkoxy, or aryloxy group or any other radical containing a Lewis acidic or basic functionality replace one or more hydrogen atoms including straight and branched alkyl radicals, cyclic hydrocarbon radicals, alkyl-substituted cyclic hydrocarbon radicals, aromatic radicals, alkyl-substituted aromatic radicals such as trifluoromethyl, dimethylaminomethyl, diphenylphosphinomethyl, methoxymethyl, phenoxyethyl, trimethylsilylmethyl and the like; and (iii) $C_1$-$C_{20}$ hydrocarbyl-substituted metalloid radicals wherein the metalloid is a Group-13-14 element such as trimethylsilyl triethylsilyl, ethyldimethylsilyl, methyldiethylsilyl, triphenylgermyl and the like.

Additionally, any R or R" may join with one or more R or R" to form a ring structure. Separately, R" may also be a hydride radical.

TACN is 1,4,7-triazacyclononane.

TAN is 1,5,9-triazanonane.

TACH is 13,5-triazacyclohexane.

DACN is 1,4-diazacyclononane.

TACDD is 1,5,9-triazacyclododecane.

TNNCN is 1,2,6-triazacyclononane.

TNNCH is 1,2,5-triazacycloheptane.

TAH is 1,4,7-triazaheptane.

DETAILED DESCRIPTION

The Group 3 transition metal component of the catalyst system of the invention can be broadly defined by the formula:

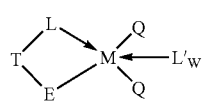
(A)

M is a Group-3 or Lanthanide metal.

LTE is a multidentate ligand that forms a metallocycle with M (metal): Q are ligands as described above.

L is a bulky, neutral multidentate ligand containing at least two, or three, Group-15 or -16 atoms. Some embodiments select the Group-15 or -16 atoms to be nitrogen.

T connects the multidentate ligand L, to the anionic ligand, E. T is a covalent bridging group containing at least one Group-13-16 atom. Its chain length influences the geometry of the (LTE)M metallocycle fragment. Examples of T include, but are not limited to, dialkyl, alkylaryl, or diaryl, silicon or germanium radical; alkyl or aryl, phosphine or amine radicals; or hydrocarbyl radicals such as methylene, ethylene, n-propylene, and isopropylene.

E is an anionic ligand containing at least one group 14-16 element and may be a substituted or unsubstituted, cyclopentadienyl, amide, or phosphide ligand, or a Group-16 element such as oxygen or sulfur.

When E is a substituted cyclopentadienyl ligand, the substitution can occur on the ring (on-ring), keeping the $C_5$ ring intact, or can occur in the ring, creating heterocyclic compounds. On-ring substitutions range from simple unitary substitution up to the replacement of multiple hydrogen atoms with multidentate ligands forming fused-ring systems such as in-ring or on-ring substituted, or unsubstituted, fluorenyl or indenyl ligands.

$L'_w$ is a neutral Lewis base and is defined above in the definitions section. "w"=0, 1, or 2.

In cationic form as activated for olefin polymerization, the transition metal complex is believed to have the following formula:

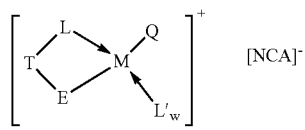
(B)

M, T, E L Q and L' are as defined above and NCA is a weakly coordinating or noncoordinating anion that balances the cationic complex's charge.

In two embodiments, transition metal components of the catalyst system have the formulas as shown below in C or D.

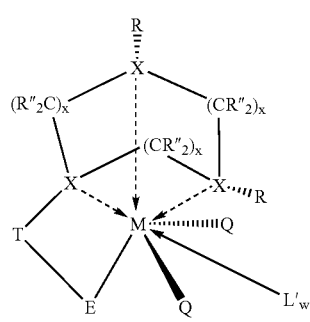
(C)

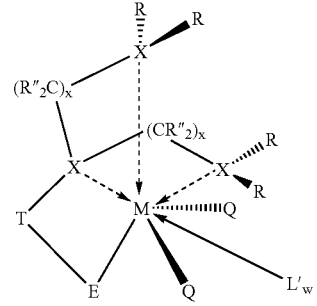
(D)

M, T, E, Q and L' are as defined above. X is a Group-15 element. In structures C and D as well as those below, "x" is 14. Some embodiments select X to be nitrogen. Some embodiments select "x" to be 2.

Note the difference between structures C and D. In C, the ligand L is cyclic as shown in structure E below, while in D, L is acyclic as shown in structure F below, Structures E and F were drawn with x=2.

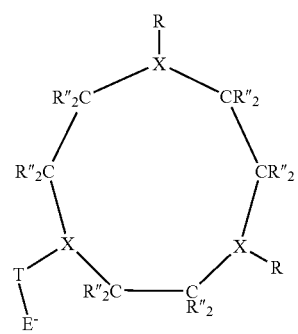
(E)

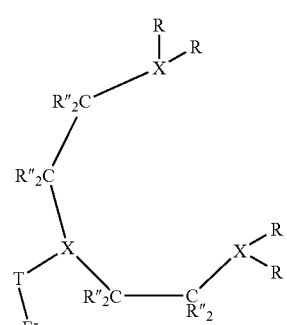
(F)

Alternatively, as in structures G and H, E is $JR'_z$. J is a Group-15 or -16 element; z is 1 when J is a Group 15 element and 0 when J is a Group 16 element. R, R' and R" are defined above.

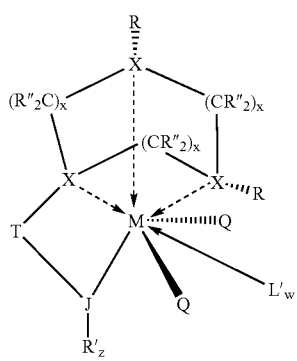

(G)

(H)

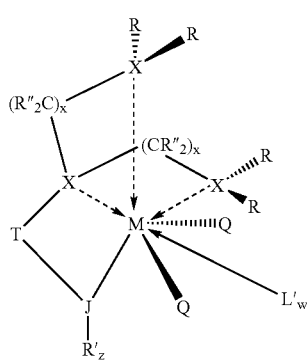

E can also be a cyclopentadienyl ligand (as defined above), as seen in I and J. The cyclopentadienyl ring is unsubstituted cyclopentadienide⁻ in I and is unsubstituted fluorenide in J.

(I)

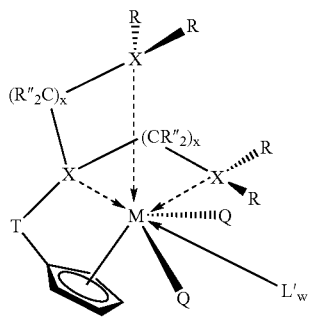

(J)

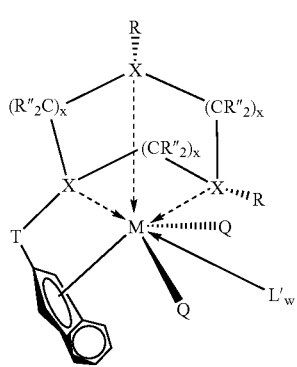

A catalyst precursor comprising a metal complex with the formula:

$$M(LTE)(Q)_nL'_w$$

where:
a) M is a Group-3 or lauthanide metal;
b) LTE is a multidentate ligand wherein L is a multidentate portion, E is an anion; and T is a group connecting L and E;
c) Q are radical ligands independently selected from hydride, hydrocarbyl, alkoxide, atyloxide, amide or phosphide radicals; an alkylidenyl or a cyclometallated hydrocarbyl radical; and a diene.
d) n is 1 or 2;
e) L' is an optional Lewis base; and
f) w+0, 1, or 2.

The metal complexes according to this invention can be prepared by various conventional routes. For example, the complex can be prepared by reacting a salt of the LTE-ligand with a Group-3 metal trihalide (or metal pseudohalide or metal alkoxide, etc.). A simple salt of the LTE-ligand plus an alkali or alkaline earth metal cation (e.g. Li, Na, MgX, etc.) reacts with a metal halide yielding $(LTE)MQ_2L'_w$. (Q is a halide). This $(LTE)MQ_2L'_w$ species can react with an alkyl-metal reagent, such as $Me_3SiCH_2Li$ to give the corresponding $(LTE)MR^1_2L'w$ ($R^1$=hydrocarbyl, etc.) catalyst precursor. These reactions can be carried out in the same reaction vessel. Alternatively, the catalyst precursor can be prepared starting with the neutral H(LTE) species can be reacted with homoleptic or heteroleptic metal hydrocarbyl compounds to yield the catalyst precursors.

The metal complexes (catalyst precursors) according to the invention are suitable for polymerization when activated by methods known in the metallocene art. Suitable activators typically include alumoxane compounds, modified alumoxane compounds, and ionizing anion precursor compounds that abstract one reactive, σ-bound, metal ligand making the metal complex cationic and providing a charge-balancing noncoordinating or weakly coordinating anion. When using ionizing anion precursor compounds alone, Q is limited to hydride, hydrocarbyl, and substituted hydrocarbyl radicals, including organometalloid-substituted hydrocarbyl radicals.

Alkylalumoxanes and modified alkylalumoxanes are suitable as catalyst activators, particularly when the abstractable ligand is a halide. Mixtures of different alumoxanes and modified alumoxanes may also be used. For further descriptions, see U.S. Pat. Nos. 4,665,208, 4,952,540, 5,041,584, 5,091,352, 5,206,199, 5,204,419, 4,874,734, 4,924,018, 4,908,463, 4,968,827, 5,329,032, 5,248,801, 5,235,081, 5,157,137, 5,103,031 and EP 0 561 476 A1, EP 0 279 586 B1 EP 0516476 A, EP0594 218 A1 and WO94/10180.

When the activator is an alumoxane (modified or unmodified), some embodiments select the maximum amount of activator is a 5000-fold molar excess over the catalyst precursor (per metal catalytic site). The minimum activator-to-catalyst-precursor is a 1:1 molar ratio.

Descriptions of ionic catalysts with a transition-metal cationic complex and a noncoordinating anion, suitable for polymerization appear in U.S. Pat. Nos. 5,064,802, 5,132,380, 5,198,401, 5,278,119, 5,321,106, 5.347,024, 5,408,017, 5,599,671, and WO 92/00333 and WO 93/14132. These teach a preparation method in which metallocenes are protonated by noncoordinating anion precursors such that a substituted or unsubstituted alkyl or hydride group (denoted Q in this disclosure) is abstracted from the transition metal compound making it both cationic and charge-balanced by the noncoordinating anion. Since similar ligands may be present in this invention's catalyst precursors, similar polymerization-catalyst activation methods may be followed.

Using ionic compounds lacking an active proton, but capable of producing both an active metal cationic complex and a noncoordinating anion, is also possible. See, EP-A-0 426 637, EP-A-0 573 403 and U.S. Pat. No. 5,387,568 for illustrative ionic compounds. Reactive cations of the ionic compounds, other than the Bronsted acids, include ferrocenium, silver, tropylium, triphenylcarbenium and triethylsilylium, and alkali and alkaline earth metal cations such as sodium, magnesium or lithium cations. A further class of suitable noncoordinating anion precursors contains hydrated salts comprising alkali or alkaline-earth metal cations and a non-coordinating anion as described above. The hydrated salts are made by reacting the metal-cation-noncoordinating-anion salt with water, for example, by hydrolysis of the commercially available or readily synthesized $[Li]^+[B(pfp)_4]^-$, which yields $[Li(H_2O)_x]^+[B(pfp)_4]^-$: pfp is pentafluorophenyl or perfluorophenyl.

An additional method of making this invention's active polymerization catalysts uses ionizing anion precursors that are initially neutral Lewis acids but form a cationic metal complex and a noncoordinating anion, or a Zwitterionic complex upon reaction with the invention compounds. For example, tris(pentafluorophenyl) boron or aluminum act to abstract a hydrocarbyl or hydride ligand to yield an invention cationic metal complex and stabilizing noncoordinating anion, see EP-A-0 427 697 and EP-A-0 520 732 for illustrations of analogous Group-4 metallocene compounds. Also, see the methods and compounds of EP-A-0 495 375. For formation of zwitteronic complexes using analogous Group 4 compounds, see U.S. Pat. Nos. 5,624,878; 5,486,632; and 5,527,929.

When the cations of noncoordinating anion precursors are Bronsted acids such as protons or protonated Lewis bases (excluding water), or reducible Lewis acids such as ferrocenium or silver cations, or alkali or alkaline earth metal cations such as those of sodium, magnesium or lithium, the catalyst-precursor-to-activator molar ratio may be any ratio. Combinations of the described activator compounds may also be used for activation. For example, tris(perfluorophenyl) boron can be used in conjunction with methylalumoxane.

The invention's catalyst complexes are useful in polymerizing unsaturated monomers conventionally known to undergo metallocene-catalyzed, polymerization such as solution polymerization, slurry polymerization, gas-phase polymerization, and high-pressure polymerization. These catalysts may be supported and as such will be particularly useful in the known, fixed-bed, moving-bed, fluid-bed, slurry, or solution operating modes conducted in single, series, or parallel reactors.

Generally, when using this invention's catalysts, particularly when they are immobilized on a support, the complete catalyst system will additionally comprise one or more scavenging compounds. Here, the term "scavenging compounds" means compounds that remove polar impurities from the reaction environment. These impurities adversely affect catalyst activity and stability. Purifying steps usually occur before introducing reaction components to the reaction vessel. But such steps will rarely allow polymerization without using some scavenging compounds. Normally, the polymerization process will still use at least small amounts of scavenging compounds.

Typically, the scavenging compound will be an organometallic compound such as the Group-13 organometallic compounds of U.S. Pat. Nos. 5,153,157, 5,241,025 and WO-A-91/09882, WO-A-94/03506. WO-A-93/14132, and that of WO 95/07941. Exemplary compounds include triethyl aluminum, triethyl borane, triisobutyl aluminum, methylalumoxane, isobutyl aluminumoxane, and tri-n-octyl aluminum. Those scavenging compounds having bulky or $C_6$-$C_{20}$ linear hydrocarbyl substituents covalently bound to the metal or metalloid center usually minimize adverse interaction with the active catalyst. Examples include triethylaluminum, but more preferably, bulky compounds such as triisobutylaluminum, triisoprenylaluminum, and long-chain linear alkyl-substituted aluminum compounds, such as tri-n-hexylaluminum, tri-n-octylaluminum, or tri-n-dodecylaluminum. When alumoxane is used as the activator, any excess over that needed for activation will scavenge impurities and additional scavenging compounds may be unnecessary. Alumoxanes also may be added in scavenging quantities with other activators, e.g., methylalumoxane, $[Me_2HNPh]^+[B(pfp)_4]^-$ or $B(pfp)_3$.

The invention catalysts can be supported for gas-phase, bulk, or slurry polymerization use, or otherwise as needed. Numerous support methods are known for catalysts in the olefin copolymerization art, particularly alumoxane-activated catalysts; any are suitable for this invention's broadest practice. See, for example, U.S. Pat. Nos. 5,057,475 and 5,227,440. An example of supported ionic catalysts appears in WO 94/03056. U.S. Pat. No. 5,643,847 and WO 96/04319A describe a particularly effective method. A bulk or slurry process using this invention's supported metal complexes activated with alumoxane can be used for ethylene-propylene rubber as described in U.S. Pat. Nos. 5,001,205 and 5,229,478. Additionally, those processes suit this invention's catalyst systems. Both polymers and inorganic oxides may serve as supports, as is known in the art. See U.S. Pat. Nos. 5,422,325, 5,427,991, 5,498,582 and 5,466,649, and international publications WO 93/11172 and WO 94/07928.

Varying embodiments employ the catalyst system in the liquid phase (solution, slurry, suspension, bulk phase, or suitable combinations), in high-pressure, liquid or supercritical fluid phases, or in the gas phase. Each may be employed in singular, parallel, or series reactors. The liquid processes comprise contacting olefin monomers with the catalyst system described above. The reaction is carried out in a suitable diluent or solvent for a time sufficient to produce this invention's copolymers. Both aliphatic and aromatic hydrocarbyl solvents are suitable; some embodiments select hexane or toluene. Typically, in bulk and slurry processes, the liquid monomer slurry contacts the supported catalysts. Gas-phase processes typically use a supported catalyst and are conducted in any suitable manner for ethylene homo- or copolymerization. Illustrative examples may be found in U.S. Pat. Nos. 4,543,399, 4,588,790, 5,028,670 5,382,638, 5352,749, 5,436,304, 5,453,471, 5,463,999, and WO 95/07942.

Polymerization reaction temperatures can vary. The minimum reaction temperature is −50° C.; in some embodiments, the minimum is −20° C. The maximum temperature is 250° C.; some embodiments select the reaction temperature to be at or below 200° C.

Linear polyethylene, including high- and ultra-high-molecular-weight polyethylenes are produced by adding ethylene, and optionally one or more other monomers, to a reaction vessel with an invention catalyst. The invention catalyst is first slurried with or dissolved in a solvent, such as hexane or toluene. Gas-phase polymerization can be conducted, for example, in a continuous, fluidized-bed, gas-phase reactor operated between 200-3000 kPa and at 60-160° C., using hydrogen as a reaction modifier (100-200 ppm), a $C_4$-$C_8$ comonomer feedstream (0.5-12 mol %), and a $C_2$ feedstream (25-35 mol %), and a supported catalyst. See, U.S. Pat. Nos. 4,543,399; 4,588,790; 5,028,670; 5,405,922; and 5,462,999.

Ethylene-α-olefin (including ethylene-cyclic olefin and ethylene-α-olefin-diolefin) elastomers of high molecular weight and low crystallinity can be prepared using the invention catalysts under traditional solution polymerization conditions or by introducing ethylene gas into a slurry of polymerization diluent and catalyst. The polymerization diluent contains α-olefin monomers, cyclic olefin monomers, or their mixtures with other polymerizable and non-polymerizable monomers. In this case, polymerization reaction pressure varies, as well. The minimum pressure is 0.0013 bar: a pressure of at least 0.1 bar sometimes selected. The reaction pressure is usually at least 1.0 bar. The maximum pressure is 2500 bar. Some embodiments select the maximum pressure to be 1600 or 500 bar. Typical ethylene pressures will be between 10 and 1000 psig (69-6895 kPa) and the polymerization diluent temperature will typically be between –10 and 160° C. The process can use a stirred-tank reactor, or more than one reactor operated in series or parallel. See the general disclosure of U.S. Pat. No. 5,001,205.

Slurry or gas-phase reaction processes can use pre-polymerization of the supported invention catalyst to further control polymer particle morphology, as is known in the art. For example, such reaction can be accomplished by pre-polymerizing a $C_2$-$C_6$ α-olefin for a limited time. Ethylene contacts the supported catalyst at between –15° to 30° C. and ethylene pressure of up to 250 psig (1724 kPa) for 75 min to obtain a polyethylene coating on the support (30,000-150,000 molecular weight). The above polymerization process can then use the pre-polymerized catalyst. Additionally, polymeric resins may be used as a support coating, typically by suspending a support in dissolved polystyrene resin or similar material followed by separation and drying.

The invention catalyst compositions can be used individually as described above or can be mixed with other known polymerization catalysts to prepare polymer blends. Monomer and catalyst selection allows polymer blend preparation under conditions analogous to those using individual catalysts. Polymers having increased MWD for improved processing and other traditional benefits available from polymers made with mixed catalyst systems can thus be achieved.

Examples of the catalyst precursor number in the thousands. Representative examples of catalyst precursor are provided below. These exemplify a small subset of the invention catalyst precursors. This list does not limit the compounds in any way.

Methylene-Bridged, TACN Catalyst Precursors

[1-butyl-1-isopropyl-methylene-(propyl, ethyl-TACN) (2,3-dimethyl-6-phenylindenyl)] (isopentoxy) (phenoxy) yttrium; [1-ethyl-11-hexyl-methylene-(ethyl(triethylsilyl), 3-methylpentyl-TACN) (indenyl)] (methoxy) (ethyl(triethylsilyl))yttrium; [1-isopropyl-1-ethyl-methylene-(propyl, methyl-TACN) (isopropylamido)] (methyl(trimethylsilyl)) (isopropyl) yttrium; [1,1-diisopropyl-methylene-(octyl, methyl-TACN) (2-propylcyclopentadienyl)] (methyl(triethylsilyl)) (propoxy) yttrium; [1-isopropyl-1-methyl-methylene-(isopentyl, ethyl(trimethylsilyl)-TACN) (propylamido)] (ethyl(trimethylsilyl)) (methylnonylphosphido) yttrium; [1-isopropyl-1-methyl-methylene-(diethyl(trimethylsilyl)-TACN) (phenylamido)] (butyl) (phenoxy) yttrium; [1-isopropyl-1-methyl-methylene-(pentyl, methyl-TACN) (t-butylamido)] (phenoxy) (isopentoxy) yttrium; [1-methyl-1-ethyl-methylene-(butyl t-butyl-TACN) (2,3,4-trimethyl-5-ethylcyclopentadienyl)] (methylpropylphosphido) (octyl) yttrium; [1-methyl-1-ethyl-methylene-(propyl, heptyl-TACN) (fluorenyl)] (methylpropylamido) (heptyl) yttrium; [1-methyl-1-isopropyl-methylene-(pentyl, 3-methylpentyl-TACN) (tetramethycyclopentadienyl)] (2-methy-4-ethylphenoxy) (t-butoxy) yttrium; [1-methyl-1-isopropyl-methylene-(t-butyl, methyl(triethylsilyl)-TACN) (methylphosphido)] (dimethylphosphido) (isopropoxy) yttrium; [1,1-dimethyl-methylene-(octyl, t-butyl-TACN) (2,3,4-trimethyl-5-ethyl-cyclopentadienyl)] (ethyl(trimethylsilyl)) (diphenylamido) yttrium; [1-methyl-1-phenyl-methylene-(ethyl(triethylsilyl), ethyl-TACN) (perfluorofluorenyl)] (pentyl) (propyl) yttrium; [1-methyl-1-phenyl-methylene-(phenyl, propyl-TACN) (tetramethycyclopentadienyl)] (methyl(triethylsilyl)) (methylethylphosphido) yttrium; [-methyl-1-propyl-methylene-(ethyl, isopentyl-TACN) (cyclopentadienyl)] (diphenylphosphido) (t-butyl) yttrium; [1-methyl-1-propyl-methylene-(heptyl, phenyl-TACN) (phenylamido)] (phenoxy) (methyl(nonyl)phosphido) yttrium; [1-methyl-1-propyl-methylene-(isopropyl, heptyl-TACN) (methylphosphido)] (ethoxy) (ethyl(trimethylsilyl)) yttrium; [1-pentyl-1-ethyl-methylene-(isopropyl, ethyl(trimethylsilyl)-TACN) (tetramethylcyclopentadienyl)] (methylethylphosphido) (t-butoxy) yttrium; [1-phenyl-1-ethyl-methylene-(diethyl(triethylsilyl)-TACN) (phenylamido)] (3-methylpentyl) (isopentoxy) yttrium; [1-phenyl-1-ethyl-methylene-(hexyl, t-butyl-TACN) (2-propylcyclopentadienyl)] (diphenylphosphido) (methyl(triethylsilyl))yttrium; [1-phenyl-1-isopropyl-methylene-(propyl, heptyl-TACN) (propylamido)] (methylethylamido) (dimethylphosphido) yttrium; [1-phenyl-1-methyl-methylene-(diethyl-TACN) (methylphosphido)] (ethyl) (3-methylpentyl) yttrium; [1-phenyl-1-pentyl-methylene-(methyl, phenyl-TACN) (cyclopentadienyl)] (ethoxy) (isohexyl) yttrium; [1,2-diphenyl-methylene-(heptyl, ethyl-TACN) (methylamido)] (methyl (triethylsilyl)) (ethyl(trimethylsilyl))yttrium. [1-propyl-1-methyl-methylene-(isopentyl, pentyl-TACN) (perfluorofluorenyl)] (methylethylamido) (t-butyl) yttrium; [1-propyl-1-methyl-methylene-(diisopropyl-TACN) (tetramethylcyclopentadienyl)] (phenylethylphosphido) (methylpropylphosphido) yttrium; [1-propyl-1-methyl-methylene-(methyl(triethylsilyl), phenyl-TACN) (methylamido)] (methylpropylphosphido) (ethylpentylphosphido) yttrium; [1-propyl-1-methyl-methylene-(propyl, ethyl-TACN) (isopropylamido)] (dimethylamido) (butoxy) yttrium; [1-propyl-1-phenyl-methylene-(methyl, propyl-TACN) (methylamido)] (t-butoxy) (isohexyl) yttrium; [1-propyl-1-phenyl-methylene-(t-butyl, ethyl-TACN) (perfluorocyclopentadienyl)] (3,6-dimethylphenoxy) (heptyl) yttrium; [1-ethyl-1-propyl-methylene-(pentyl, ethyl-TACN) (2,4-dimethyl-6-phenylindenyl)] (ethoxy) (methylpropylamido) ytterbium; [1-isopropyl-1-phenyl-methylene-(butyl, propyl-TACN) (phenylamido)] (isopropyl) (methylnonylphosphido) thulium; [1-phenyl-1-isopropyl-methylene-(isopropyl, ethyl-TACN) (propylamido)] (ethylpentylphosphido) (phenylethylphosphido) terbium; [1-butyl-1-isopropyl-methylene-(isopropyl, methyl-TACN) (perfluorofluorenyl)] (isopentoxy) (isopentoxy) scandium; [1-butyl-1-phenyl-methylene-(diethyl(trimethylsilyl)-TACN) (2, 3,4-trimethyl-5-ethylcyclopentadienyl)] (t-butyl) (butyl) scandium; [1-isopentyl-1-ethyl-methylene-(heptyl, ethyl-TACN) (t-butylamido)] (ethylpentylphosphido) (methylethylphosphido) scandium; [1-isopentyl-1-isopropyl-methylene-(diisopropyl-TACN) (t-butylamido)] (diphenylamido) (phenylethylphosphido) scandium; [1-phenyl-1-isopropyl-methylene-(isopropyl, heptyl-TACN) (perfluorocyclopentadienyl)] (dimethylphosphido) (octyl) scandium; [1-phenyl-1-methyl-methylene-(diethyl-TACN) (perfluorocyclopentadienyl)] (ethyl(triethylsilyl)) (hexoxy)

scandium; [1,1-dimethylmethylene-(methyl, propyl-TACN) (2-propylcyclopentadienyl)] (isopentyl) (dimethylphosphido) samarium; [1-butyl-1-methyl-methylene-(t-butyl, methyl-TACN) (2-propylcyclopentadienyl)] (diphenylphosphido) (3,5-dimethylphenoxy) praseodymium; [1-propyl-1-methyl-methylene-(isopropyl, butyl-TACN) (perfluorofluorenyl)] (butoxy) (phenylethylphosphido) neodymium; [1,1-dipropylmethylene-(methyl, heptyl-TACN) (2,3,4-trimethyl-5-ethylcyclopentadienyl)] (methoxy) (heptyl) neodymium: [1-methyl-1-butyl-methylene-(ethyl, isopropyl-TACN) (fluorenyl)] (diphenylamido) (butoxy) lutetium; [1-ethyl-1-isopropyl-methylene-(ethyl, isohexyl-TACN) (fluorenyl)] (isopropyl) (propyl) lanthanum; [1,1-diisopropyl-methylene-(ethyl, phenyl-TACN) (propylamido)] (isopropyl) (methyl (triethylsilyl))europium; [1-phenyl-1-isopropyl-methylene-(diethyl(trimethylsilyl)-TACN) (isopropylamido)] (diphenylamido) (phenylethylphosphido) europium; [1-phenyl-1-pentyl-methylene-(diisopropyl-TACN) (2-propylcyclopentadienyl)] (phenyl) (phenoxy) europium; [1-phenyl-1-propyl-methylene-(propyl, 3-methylpentyl-TACN) (perfluorocyclopentadienyl)] (methylethylamido) (phenylethylamido) europium; [1-ethyl-1-isopropyl-methylene-(isopentyl, propyl-TACN) (2,4-dimethyl-6-phenylindenyl)] (methoxy) (diphenylphosphido) cerium.

Silanylene-Bridged, TACN Catalyst Precursors

[1-butyl-1-isopropyl-silanylene-(dipropyl-TACN) (methylphosphido)] (2-methyl-5-ethyl-phenoxy) (methoxy) yttrium; [1,1-diethyl-silanylene-(pentyl, isopropyl-TACN) (perchloroindenyl)] (methyl(triethylsilyl)) (ethylpentylphosphido) yttrium; [1-ethyl-1-isopropyl-silanylene-(3-methylpentyl, ethyl-TACN) (2,4-dimethyl-6-phenylindenyl)] (dimethylphosphido) (ethyl(trimethylsilyl))yttrium; [1-ethyl-1-methyl-silanylene-(propyl, hexyl-TACN) (perchloroindenyl)] (hexoxy) (phenoxy) yttrium; [1-ethyl-1-methyl-silanylene-(t-butyl, isopropyl-TACN) (propylamido)] (diphenylphosphido) (diphenylphosphido) yttrium; [1-isopropyl-1-butyl-silanylene-(hexyl, propyl-TACN) (indenyl)] (3-methylpentyl) (pentoxy) yttrium; [1-isopropyl-1-ethyl-silanylene-(dipropyl-TACN) (perfluorocyclopentadienyl)] (methyl(trimethylsilyl)) (isopentyl) yttrium; [1-methyl-1-hexyl-silanylene-(ethyl(trimethylsilyl), isopentyl-TACN) (2,4-dimethyl-6-phenylindenyl)] (methylpropylamido) (ethylpentylphosphido) yttrium; [In-methyl-1-isopropyl-silanylene-(diethyl(trimethylsilyl)-TACN) (t-butylamido)] (isohexyl) (3,5-dimethylphenoxy) yttrium; [1-methyl-1-isopropyl-silanylene-(isohexyl, methyl-TACN) (phenylamido)] (methoxy) (methyl(triethylsilyl))yttrium; [1,1-dimethylsilanylene-(hexyl, methyl-TACN) (perchloroindenyl)] (phenyl) (isopropoxy) yttrium; [1,1-dimethylsilanylene-(propyl, ethyl-TACN) (2-propylcyclopentadienyl)] (propyl) (methylpropylphosphido) yttrium; [1,1-dimethylsilanylene-(dipropyl-TACN) (2,4-dimethyl-6-phenylindenyl)] (2,5-dimethylphenoxy) (methyl) yttrium; [1-phenyl-1-isopentyl-silanylene-(propyl, methyl(triethylsilyl)-TACN) (perfluorofluorenyl)] (isopropyl) (isohexyl) yttrium; [1-phenyl-1-isopropyl-silanylene-(t-butyl, hexyl-TACN) (methylphosphido)] (phenylethylphosphido) (diphenylamido) yttrium; [1,2-diphenylsilanylene-(ethyl, methyl-TACN) (fluorenyl)] (isopentoxy) (phenylethylamido) yttrium; [1-phenyl-1-propyl-silanylene-(methyl(trimethylsilyl), ethyl(triethylsilyl)-TACN) (cyclopentadienyl)] (dimethylamido) (isohexyl) yttrium [1-propyl-1-ethyl-silanylene-(methyl(trimethylsilyl), 3-methylpentyl-TACN) (cyclopentadienyl)] (octyl) (ethyl(triethylsilyl))yttrium; [1, 1-dipropylsilanylene-(phenyl, t-butyl-TACN) (fluorenyl)] (2-methy-4-ethylphenoxy) (methylethylamido) yttrium; [1,2-diphenylsilanylene-(octyl, 3-methylpentyl-TACN) (indenyl)] (ethoxy) (butoxy) thulium; [1-isopropyl-1-methyl-silanylene-(propyl, hexyl-TACN) (2,4-dimethyl-6-phenylindenyl)] (propyl) (methylethylamido) terbium; [1-phenyl-1-propylsilanylene-(dimethyl-TACN) (perchloroindenyl)] (butyl) (isopropyl) terbium; [1-propyl-1-isopropyl-silanylene-(methyl, phenyl-TACN) (methylamido)] (pentyl) (3-methylpentyl) terbium; [1-butyl-1-methyl-silanylene-(ethyl(trimethylsilyl), 3-methylpentyl-TACN) (isopropylamido)] (3-methylpentyl) (diphenylphosphido) scandium; [1-ethyl-1-methyl-silanylene-(heptyl, methyl(triethylsilyl)-TACN) (phenylamido)] (3-methylpentyl) (ethoxy) scandium; [1-ethyl-1-propylsilanylene-(isopropyl, methyl-TACN) (2-propylcyclopentadienyl)] (t-butyl) (t-butoxy) scandium; [1, 1-dimethylsilanylene-(isopropyl, phenyl-TACN) (isopropylamido)] (butyl) (3-methylpentyl) scandium; [1-methyl-1-propylsilanylene-(diisopropyl-TACN) (t-butylamido)] (hexoxy) (butyl) scandium; [1-methyl-1-propyl-silanylene-(diethyl-TACN) (tetramethycyclopentadienyl)] (2,5-dimethylphenoxy) (butyl) scandium; [1-phenyl-1-isopropyl-silanylene-(isopropyl, methyl-TACN) (2,3,4-trimethyl-5-ethylcyclopentadienyl)] (3-methylpentyl) (propyl) scandium; [1-propyl-1-ethyl-silanylene-(methyl, heptyl-TACN) (phenylamido)] (dimethylamido) (phenyl) scandium; [1-propyl-1-ethyl-silanylene-(propyl, ethyl-TACN) (fluorenyl)] (ethyl(trimethylsilyl)) (phenylethylamido) scandium; [1-propyl-1-phenyl-silanylene-(methyl isopentyl-TACN) (2,4-dimethyl-6-phenylindenyl)] (methylpropylamido) (dimethylphosphido) scandium; [1,1-diisopropyl-silanylene-(propyl, ethyl-TACN) (methylphosphido)] (ethyl(triethylsilyl)) (diphenylphosphido) samarium; [1-phenyl-1-methyl-silanylene-(isopropyl octyl-TACN) (perfluorofluorenyl)] (isohexyl) (pentoxy) samarium; [1-propyl-1-methyl-silanylene-(isopentyl, methyl-TACN) (isopropylamido)] (2-methy-4-ethylphenoxy) (ethoxy) samarium; [1-isopropyl-1-ethyl-silanylene-(pentyl propyl-TACN) (isopropylamido)] (ethyl) (methoxy) praseodymium; [1-ethyl-1-hexyl-silanylene-(propyl, octyl-TACN) (fluorenyl)] (2,4-dimethylphenoxy) (methylpropylamido) neodymium; [1-phenyl-1-butyl-silanylene-(hexyl, ethyl-TACN) (2-propylcyclopentadienyl)] (heptyl) (methylethylamido) neodymium; [1-phenyl-1-methyl-silanylene-(ethyl, pentyl-TACN) (perfluorofluorenyl)] (methoxy) (phenyl) lutetium; [1-phenyl-1-methyl-silanylene-(isohexyl, 3-methylpentyl-TACN) (2,4-dimethyl-6-phenylindenyl)] (ethylpentylphosphido) (2-methy-4-ethylphenoxy) lutetium; [1-ethyl-1-phenyl-silanylene-(ethyl, isopropyl-TACN) (propylamido)] (methoxy) (propyl) lanthanum; [1-phenyl-1-methyl-silanylene-(isopropyl, propyl-TACN) (t-butylamido)] (pentoxy) (methyl) lanthanum; [1-ethyl-1-propyl-silanylene-(ethyl, methyl-TACN) (2-propylcyclopentadienyl)] (propoxy) (butoxy) holmium; [1-isopropyl-1-phenyl-silanylene-(propyl, heptyl-TACN) (cyclopentadienyl) (isohexyl) (isopropyl) gadolinium; [1-methyl-1-phenyl-silanylene-(butyl, phenyl-TACN) (t-butylamido)] (pentyl) (2-methy-4-ethylphenoxy) erbium; [1-phenyl-1-ethyl-silanylene-(octyl, pentyl-TACN) (perfluorofluorenyl)] (ethoxy) (ethyl) dysprosium; [1-phenyl-1-isopropyl-silanylene-(propyl, ethyl-TACN) (t-butylamido)] (heptyl) (diphenylamido) dysprosium; [1-propyl-1-methyl-silanylene-(hexyl, isopropyl-TACN) (methylamido)] (ethylpentylphosphido) (octyl) dysprosium, [1, 1-dipropylsilanylene-(methyl(triethylsilyl), isohexyl-TACN) (tetramethycyclopentadienyl)] bis(diphenylamido) cerium.

Germanylene-Bridged, TACN Catalyst Precursors

[1-butyl-1-methyl-germanylene-(ethyl(triethylsilyl), ethyl (trimethylsilyl)-TACN) (propylamido)] (3,4-dimethylphenoxy) (phenoxy) yttrium; [1,1-diethyl-germanylene-(methyl, propyl-TACN) (ethylamido)] (t-butoxy) (2,6-dimethylphenoxy) yttrium; [1-ethyl-1-methyl-germanylene-(t-butyl, ethyl(triethylsilyl)-TACN) (2-propylcyclopentadienyl)] (ethyl) (isopropyl) yttrium; [1-ethyl-1-pentyl-germanylene-(3-methylpentyl, methyl-TACN) (phenylamido)] (hexyl) (3-methylpentyl) yttrium; [1-ethyl-1-phenyl-germanylene-(methyl, phenyl-TACN) (tetramethycyclopentadienyl)] (pentyl) (methylpropylamido) yttrium; [1-ethyl-1-propyl-germanylene-(isopropyl, iso-pentyl-TACN) (methylphosphido)] (hexoxy) (methylpropylphosphido) yttrium; [1-ethyl-1-propyl-germanylene-(dimethyl-TACN) (2,3,4-trimethyl-5-ethylcyclopentadienyl)] (phenyl) (butoxy) yttrium; [1-hexyl-1-ethyl-germanylene-(octyl, ethyl-TACN) (perfluorocyclopentadienyl)] (pentoxy) (octyl) yttrium; [1-isopentyl-1-ethyl-germanylene-(ethyl, propyl-TACN) (cyclopentadienyl)] (phenoxy) (propoxy) yttrium; [1-isopropyl-1-hexyl-germanylene-(methyl, heptyl-TACN) (methylamido)] (dihexyl) yttrium; [1-isopropyl-1-methyl-germanylene-(diethyl(triethylsilyl)-TACN) (fluorenyl)] (octyl) (ethoxy) yttrium; [1-isopropyl-1-pentyl-germanylene-(phenyl, methyl(trimethylsilyl)-TACN) (2,3,4-trimethyl-5-ethylcyclopentadienyl)] (phenoxy) (methylethylphosphido) yttrium; [1-isopropyl-1-phenyl-germanylene-(butyl, methyl (triethylsilyl)-TACN) (ethylamido)] (ethoxy) (methyl) yttrium; [1-isopropyl-1-phenyl-germanylene-(butyl, methyl-TACN) (phenylamido)] (methylethylphosphido) (isohexyl) yttrium; [1-isopropyl-1-phenyl-germanylene-(methyl, 3-methylpentyl-TACN) (ethylamido)] (methylethylphosphido) (t-butoxy) yttrium; [1,1-dimethylgermanylene-(methyl, heptyl-TACN) (2-propylcyclopentadienyl)] (methylnonylphosphido) (propyl) yttrium; [1,1-dimethylgermanylene-(dipropyl-TACN) (phenylamido)] (2-methy-4-ethylphenoxy) (methyl) yttrium; [1-methyl-1-propyl-germanylene-(ethyl, isopropyl-TACN) (tetramethycyclopentadienyl)] (isopentyl) (dimethylamido) yttrium; [1-methyl-1-propyl-germanylene-(diisohexyl-TACN) (propylamido)] (pentoxy) (methylethylamido) yttrium; [1-pentyl-1-phenyl-germanylene-(isopropyl, 3-methylpentyl-TACN) (perfluorocyclopentadienyl)] (methylethylamido) (phenoxy) yttrium; [1-phenyl-1-ethyl-germanylene-(ethyl, methyl-TACN) (2-propylcyclopentadienyl)] (isohexyl) (phenylethylphosphido) yttrium; [1-phenyl-1-isopropyl-germanylene-(pentyl, hexyl-TACN) (phenylamido)] (ethyl(triethylsilyl)) (ethoxy) yttrium; [1-propyl-1-ethyl-germanylene-(ethyl, isopropyl-TACN) (indenyl)] (methoxy) (pentyl) yttrium; [1-propyl-1-isopropyl-germanylene-(propyl isopropyl-TACN) (cyclopentadienyl)] (ethyl(triethylsilyl)) (ethyl(triethylsilyl))yttrium; [1,1-dipropylgermanylene-(ethyl, methyl(triethylsilyl)-TACN) (isopropylamido)] (propoxy) (methyl(trimethylsilyl))yttrium; [1,1-dipropylgermanylene-(methyl(triethylsilyl), propyl-TACN) (2-propylcyclopentadienyl)] (isopropoxy) (pentyl) yttrium; [1-ethyl-1-isopropyl-germanylene-(propyl, methyl(trimethylsilyl)-TACN) (2,3,4-trimethyl-5-ethylcyclopentadienyl)] (methylpropylamido) (pentyl) ytterbium; [1-isopropyl-1-butyl-germanylene-(hexyl, methyl-TACN) (perfluorocyclopentadienyl)] (methylnonylphosphido) (propyl) thulium; [1-isopropyl-1-phenyl-germanylene-(isopropyl, propyl-TACN) (t-butylamido)] (butyl) (ethyl(trimethylsilyl))thulium; [1,1-diethyl-germanylene-(isopropyl, isohexyl-TACN) (2,3,4-trimethyl-5-ethylcyclopentadienyl)] (pentyl) (dimethylphosphido) scandium; [1-isopropyl-1-ethyl-germanylene-(propyl, methyl-TACN) (tetramethycyclopentadienyl)] (isopropyl) (phenylethylamido) scandium; [1-isopropyl-1-propyl-germanylene-(propyl, methyl(trimethylsilyl)-TACN) (2,4-dimethyl-6-phenylindenyl)] (diphenylamido) (dimethylphosphido) scandium; [1-methyl-1-ethyl-germanylene-(ethyl, methyl-TACN) (perfluorofluorenyl)] (butoxy) (phenoxy) scandium; [1-methyl-1-ethyl-germanylene-(isopropyl, methyl(triethylsilyl)-TACN) (perfluorofluorenyl)] (isopentoxy) (butoxy) scandium; [1-phenyl-1-isopropyl-germanylene-(methyl, isopropyl-TACN) (phenylamido)] (t-butyl) (3-methylpentyl) scandium; [1,2-diphenylgermanylene-(isopropyl, octyl-TACN) (propylamido)] (phenyl) (methoxy) scandium; [1-propyl-1-ethyl-germanylene-(ethyl(trimethylsilyl), methyl-TACN) (2-propylcyclopentadienyl)] (2,5-dimethylphenoxy) (phenyl) scandium; [1-isopropyl-1-methyl-germanylene-(methyl, propyl-TACN) (phenylamido)] (phenylethylamido) (isopentoxy) samarium; [1-phenyl-1-isopropyl-germanylene-(isopropyl, methyl(trimethylsilyl)-TACN) (2-propylcyclopentadienyl)] (butoxy) (phenylethylamido) praseodymium; [1,1-dibutyl-germanylene-(diethyl(trimethylsilyl)-TACN) (methylphosphido)] (butyl) (2,4-dimethylphenoxy) neodymium; [1,1-diisopropyl-germanylene-(ethyl, butyl-TACN) (isopropylamido)] (methyl (trimethylsilyl)) (butyl) neodymium; [1-propyl-1-isopropyl-germanylene-(isopentyl, propyl-TACN) (fluorenyl)) (methyl (trielhylsilyl)) (isopropyl) neodymium; [1,1-dipropylgermanyleyne-(isopropyl, methyl-TACN) (cyclopentadienyl)] (butoxy) (methylpropylphosphido) neodymium; [1-ethyl-1-methyl-germanylene-(propyl, ethyl-TACN) (tetramethycyclopentadienyl)) (dimethylamido) (ethyl(triethylsilyl))lutetium; [1-propyl-1-hexyl-germanylene-(diethyl-TACN) (isopropylamido)) bis(methyl(triethylsilyl))lutetium; [1-propyl-1-isopropyl-germanylene-(isopropyl, isohexyl-TACN) (perfluorocyclopentadienyl)] (methyl(triethylsilyl)) (t-butyl) lanthanum; [1-hexyl-1-isopropyl-germanylene-(propyl, methyl-TACN) (2,4-dimethyl-6-phenylindenyl)] (ethyl(trimethylsilyl)) (isopentyl) gadolinium; [1-ethyl-1-propyl-germanylene-(methyl (trimethylsilyl), ethyl(trimethylsilyl)-TACN) (2-propylcyclopentadienyl)] (ethyl(triethylsilyl)) (butoxy) dysprosium; [1-propyl-1-isopropyl-germanylene-(diethyl-TACN) (2,4-dimethyl-6-phenylindenyl)] (isopentyl) (isopropyl) dysprosium; [1-ethyl-1-isopropyl-germanylene-(isopentyl, propyl-TACN) (cyclopentadienyl)] (methyl) (diphenylphosphido) cerium.

Ethylenyl-Bridged, TACN Catalyst Precursors

[1-ethyl-1-propyl-ethylene-(methyl, isopropyl-TACN) (ethylamido)] (methyl(trimethylsilyl)) (isopropyl) yttrium; [1,1-dimethylethylene-(isopropyl, ethyl-TACN) (t-butylphosphido)] (ethoxy) (methyl(trimethylsilyl))yttrium; [1-pentyl-1-methyl-ethylene-(ethyl(triethylsilyl), phenyl-TACN) (propylamido)] (methyl) (heptyl) yttrium; [1-phenyl-1-butyl-ethylene-(isohexyl, isopentyl-TACN) (1-chloro-2,3,4-trimethylfluorenyl)] (isopropoxy) (ethyl) yttrium; [1,2-diphenylethylene-(ethyl, methyl-TACN) (perchloroindenyl)] (methyl) (dimethylamido) yttrium; [1-propyl-1-isopropyl-ethylene-(ethyl, propyl-TACN) (perchloroindenyl)] (ethylpentylphosphido) (phenyl) yttrium; [1-propyl-1-phenyl-ethylene-(dimethyl(triethylsilyl)-TACN) (cyclopentadienyl)] (isohexyl) (methoxy) yttrium; [1,1-diethyl-ethylene-(ethyl (triethylsilyl), ethyl-TACN) (1-bromo-2,3,4-trimethylindenyl)] (ethyl(triethylsilyl)) (dimethylphosphido) scandium; [1-ethyl-1-pentyl-ethylene-(diethyl-TACN) (perfluorocyclopentadienyl)] (dimethylphosphido) (diphenylamido) scandium; [1-isopropyl-1-phenyl-ethylene-(ethyl, hexyl-TACN) (t-butylamido)] (propoxy) (diphenylphosphido) scandium; [1,1-methyl-2-isopropyl-ethylene-(methyl, octyl-TACN) (t-butylphosphido)] (t-butyl) (ethylpentylphosphido) scandium; [1,2-dimethyl-ethylene-(diethyl-TACN) (2,4,5,8-tetraphenylfluorenyl)] (methylethylphosphido) (hexyl) yttrium;

[1,1-diisopropyl-ethylene-(ethyl, t-butyl-TACN) (t-butylamido)] (methylpropylamido) (methylethylamido) neodymium; [1-methyl-2-propyl-ethylene-(methyl, isopentyl-TACN) (tetramethycyclopentadienyl)] (pentoxy) (methylpropylamido) scandium; [1-ethyl-2-isopropyl-ethylene-(isopropyl, isohexyl-TACN) (fluorenyl)] (diphenylphosphido) (ethylpentylphosphido) terbium; [1-ethyl-2-phenyl-ethylene-(ethyl(triethylsilyl), methyl-TACN) (phenylphosphido)] (t-butoxy) (methylethylamido) lutetium; [1-isopropyl-1-propyl-ethylene-(pentyl, ethyl-TACN) (2,3,4-trimethyl-5-ethylcyclopentadienyl)] (dimethylamido) (hexoxy) lutetium; [1,1-diisopropyl-ethylene-(3-methylpentyl, isopropyl-TACN) (methylphosphido)] (phenoxy) (heptyl) lanthanum; [1,2-dimethyl-ethylene-(3-methylpentyl, ethyl(triethylsilyl)-TACN) (perfluorofluorenyl)] (methylethylamido) (phenyl) praseodymium; [1,2-diethylethylene-(isopropyl, methyl(triethylsilyl)-TACN) (2,3,4-trimethyl-5-ethylcyclopentadienyl)] (ethyl) (hexyl) yttrium; [1,2-diphenylethylene-(isopropyl, ethyl-TACN) (indenyl)] (butoxy) (phenylethylamido) erbium; [1-propyl-2-ethyl-ethylene-(propyl, ethyl(trimethylsilyl)-TACN) (t-butylamido)] (methylethylamido) (2,3-dimethylphenoxy) scandium; [1-ethyl-1-phenyl-ethylene-(isopropyl, octyl-TACN) (indenyl)] (methylpropylphosphido) (methyl(triethylsilyl))dysprosium; [1-phenyl-2-ethyl-ethylene-(isopropyl, hexyl-TACN) (tetramethycyclopentadienyl)] (hexoxy) (isopentyl) lanthanum; [1,1-diethyl-ethylene-(pentyl, propyl-TACN) (2-propylcyclopentadienyl)] (pentyl) (ethylpentylphosphido) yttrium; [1-ethyl-2-methyl-ethylene-(isohexyl, methyl(trimethylsilyl)-TACN) (perfluorofluorenyl)] (t-butyl) (hexyl) yttrium; [1-ethyl-2-phenyl-ethylene-(isopropyl, propyl-TACN) (2,4-dimethyl-6-phenylindenyl)] (isopropoxy) (hexoxy) yttrium; [1-ethyl-2-phenyl-ethylene-(t-butyl, methyl-TACN) (perfluorofluorenyl)] (diphenylphosphido) (methyl(trimethylsilyl))yttrium; [1-isopropyl-2-methyl-ethylene-(ethyl, methyl-TACN) (phenylphosphido)] (methylpropylamido) (ethoxy) holmium; [1-isopropyl-2-methyl-ethylene-(t-butyl, methyl(trimethylsilyl)-TACN) (2,4,5,8-tetraphenylfluorenyl)] (methylethylamido) (methyl(triethylsilyl))dysprosium; [1-phenyl-2-isopentyl-ethylene-(ethyl, propyl-TACN) (2-propylcyclopentadienyl)] (dimethylamido) (ethoxy) yttrium; [1-phenyl-2-propyl-ethylene-(ethyl, isohexyl-TACN) (2,3-dibromoindenyl)] (pentoxy) (ethyl(triethylsilyl)) yttrium;

Propylenyl-Bridged, TACN Catalyst Precursors

[1-phenyl-1-ethyl-propylene-(octyl, methyl-TACN) (2,3-dibromoindenyl)] (methylpropylamido) (2-methy-4-ethylphenoxy) yttrium; [1-propyl-1-phenyl-propylene-(dimethyl-TACN) (2-propylcyclopentadienyl)] (ethyl) (t-butyl) yttrium; [1-pentyl-1-propyl-propylene-(diethyl-TACN) (perfluorofluorenyl)] (phenyl) (methylnonylphosphido) lanthanum; [1-isopropyl-1-methyl-propylene-(propyl, octyl-TACN) (perchloroindenyl)] (phenylethylamido) (propoxy) neodymium; [1,2-diphenylpropylene-(diethyl-TACN) (indenyl)] (hexyl) (phenylethylphosphido) yttrium; [1-propyl-1-isopropyl-propylene-(ethyl, methyl-TACN) (2-propylcyclopentadienyl)] (isopentoxy) (methylethylamido) yttrium; [1-isopropyl-1-ethyl-propylene-(isopropyl, isopentyl-TACN) (phenylphosphido)] (isopentyl) (diphenylamido) scandium; [1-phenyl-1-ethyl-propylene-(isopropyl, 3-methylpentyl-TACN) (perfluorofluorenyl)] (ethyl) (methyl) lanthanum; [1-propyl-1-methyl-propylene-(methyl, octyl-TACN) (cyclopentadienyl)] (phenoxy) (3,4-dimethylphenoxy) neodymium; (1-ethyl-1-phenyl-propylene-(methyl(trimethylsilyl), isopropyl-TACN) (fluorenyl)] (3-methylpentyl) (heptyl) yttrium; [1,1-dimethylpropylene-(t-butyl, phenyl-TACN) (indenyl)] (butoxy) (ethoxy) scandium; [1-isopropyl-1-ethyl-propylene-(ethyl, isopropyl-TACN) (2,4-dimethyl-6-phenylindenyl)] (isohexyl) (butoxy) yttrium; [1-butyl-2-methyl-propylene-(methyl(triethylsilyl), methyl-TACN) (phenylphosphido)] (hexoxy) (dimethylamido) ytterbium; [1-propyl-2-ethyl-propylene-(methyl, heptyl-TACN) (phenylphosphido)] (methylnonylphosphido) (phenylethylamido) yttrium; [1-isopropyl-2-methyl-propylene-(diethyl-TACN) (2,3,4-trimethyl-5-ethylcyclopentadienyl)] (isohexyl) (ethyl) lanthanum; [1-propyl-2-isopentyl-propylene-(methyl, isopentyl-TACN) (methylamido)) (butyl) (hexyl) yttrium; [1,2-dimethyl-propylene-(pentyl, propyl-TACN) (perfluorofluorenyl)] (methylnonylphosphido) (methylpropylphosphido) scandium; [1,2-diethylpropylene-(3-methylpentyl, isohexyl-TACN) (2-propylcyclopentadienyl)] (methyl) (ethyl(triethylsilyl))yttrium; [1,2-dimethyl-propylene-(phenyl, methyl-TACN) (1-chloro-2,3,4-trimethylfluorenyl)] (isopropoxy) (butyl) yttrium; [1-methyl-2-ethyl-propylene-(methyl, heptyl-TACN) (cyclopentadienyl)] (pentyl) (dimethylamido) praseodymium; [1,1-methyl-2-isopropyl-propylene-(ethyl, propyl-TACN) (perfluorofluorenyl)] (methyl (triethylsilyl)) (phenoxy) lutetium; [1-methyl-2-phenyl-propylene-(dimethyl-TACN) (ethylamido)] (ethyl (triethylsilyl)) (hexoxy) yttrium; [1-methyl-2-propyl-propylene-(methyl, hexyl-TACN) (perfluorofluorenyl)] (ethoxy) (2-methy-4-ethylphenoxy) lanthanum; [1-phenyl-2-methyl-propylene-(butyl, isohexyl-TACN) (indenyl)] (propoxy) (t-butoxy) yttrium; [1-phenyl-2-methyl-propylene-(ethyl, isopropyl-TACN) (methylamido)] (methylethylphosphido) (methyl(trimethylsilyl)) praseodymium; [1,2-dipentyl-propylene-(ethyl, methyl(triethylsilyl)-TACN) (t-butylphosphido)] (propoxy) (methyl(triethylsilyl)) scandium; [1-methyl-2-ethyl-propylene-(ethyl, methyl-TACN) (phenylamido)] (t-butyl) (ethoxy) lutetium; [1,3-diisopropyl-propylene-(hexyl, propyl-TACN) (t-butylphosphido)] (methylpropylphosphido) (phenyl) samarium; [1-methyl-3-isopropyl-propylene-(methyl, isopropyl-TACN) (cyclopentadienyl) (heptyl) (methyl(trimethylsilyl))europium; [1-methyl-3-phenyl-propylene-(methyl, butyl-TACN) (ethylamido)] (ethyl) (phenylethylamido) erbium; [1-ethyl-3-methyl-propylene-(3-methylpentyl, ethyl-TACN) (fluorenyl)] (methyl) (isohexyl) yttrium; [1-ethyl-3-isopropyl-propylene-(isopropyl, isopentyl-TACN) (perfluorofluorenyl)] (ethoxy) (phenylethylamido) terbium; [1-methyl-3-phenyl-propylene-(ethyl, isopropyl-TACN) (perfluorocyclopentadienyl)] (pentyl) (hexyl) yttrium; [1,3-diethyl-propylene-(methyl, propyl-TACN) (t-butylamido)] (methylnonylphosphido) (phenylethylamido) yttrium; [1-ethyl-3-hexyl-propylene-(diisopentyl-TACN) (2,4,5,7-tetraphenylfluorenyl)] (ethoxy) (isopentoxy) yttrium; [1,3-diphenyl-propylene-(diisopropyl-TACN) (2,4-dimethyl-6-phenylindenyl)] (hexyl) (phenoxy) yttrium; [1-methyl-3-propyl-propylene-(methyl(trimethylsilyl), methyl-TACN) (t-butylphosphido)] (3-methylpentyl) (butoxy) cerium; [1-butyl-3-methyl-propylene-(t-butyl, ethyl-TACN) (cyclopentadienyl)] (hexoxy) (dimethylamido) lanthanum; [1-isopropyl-3-methyl-propylene-(dimethyl-TACN) (methylamido)] (t-butoxy) (3.5-dimethylphenoxy) scandium; [1-propyl-3-methyl-propylene-(dimethyl(triethylsilyl)-TACN) (isopropylamido)] (heptyl) (isopentyl) erbium; [1-pentyl-3-methyl-propylene-(heptyl, isopropyl-TACN) (methylamido)] (methylpropylamido) (phenylethylphosphido) scandium; [1,3-diethyl-propylene-(dipropyl-TACN) (3,5-2,3-dibromoindenyl)] (methylpropylamido)

(isohexyl) samarium; [1-methyl-3-methyl-propylene-(diethyl-TACN) (fluorenyl)] (methyl(triethylsilyl)) (methylpropylphosphido) yttrium.

Representative Examples of TACN-Based Catalyst Precursors

[1-ethyl-1-methyl-butylene-(ethyl, pentyl-TACN) (ethylamido)] (phenylethylamido) (isopropyl) yttrium; [1-pentyl-1-butyl-butylene-(isopropyl, ethyl-TACN) (methylphosphido)] (hexoxy) (isopropoxy) yttrium; [1-pentyl-1-ethyl-butylene-(methyl, phenyl-TACN) (perfluorofluorenyl)] (methylethylamido) (ethyl(trimethylsilyl))yttrium; [1,1-diisopropyl-ethylene-(ethyl, isopropyl-TACN) (2,3,4-trimethyl-5-ethylcyclopentadienyl)] (ethyl(trimethylsilyl)) (hexyl) yttrium; [1-methyl-1-phenyl-ethylene-(propyl, methyl-TACN) (perfluorocyclopentadienyl)] (isopropoxy) (3-methylpentyl) yttrium; [1-phenyl-1-ethyl-ethylene-(methyl, isopropyl-TACN) (cyclopentadienyl)] (methoxy) (pentyl) yttrium; (1-isopropyl-1-isopentyl-germanylene-(isopentyl, methyl-TACN) (methylphosphido)] (butyl) (isohexyl) yttrium; [1-ethyl-1-phenyl-methylene-(3-methylpentyl, isopropyl-TACN) (1-chloro-2,3,4-trimethyl fluorenyl)] (dimethylphosphido) (methylnonylphosphido) yttrium; [1-isopentyl-1-isopropyl-methylene-(methyl, octyl-TACN) (1-chloro-2,3,4-trimethylfluorenyl)] (methoxy) (isopentoxy) yttrium; [1-pentyl-1-ethyl-methylene-(hexyl, ethyl-TACN) (3,5-2,3-dibromoindenyl)] (ethoxy) (diphenylphosphido) yttrium; [1-propyl-1-ethyl-methylene-(3-methylpentyl, pentyl-TACN) (phenylamido)] (methoxy) (heptyl) yttrium; [1-propyl-1-isopentyl-methylene-(methyl(triethylsilyl), ethyl-TACN) (perfluorofluorenyl)] (phenyl) (heptyl) yttrium; [1,1-dimethylphenylene-(isopropyl, propyl-TACN) (t-butylphosphido)] (dimethylphosphido) (ethyl(trimethylsilyl)) yttrium; [1-propyl-1-phenyl]-propylene-(diethyl-TACN) (perfluorocyclopentadienyl)] (ethoxy) (hexoxy) yttrium; [1-isopentyl-1-butyl-silanylene-(methyl(trimethylsilyl) ethyl-TACN) (3,6-2,3-dibromoindenyl)] (ethyl) (3-methylpentyl) yttrium [1,1-diisopropyl-silanylene-(ethyl(triethylsilyl), octyl-TACN) (t-butylamido)] (methylpropylamido) (methylpropylphosphido) yttrium; [1-isopropyl-1-methyl-silanylene-(ethyl, 3-methylpentyl-TACN) (methylphosphido)] (octyl) (isopentoxy) yttrium; [1,1-dimethylsilanylene-(dimethyl(triethylsilyl)-TACN) (2,4-dimethyl-6-phenylindenyl)] (3,6-dimethylphenoxy) (phenylethylamido) yttrium; [1-methyl-1-phenyl-silanylene-(isopropyl, isopentyl-TACN) (methylphosphido)] (methyl) (methyl(trimethylsilyl))yttrium; [1-phenyl-1-ethyl-silanylene-(methyl(triethylsilyl), propyl-TACN) (methylphosphido)] (propyl) (methoxy) yttrium; [1-phenyl-1-methyl-silanylene-(dimethyl-TACN) (methylphosphido)] (methylnonylphosphido) (phenylethylphosphido) yttrium; [1,1-dipropylsilanylene-(propyl, methyl-TACN) (perfluorocyclopentadienyl)] (hexoxy) (isopropoxy) yttrium; [1-phenyl-1-hexyl-methylene-(isopropyl, methyl-TACN) (phenylphosphido)] (propyl) (phenylethylamido) ytterbium; [1-propyl-1-isopropyl-ethylene-(ethyl, isopropyl-TACN) (2,6-2,3-dibromoindenyl)] (phenyl) (hexoxy) thulium; [1-isopropyl-1-ethyl-ethylene-(isopropyl, propyl-TACN) (cyclopentadienyl)] (diphenylamido) (2-methy-4-ethylphenoxy) terbium; [1,1-dipropylmethylene-(3-methylpentyl, heptyl-TACN) (2,4-dimethyl-6-phenylindenyl)] (phenyl) (methylpropylphosphido) terbium; [1,1-dipropylmethylene-(methyl(triethylsilyl), isopropyl-TACN) (propylamido)] (phenyl) (3-methylpentyl) terbium; [1-butyl-1-isopropyl-ethylene-(isopentyl, methyl(triethylsilyl)-TACN) (cyclopentadienyl)] (methylpropylamido) (methylpropylphosphido) scandium; [1-ethyl-1-butyl-ethylene-(t-butyl, isopropyl-TACN) (2,4,6,7-tetraphenylfluorenyl)] (ethyl(trimethylsilyl)) (isohexyl) scandium; [1-ethyl-1-methyl-methylene-(hexyl, propyl-TACN) (methylamido)] (diphenylphosphido) (3-methylpentyl) scandium; [1-isopropyl-1-isopentyl-methylene-(heptyl, propyl-TACN) (indenyl)] (hexyl) (ethyl) scandium; [1-phenyl-1-isopropyl-methylene-(diethyl(triethylsilyl)-TACN) (propylamido)] (hexyl) (heptyl) scandium; [1-phenyl-1-propyl-methylene-(phenyl, octyl-TACN) (2,4-dimethyl-6-phenylindenyl)] (isopentoxy) (3,6-dimethylphenoxy) scandium; [1-phenyl-1-propyl-propylene-(3-methylpentyl, hexyl-TACN) (1-bromo-2,3,4-trimethylindenyl)] (3-methylpentyl) (3,5-dimethylphenoxy) scandium; [1-ethyl-1-isopropyl-silanylene-(ethyl, propyl-TACN) (tetramethycyclopentadienyl)] (phenyl) (3,4-dimethylphenoxy) scandium; [1-methyl-1-ethyl-silanylene-(heptyl, methyl(triethylsilyl)-TACN) (isopropylamido)] (diphenylphosphido) (butyl) scandium; [1-phenyl-1-isopropyl-silanylene-(methyl, propyl-TACN) (methylamido)] (dimethylphosphido) (phenyl) scandium; [1-propyl-1-methyl-silanylene-(propyl, octyl-TACN) (1-chloro-2,3,4-trimethylfluorenyl)] (methylethylphosphido) (ethoxy) scandium; [1,1-hexyl-1-methyl-ethylene-(isopropyl, hexyl-TACN) (2,4-dimethyl-6-phenylindenyl)] (butoxy) (heptyl) samarium; [1-hexyl-1-ethyl-methylene-(isohexyl, methyl (triethylsilyl)-TACN) (cyclopentadienyl)] (diphenylphosphido) (pentyl) samarium; [1-isopropyl-1-methyl-methylene-(methyl(triethylsilyl), phenyl-TACN) (methylphosphido)] (iso-hexyl) (ethyl(triethylsilyl))neodymium; [1-isopropyl-1-ethyl-methylene-(methyl, t-butyl-TACN) (propylamido)] (pentoxy) (octyl) lutetium; [1,1-diethyl-methylene-(hexyl, ethyl-TACN) (phenylamido)] (dimethylamido) (hexoxy) lanthanum; [1-ethyl-1-propyl-methylene-(heptyl, ethyl(triethylsilyl)-TACN) (1-bromo-2, 3,4-trimethylindenyl)] (butoxy) (pentoxy) lanthanum; [1-phenyl-1-butyl-methylene-(methyl, butyl-TACN) (t-butylphosphido)] (dimethylphosphido) (2,6-dimethylphenoxy) lanthanum; [1-ethyl-1-methyl-propylene-(propyl, phenyl-TACN) (perfluorofluorenyl)] (ethyl(triethylsilyl)) (2,5-dimethylphenoxy) lanthanum; [1-ethyl-1-propyl-silanylene-(dipropyl-TACN) (isopropylamido)] (phenoxy) (methylethylphosphido) lanthanum; [1-ethyl-1-methyl-methylene-(propyl, methyl-TACN) (perfluorocyclopentadienyl)] (pentoxy) (butoxy) europium; [1-isopropyl-1-phenyl-phenylene-(t-butyl, methyl(triethylsilyl)-TACN) (2,4,6,7-tetraphenylfluorenyl)] (methyl(trimethylsilyl)) (methylethylamido) europium: [1-ethyl-1-phenyl-methylene-(propyl, ethyl-TACN) (1-chloro-2,3,4-trimethyl fluorenyl)] (diphenylamido) (phenylethylamido) erbium.

Methylenyl-Bridged, TAH Catalyst Precursors

[1-hexyl-1-ethyl-methylene-(ethyl, isopropyl-TAH) (t-butylphosphido)] (phenylethylphosphido) (hexyl) yttrium; [1-isopentyl-1-propyl-methylene-(ethyl, propyl-TAH) (phenylamido)] (methoxy) (heptyl) yttrium; [1-isopropyl-1-methyl-methylene-(propyl, phenyl-TAH) (2,3,4-trimethyl-5-ethylcyclopentadienyl)] (methyl) (methylnonylphosphido) yttrium; [1-methyl-1-isopropyl-methylene-(propyl, ethyl-TAH) (1-bromo-2,3,4-trimethylindenyl)] (ethyl(triethylsilyl)) (hexyl) yttrium; [1,1-methyl-1-phenyl-methylene-(isopentyl, ethyl(triethylsilyl)-TAH) (2,3,6,7-tetraphenylfluorenyl)] (phenoxy) (methyl) yttrium; [1-pentyl-1-propyl-methylene-(propyl, ethyl-TAH) (tetramethycyclopentadienyl)] (methyl(triethylsilyl)) (dimethylamido) yttrium; [1-phenyl-1-methyl-methylene-(ethyl, isohexyl-TAH) (2,4-dimethyl-6-phenylindenyl)] (dimethylphosphido) (t-butyl) yttrium; [1-propyl-1-ethyl-methylene-(diethyl(trimethylsilyl)-TAH) (propylamido)] (2-methy-4-ethylphenoxy) (2-methy-4-ethylphenoxy)

yttrium; [1-propyl-1-isopentyl-methylene-(octyl, methyl-TAH) (methylphosphido)] (ethoxy) (ethyl(triethylsilyl))yttrium; [1,1-dipropylmethylene-(3-methylpentyl, ethyl-TAH) (1-chloro-2,3,4-trimethylfluorenyl)] (methyl(trimethylsilyl)) (isopentyl) yttrium; [1-isopropyl-1-pentyl-methylene-(heptyl, propyl-TAH) (5,6-2,3-dibromoindenyl)] (t-butyl) (isopropoxy) ytterbium; [1-isopropyl-1-ethyl-methylene-(isopentyl, 3-methylpentyl-TAH) (fluorenyl)] (phenoxy) (octyl) thulium; [1-phenyl-1-methyl-methylene-(propyl, methyl-TAH) (2-propylcyclopentadienyl)] (isohexyl) (hexyl) thulium; [1-isopropyl-1-methyl-methylene-(ethyl, isopropyl-TAH) (phenylamido)] (methylnonylphosphido) (methylethylamido) terbium; [1-isopentyl-1-propyl-methylene-(diisopropyl-TAH) (2,3-dibromoindenyl)] (2-methy-4-ethylphenoxy) (isopentoxy) scandium; [1-phenyl-1-propyl-methylene-(di-t-butyl-TAH) (methylamido)] (phenylethylphosphido) (heptyl) scandium; [1-propyl-1-methyl-methylene-(methyl, butyl-TAH) (perfluorofluorenyl)] (octyl) (isopentoxy) scandium; [1-hexyl-1-isopropyl-methylene-(dipropyl-TAH) (methylphosphido)] (propoxy) (methylnonylphosphido) praseodymium; [1-methyl-1-ethyl-methylene-(propyl, heptyl-TAH) (t-butylamido)] (isohexyl) (pentoxy) neodymium; [(1-methyl-1-ethyl-methylene-(ethyl, isopropyl-TAH) (perfluorofluorenyl)] (phenylethylphosphido) (methyl) lutetium; [1-propyl-1-ethyl-methylene-(hexyl, ethyl-TAH) (phenylphosphido)] (t-butyl) (phenylethylphosphido) lutetium; [1-phenyl-1-ethyl-methylene-(ethyl, methyl-TAH) (2,3-dibromoindenyl)] (dibutyl) lanthanum; [1-phenyl-1-propyl-methylene-(ethyl(trimethylsilyl), propyl-TAH) (phenylamido)] (methylpropylphosphido) (phenylethylphosphido) gadolinium; [1-isopropyl-1-propyl-methylene-(propyl, methyl(trimethylsilyl)-TAH) (phenylamido)] (methylpropylamido) (methyl) erbium; [1-isopropyl-1-phenyl-methylene-(dimethyl-TAH) (tetramethycyclopentadienyl)] (phenyl) (methylpropylphosphido) dysprosium;

Silanylene-Bridged, TAH Catalyst Precursors

[1-ethyl-1-phenyl-silanylene-(methyl, pentyl-TAH) (1-bromo-2, 3, 4-trimethylindenyl)] (pentoxy) (diphenylamido) yttrium; [1-methyl-1-isopropyl-silanylene-(phenyl, ethyl-TAH) (1-chloro-2,3,4-trimethylfluorenyl)] (diphenylphosphido) (hexyl) yttrium; [1,1-dimethylsilanylene-(ethyl, phenyl-TAH) (1-chloro-2,3,4-trimethylfluorenyl)] (propoxy) (butoxy) yttrium; [1-methyl-1-pentyl-silanylene-(3-methylpentyl, ethyl-TAH) (2-propylcyclopentadienyl)] (pentyl) (pentyl) yttrium; [1-methyl-1-phenyl-silanylene-(isopropyl, methyl-TAH) (indenyl)] (dimethylphosphido) (t-butyl) yttrium; [1-methyl-1-phenyl-silanylene-(propyl, methyl-TAH) (2,3,6,7-tetraphenylfluorenyl)] (propyl) (2,5-dimethylphenoxy) yttrium; [1-pentyl-1-isopropyl-silanylene-(methyl, 3-methylpentyl-TAH) (perfluorofluorenyl)] (propoxy) (2,4-dimethylphenoxy) yttrium; [1-propyl-1-ethyl-silanylene-(pentyl, methyl-TAH) (cyclopentadienyl)] (ethyl) (isopropoxy) yttrium; [1-propyl-1-methyl-silanylene-(methyl, propyl-TAH) (propylamido)] (t-butoxy) (butoxy) yttrium; [1,1-dipropylsilanylene-(diphenyl-TAH) (2-propylcyclopentadienyl)] (propyl) (ethoxy) yttrium; [1-isopentyl-1-phenyl-silanylene-(isopropyl, t-butyl-TAH) (t-butylphosphido)] (diphenoxy) ytterbium; [1-phenyl-1-propyl-silanylene-(phenyl, isopropyl-TAH) (perfluorofluorenyl)] (propyl) (hexoxy) terbium; [1-propyl-1-isopropyl-silanylene-(propyl, ethyl(trimethylsilyl)-TAH) (perfluorofluorenyl)] (methylpropylamido) (ethyl(trimethylsilyl))terbium; [1-ethyl-1-isopentyl-silanylene-(diisopropyl-TAH) (t-butylamido)] (hexyl) (phenoxy) scandium; [1-isopropyl-1-ethyl-silanylene-(propyl, ethyl(trimethylsilyl)-TAH) (2,4-dimethyl-6-phenylindenyl)] (2-methy-4-ethylphenoxy) (methylnonylphosphido) scandium; [1-pentyl-1-propyl-silanylene-(isopropyl, methyl(triethylsilyl)-TAI-I) (perchloroindenyl)] (ethylpentylphosphido) (methylpropylphosphido) scandium; [1-phenyl-1-butyl-silanylene-(ethyl, propyl-TAH) (perfluorofluorenyl)] (hexoxy) (butoxy) scandium; [1-propyl-1-ethyl-silanylene-(isopropyl, methyl-TAH) (perfluorocyclopentadienyl)] (methylpropylamido) (methylpropylamido) scandium; [1-methyl-1-propylsilanylene-(butyl, isopropyl-TAH) (1-bromo-2,3,4-trimethylindenyl)] (phenyl) (diphenylamido) samarium; [1-isopentyl-1-propyl-silanylene-(isohexyl, methyl-TAH) (1-bromo-2,3,4-trimethylindenyl)] (phenylethylamido) (ethylpentylphosphido) praseodymium; [1-butyl-1-propyl-silanylene-(octyl, methyl-TAH) (2,3,4-trimethyl-5-ethylcyclopentadienyl)] (methylethylamido) (octyl) lutetium; [1-methyl-1-ethyl-silanylene-(propyl, t-butyl-TAH) (methylamido)] (isopropoxy) (ethyl(triethylsilyl))lanthanum; [1-isopropyl-1-propylsilanylene-(methyl, t-butyl-TAI-I) (perchloroindenyl)] (hexyl) (methylnonylphosphido) gadolinium; [1-propyl-1-phenyl-silanylene-(methyl(trimethylsilyl), ethyl-TAH) (isopropylamido)] (phenylethylphosphido) (octyl) gadolinium; [1-ethyl-1-isopropyl-silanylene-(methyl, isopropyl-TAH) (indenyl)] (methyl(triethylsilyl)) (ethyl(trimethylsilyl))cerium.

Germanylene-Bridged, TAH Catalyst Precursors

[1-ethyl-1-methyl-germanylene-(dimethyl(triethylsilyl)-TAH) (propylamido)] (diphenylamido) (methyl) yttrium; [1-isopentyl-1-propylgermanylene-(hexyl, ethyl(triethylsilyl)-TAH) (ethylamido)] (dimethylphosphido) (methylpropylphosphido) yttrium; [1, 1-diisopropylgermanylene-(ethyl, propyl-TAH) (perchloroindenyl)] (isopentyl) (methyl) yttrium; [1,1-diisopropyl-germanylene-(hexyl, pentyl-TAH) (cyclopentadienyl)] (isopentyl) (t-butyl) yttrium; [1-isopropyl-1-methyl-germanylene-(ethyl(triethylsilyl), methyl(triethylsilyl)-TAH) (perfluorofluorenyl)] (ethoxy) (3-methylpentyl) yttrium; [1, 1-dimethylgermanylene-(phenyl, isopropyl-TAH) (propylamido)] (methyl(trimethylsilyl)) (phenoxy) yttrium; [1-methyl-1-propyl-germanylene-(diethyl-TAH) (ethylamido)] (isopentyl) (ethyl(trimethylsilyl)) yttrium; [1-methyl-1-propyl-germanylene-(dimethyl-TAH) (propylamido)] (methylnonylphosphido) (isopentoxy) yttrium; [1-pentyl-1-isopropyl-germanylene-(ethyl(trimethylsilyl), ethyl-TAI-I) (ethylamido)] (methylpropylphosphido) (phenyl) yttrium; [1-phenyl-1-ethyl-germanylene-(isopentyl, ethyl(trimethylsilyl)-TAH) (fluorenyl)] (propyl) (phenylethylphosphido) yttrium; [1-phenyl-1-isopropyl-germanylene-(methyl, t-butyl-TAH) (cyclopentadienyl)] (pentyl) (ethyl(trimethylsilyl))yttrium; [1-phenyl-1-methyl-germanylene-(diethyl(triethylsilyl)-TAH) (ethylamido)] (methyl) (ethyl) yttrium; [1,2-diphenylgermanylene-(3-methylpentyl, propyl-TAH) (2,3-dibromoindenyl)] (ethyl(trimethylsilyl)) (t-butyl) yttrium; [1-phenyl-1-propylgermanylene-(isopentyl, propyl-TAH) (t-butylamido)] (ethyl (trimethylsilyl)) (ethyl(triethylsilyl))yttrium; [1-propyl-1-butyl-germanylene-(ethyl(trimethylsilyl), ethyl-TAH) (propylamido)] (t-butyl) (ethyl(trimethylsilyl))yttrium; [1-propyl-1-ethyl-germanylene-(propyl, hexyl-TAH) (methylphosphido)] (2-methy-4-ethylphenoxy) (pentoxy) yttrium; [1-isopropyl-1-ethyl-germanylene-(dimethyl(triethylsilyl)-TAH) (t-butylamido)] (methylethylamido) (ethylpentylphosphido) scandium; [1-propyl-1-butyl-germanylene-(methyl (triethylsilyl), propyl-TAH) (methylamido)] (diphenylphosphido) (ethyl) scandium; [1-methyl-1-isopropyl-germanylene-(dipropyl-TAH) (2,4-dimethyl-6-phenylindenyl)] (propyl) (ethyl) praseodymium; [1-ethyl-1-isopropylgermanylene-(dimethyl-TAH) (1-bromo-2,3,4- trimethylindenyl)] (dimethylamido) (propoxy) lutetium; [1-isopentyl-1-ethyl-germanylene-(octyl, propyl-TAH) (indenyl)] (hexyl) (methyl(trimethylsilyl))lanthanum; [1-isopropyl-1-hexyl-germanylene-(isopropyl, propyl-TAH) (perfluorofluorenyl)] (isopropoxy) (isopropyl) lanthanum; [1-propyl-1-phenyl-germanylene-(3-methylpentyl, isopentyl-TAH) (perfluorofluorenyl)] (dimethylphosphido) (methyl (trimethylsilyl))gadolinium; [1-propyl-1-methyl-germanylene-(hexyl, ethyl-TAM) (t-butylamido)] (diphenylamido) (phenyl) europium; [1-methyl-1-pentyl-germanylene-(propyl, isohexyl-TAM) (2,3,4-trimethyl-5-ethylcyclopentadienyl)] (ethyl(triethylsilyl)) (phenylethylamido) cerium.

Ethylenyl-Bridged, TAH Catalyst Precursors

[1-ethyl-1-propyl-ethylene-(methyl, isopropyl-TAH) (ethylamido)] (methyl(trimethylsilyl)) (isopropyl) yttrium; [1,1-dimethylethylene-(isopropyl, ethyl-TAH) (t-butylphosphido)] (ethoxy) (methyl(trimethylsilyl))yttrium; [1pentyl-1-methyl-ethylene-(ethyl(triethylsilyl), phenyl-TAH) (propylamido)] (methyl) (heptyl) yttrium; [1-phenyl-]-butyl-ethylene-(isohexyl, isopentyl-TAH) (1-chloro-2,3,4-trimethylfluorenyl)) (isopropoxy) (ethyl) yttrium; [1,2-diphenylethylene-(ethyl, methyl-TAH) (perchloroindenyl)] (methyl) (dimethylamido) yttrium; [1-propyl-1-isopropyl-ethylene-(ethyl, propyl-TAH) (perchloroindenyl)] (ethylpentylphosphido) (phenyl) yttrium; [1-propyl-1-phenyl-ethylene-(dimethyl(triethylsilyl)-TAH) (cyclopentadienyl)] (isohexyl) (methoxy) yttrium; [1,1-diethyl-ethylene-(ethyl(triethylsilyl), ethyl-TAH) (1-bromo-2,3,4-trimethylindenyl)] (ethyl(triethylsilyl)) (dimethylphosphido) scandium; [1-ethyl-1-pentyl-ethylene-(diethyl-TAH) (perfluorocyclopentadienyl)] (dimethylphosphido) (diphenylamido) scandium; [1-isopropyl-1-phenyl-ethylene-(ethyl, hexyl-TAH) (t-butylamido)] (propoxy) (diphenylphosphido) scandium; [1-methyl-2-isopropyl-ethylene-(methyl, octyl-TAH) (t-butylphosphido)] (t-butyl) (ethylpentylphosphido) scandium; [1,2-dimethyl-ethylene-(diethyl-TAH) (3,4,5,6-tetraphenylfluorenyl)] (methylethylphosphido) (hexyl) yttrium; [1,1-diisopropyl-ethylene-(ethyl, t-butyl-TAH) (t-butylamido)] (methylpropylamido) (methylethylamido) neodymium; [1-methyl-2-propyl-ethylene-(methyl, isopentyl-TAH) (tetramethycyclopentadienyl)] (pentoxy) (methylpropylamido) scandium; [1-ethyl-2-isopropyl-ethylene-(isopropyl, isohexyl-TAH) (fluorenyl)] (diphenylphosphido) (ethylpentylphosphido) terbium; [1-ethyl-2-phenyl-ethylene-(ethyl (triethylsilyl), methyl-TAH) (phenylphosphido)] (t-butoxy) (methylethylamido) lutetium; [1-isopropyl-1-propyl-ethylene-(pentyl, ethyl-TAH) (2,3,4-trimethyl-5-ethylcyclopentadienyl)] (dimethylamido) (hexoxy) lutetium; [1,1-diisopropyl-ethylene-(3-methylpentyl, isopropyl-TAH) (methylphosphido)] (phenoxy) (heptyl) lanthanum; [1,2-dimethyl-ethylene-(3-methylpentyl, ethyl(triethylsilyl)-TAH) (perfluorofluorenyl)] (methylethylamido) (phenyl) praseodymium; [1,2-diethylethylene-(isopropyl, methyl(triethylsilyl)-TAH) (2,3,4-trimethyl-5-ethylcyclopentadienyl)] (ethyl) (hexyl) yttrium; [1,2-diphenylethylene-(isopropyl, ethyl-TAH) (indenyl)] (butoxy) (phenylethylamido) erbium; [1-propyl-2-ethyl-ethylene-(propyl, ethyl(trimethylsilyl)-TAH) (t-butylamido)] (methylethylamido) (2,4-dimethylphenoxy) scandium; [1-ethyl-1-phenyl-ethylene-(isopropyl, octyl-TAH) (indenyl)] (methylpropylphosphido) (methyl(triethylsilyl))dysprosium; [1-phenyl-2-ethyl-ethylene-(isopropyl, hexyl-TAH) (tetramethycyclopentadienyl)] (hexoxy) (isopentyl) lanthanum, [1,1-diethyl-ethylene-(pentyl, propyl-TAH) (2-propylcyclopentadienyl)] (pentyl) (ethylpentylphosphido) yttrium; [1-ethyl-2-methyl-ethylene-(isohexyl, methyl(trimethylsilyl)-TAH) (perfluorofluorenyl)] (t-butyl) (hexyl) yttrium; [1-ethyl-2-phenyl-ethylene-(isopropyl, propyl-TAH) (2,4-dimethyl-6-phenylindenyl)] (isopropoxy) (hexoxy) yttrium; [1-ethyl-2-phenyl-ethylene-(t-butyl, methyl-TAH) (perfluorofluorenyl)] (diphenylphosphido) (methyl(trimethylsilyl))yttrium; [1-isopropyl-2-methyl-ethylene-(ethyl, methyl-TAH) (phenylphosphido)] (methylpropylamido) (ethoxy) holmium; [1-isopropyl-2-methyl-ethylene-(t-butyl, methyl(trimethylsilyl)-TAR) (3,4,5,6-tetraphenylfluorenyl)] (methylethylamido) (methyl(triethylsilyl))dysprosium; [1-phenyl-2-isopentyl-ethylene-(ethyl, propyl-TAH) (2-propylcyclopentadienyl)] (dimethylamido) (ethoxy) yttrium; [1-phenyl-2-propyl-ethylene-(ethyl, isohexyl-TAH) (2,3-dibromoindenyl)] (pentoxy) (ethyl(triethylsilyl))yttrium.

Propylenyl-Bridged, TAH Catalyst Precursors

[1-phenyl-1-ethyl-propylene-(octyl, methyl-TAH) (2,3-dibromoindenyl)] (methylpropylamido) (2-methy-4-ethylphenoxy) yttrium; [1-propyl-1-phenyl-propylene-(dimethyl-TAH) (2-propylcyclopentadienyl)] (ethyl) (t-butyl) yttrium; [1-pentyl-1-propyl-propylene-(diethyl-TAH) (perfluorofluorenyl)] (phenyl) (methylnonylphosphido) lanthanum; [1-isopropyl-1-methyl-propylene-(propyl, octyl-TAH) (perchloroindenyl)] (phenylethylamido) (propoxy) neodymium; [1,2-diphenylpropylene-(diethyl-TAH) (indenyl)] (hexyl) (phenylethylphosphido) yttrium; [1-propyl-1-isopropyl-propylene-(ethyl, methyl-TAH) (2-propylcyclopentadienyl)] (isopentoxy) (methylethylamido) yttrium; [1-isopropyl-1-ethyl-propylene-(isopropyl, isopentyl-TAI-I) (phenylphosphido)] (isopentyl) (diphenylamido) scandium; [1-phenyl-1-ethyl-propylene-(isopropyl, 3-methylpentyl-TAH) (perfluorofluorenyl)] (ethyl) (methyl) lanthanum; [1-propyl-1-methyl-propylene-(methyl, octyl-TAH) (cyclopentadienyl)] (phenoxy) (2,4-dimethylphenoxy) neodymium; [1-ethyl-1-phenyl-propylene-(methyl(trimethylsilyl), isopropyl-TAH) (fluorenyl)] (3-methylpentyl) (heptyl) yttrium [1,1-dimethylpropylene-(t-butyl phenyl-TAH) (indenyl)] (butoxy) (ethoxy) scandium; [1-isopropyl-1-ethyl-propylene-(ethyl, isopropyl-TAH) (2,4-dimethyl-6-phenylindenyl)] (isohexyl) (butoxy) yttrium; [1-butyl-2-methyl-propylene-(methyl(triethylsilyl), methyl-TAH) (phenylphosphido)] (hexoxy) (dimethylamido) ytterbium; [1-propyl-2-ethyl-propylene-(methyl, heptyl-TAH) (phenylphosphido)] (methylnonylphosphido) (phenylethylamido) yttrium; [1-isopropyl-2-methyl-propylene-(diethyl-TAH) (2,3,4-trimethyl-5-ethylcyclopentadienyl)] (isohexyl) (ethyl) lanthanum; [1-propyl-2-isopentyl-propylene-(methyl, isopentyl-TAH) (methylamido)] (butyl) (hexyl) yttrium; [1,2-dimethyl-propylene-(pentyl propyl-TAH) (perfluorofluorenyl)] (methylnonylphosphido) (methylpropylphosphido) scandium; [1,2-diethylpropylene-(3-methylpentyl, isohexyl-TAH) (2-propylcyclopentadienyl)] (methyl) (ethyl (triethylsilyl))yttrium; [1,2-dimethyl-propylene-(phenyl, methyl-TAH) (1-chloro-2,3,4-trimethylfluorenyl)] (isopropoxy) (butyl) yttrium; [1-methyl-2-ethyl-propylene-(methyl, heptyl-TAH) (cyclopentadienyl)] (pentyl) (dimethylamido) praseodymium; [1-methyl-2-isopropyl-propylene-(ethyl, propyl-TAH) (perfluorofluorenyl)] (methyl(triethylsilyl)) (phenoxy) lutetium; [1-methyl-2-phenyl-propylene-(dimethyl-TAH) (ethylamido)] (ethyl(triethylsilyl)) (hexoxy) yttrium; [1-methyl-2-propyl-propylene-(methyl, hexyl-TAH) (perfluorofluorenyl)] (ethoxy) (2-methy-4-ethylphenoxy) lanthanum; [1-phenyl-2-methyl-propylene-(butyl, isohexyl-TAH) (indenyl)] (propoxy) (t-butoxy) yttrium; [1-phenyl-2-methyl-propylene-(ethyl, isopropyl-TAH) (methylamido)] (methylethylphosphido) (methyl(trimethylsilyl))praseodymium; [1,2-dipentyl-propylene-(ethyl, methyl (triethylsilyl)-TAH) (t-butylphosphido)] (propoxy) (methyl (triethylsilyl))scandium; [1-methyl-2-ethyl-propylene-(ethyl, methyl-TAH) (phenylamido)] (t-butyl) (ethoxy) lutetium; [1,3-diisopropyl-propylene-(hexyl, propyl-TAH) (t-butylphosphido)] (methylpropylphosphido) (phenyl) samarium, [1-methyl-3-isopropyl-propylene-(methyl, isopropyl-TAH) (cyclopentadienyl)] (heptyl) (methyl(trimethylsilyl))europium; [1-methyl-3-phenyl-propylene-(methyl, butyl-TAH) (ethylamido)] (ethyl) (phenylethylamido) erbium: [1-ethyl-3-methyl-propylene-(3-methylpentyl, ethyl-TAH) (fluorenyl)] (methyl) (isohexyl) yttrium; [1-ethyl-3-isopropyl-propylene-(isopropyl, isopentyl-TAH) (perfluorofluorenyl)] (ethoxy) (phenylethylamido) terbium; [1-methyl-3-phenyl-propylene-(ethyl, isopropyl-TAH) (perfluorocyclopentadienyl)] (pentyl) (hexyl) yttrium; [1,3-diethyl-propylene-(methyl, propyl-TAH) (t-butylamido)] (methylnonylphosphido) (phenylethylamido) yttrium; [1-ethyl-3-hexyl-propylene-(diisopentyl-TAH) (3,4,5,6-tetraphenylfluorenyl)] (ethoxy) (isopentoxy) yttrium; [1,3-diphenyl-propylene-(diisopropyl-TAH) (2,4-dimethyl-6-phenylindenyl)] (hexyl) (phenoxy) yttrium; [1-methyl-3-propyl-propylene-(methyl(trimethylsilyl), methyl-TAH) (t-butylphosphido)] (3-methylpentyl) (butoxy) cerium; [1-butyl-3-methyl-propylene-(t-butyl, ethyl-TAH) (cyclopentadienyl)] (hexoxy) (dimethylamido) lanthanum; [1-isopropyl-3-methyl-propylene-(dimethyl-TAH) (methylamido)] (t-butoxy) (2,4-dimethylphenoxy) scandium; [1-propyl-3-methyl-propylene-(dimethyl(triethylsilyl)-TAH) (isopropylamido)] (heptyl) (isopentyl) erbium; [1-pentyl-3-methyl-propylene-(heptyl, isopropyl-TAH) (methylamido)] (methylpropylamido) (phenylethylphosphido) scandium; [1,3-diethyl-propylene-(dipropyl-TAH) (2,3-dibromoindenyl)] (methylpropylamido) (isohexyl) samarium; [1-methyl-3-methyl-propylene-(diethyl-TAH) (fluorenyl)] (methyl(triethylsilyl)) (methylpropylphosphido) yttrium.

Representative Examples of TAH-Based Catalyst Precursors

[1-propyl-1-isopropyl-ethylene-(ethyl(trimethylsilyl), methyl-TAH) (2,4-dimethyl-6-phenylindenyl)] (hexyl) (phenylethylamido) yttrium; [1-isopropyl-1-propyl-germanylene-(ethyl, 3-methylpentyl-TAH) (2-propylcyclopentadienyl)] (ethyl) (methylethylamido) yttrium; [1-methyl-1-propylgermanylene-(dimethyl-TAH) (t-butylphosphido)] (diphenylamido) (ethoxy) yttrium; [1-isopropyl-1-phenyl-methylene-(t-butyl, ethyl(triethylsilyl)-TAH) (2-propylcyclopentadienyl)] (ethoxy) (ethyl(trimethylsilyl))yttrium; [1,1-dimethylmethylene-(isopropyl, propyl-TAH) (phenylamido)] (phenyl) (dimethylamido) yttrium; [1-phenyl-1-ethyl-methylene-(diethyl-TAH) (perfluorocyclopentadienyl)] (methylethylphosphido) (methyl) yttrium; [1-phenyl-1-propyl-methylene-(ethyl propyl-TAH) (perfluorofluorenyl)] (t-butyl) (ethyl(trimethylsilyl))yttrium; [1-propyl-1-phenyl-methylene-(isopropyl, methyl-TAH) (phenylphosphido)] (phenyl) (propoxy) yttrium; [1-propyl-1-phenyl-methylene-(methyl, propyl-TAH) (t-butylamido)] (hexyl) (phenoxy) yttrium; [1,1-diisopropyl-phenylene-(3-methylpentyl, 3-methylpentyl-TAH) (isopropylamido)] (pentyl) (methylethylphosphido) yttrium; [1,1-dimethylphenylene-(heptyl methyl(triethylsilyl)-TAH) (tetramethycyclopentadienyl)] (butoxy) (methyl(trimethylsilyl))yttrium; [1,1-dipropylphenylene-(3-methylpentyl, heptyl-TAH) (phenylamido)] (isopentyl) (ethyl) yttrium; [1-butyl-1-phenyl-silanylene-(3-methylpentyl, methyl-TAH) (1-chloro-2,3,4-trimethylfluorenyl)] (dimethylphosphido) (ethyl (trimethylsilyl))yttrium; [1-isopropyl-1-propyl-silanylene-(propyl, ethyl(trimethylsilyl)-TAH) (3,4,5,6-tetraphenylfluorenyl)] (methyl(triethylsilyl)) (phenylethylamido) yttrium; [1-methyl-1-ethyl-silanylene-(pentyl, methyl(trimethylsilyl)-TAH) (fluorenyl)] (ethylpentylphosphido) (butoxy) yttrium; [1-methyl-1-pentyl-silanylene-(methyl, isopropyl-TAH) (perfluorofluorenyl)] (ethyl (trimethylsilyl)) (propyl) yttrium; [1-pentyl-1-methyl-silanylene-(ethyl, butyl-TAH) (methylamido)] (dimethylamido) (2-methy-4-ethylphenoxy) yttrium; [1-pentyl-1-methyl-silanylene-(isopropyl, ethyl-TAH) (perchloroindenyl)] (ethylpentylphosphido) (methylpropylamido) yttrium; [1-phenyl-1-methyl-silanylene-(t-butyl, isopentyl-TAH) (2,3,4-trimethyl-5-ethylcyclopentadienyl)] (ethyl) (diphenylphosphido) yttrium; [1-propyl-1-ethyl-silanylene-(ethyl, 3-methylpentyl-TAH) (methylphosphido)] (isopentoxy) (ethylpentylphosphido) yttrium; [1-propyl-1-methyl-silanylene-(octyl, propyl-TAH) (perfluorofluorenyl)] (methyl) (isopentyl) yttrium; [1-propyl-1-isopropyl-methylene-(isopropyl, ethyl-TAH) (ethylamido)] (methoxy) (ethyl (trimethylsilyl))ytterbium; [1-isopropyl-1-phenyl-silanylene-(methyl, propyl-TAH) (3,4,5,6-tetraphenylfluorenyl)] (phenoxy) (isopentoxy) ytterbium; [1-methyl-1-propyl-phenylene-(butyl, ethyl-TAH) (1-bromo-2,3,4-trimethylindenyl)] (dimethylphosphido) (ethyl) thulium; [1-methyl-1-isopropyl-silanylene-(dipropyl-TAH) (2,3,4-trimethyl-5-ethylcyclopentadienyl)] (ethyl) (methyl(triethylsilyl))thulium; (1-ethyl-1-isopropyl-silanylene-(isopropyl, methyl(trimethylsilyl)-TAH) (methylamido)] (methylnonylphosphido) (2-methy-4-ethylphenoxy) terbium; [1-isopropyl-1-methyl-ethylene-(ethyl, t-butyl-TAH) (1-bromo-2,3,4-trimethylindenyl)] (isohexyl) (2,4-dimethylphenoxy) scandium; [1-ethyl-1-propyl-methylene-(heptyl, t-butyl-TAH) (2-propylcyclopentadienyl)] (dimethylphosphido) (ethyl) scandium; [1-isopentyl-1-ethyl-methylene-(t-butyl, propyl-TAH) (tetramethycyclopentadienyl)] (isopropyl) (methylethylamido) scandium; [1-methyl-1-pentyl-methylene-(isopropyl, methyl(triethylsilyl)-TAH) (propylamido)] (isopentoxy) (pentyl) scandium; [1-ethyl-1-isopropyl-propylene-(propyl, ethyl-TAH) (tetramethycyclopentadienyl)] (ethoxy) (t-butoxy) scandium; [1-methyl-1-ethyl-propylene-(ethyl(triethylsilyl), propyl-TAH) (2,4-dimethyl-6-phenylindenyl)] (phenyl) (pentoxy) scandium; [1-ethyl-1-phenyl-silanylene-(diethyl-TAH) (phenylphosphido)] (t-butoxy) (heptyl) scandium; [1-phenyl-1-isopropyl-silanylene-(ethyl(triethylsilyl), ethyl-TAH) (tetramethycyclopentadienyl)] (phenylethylphosphido) (isopentyl) scandium; [1-phenyl-1-isopropyl-silanylene-(t-butyl, propyl-TAH) (perchloroindenyl)] (propyl) (methylethylphosphido) scandium; [1,1-dipropylmethylene-(methyl, phenyl-TAH) (methylphosphido)] (hexyl) (butoxy) samarium; [1-butyl-1-phenyl-silanylene-(isopropyl, methyl-TAH) (isopropylamido)] (phenyl) (3,6-dimethylphenoxy) samarium; [1,1-diisopropyl-silanylene-(pentyl, hexyl-TAH) (perfluorofluorenyl)] (phenyl) (methylpropylphosphido) praseodymium; [1,1-dipropylsilanylene-(octyl, butyl-TAH) (propylamido)] (propyl) (diphenylphosphido) praseodymium; [1,1-dimethylmethylene-(diisopropyl-TAH) (perchloroindenyl)] (pentyl) (propyl) lutetium; [1-propyl-1-ethyl-ethylene-(3-methylpentyl, ethyl(trimethylsilyl)-TAH) (2,3,4-trimethyl-5-ethylcyclopentadienyl)] (hexoxy) (phenylethylamido) lanthanum; [1-isopropyl-1-phenyl-methylene-(3-methylpentyl, ethyl-TAH) (perfluorofluorenyl)] (3,6-dimethylphenoxy) (heptyl) lanthanum; [1,1-diethyl-silanylene-(methyl(triethylsilyl), isopropyl-TAH) (phenylamido)] (isopentyl) (hexoxy) lanthanum; [1,1-dipropylmethylene-(ethyl, pentyl-TAH) (2-propylcyclopentadienyl)] (phenylethylamido) (diphenylamido) holmium; [1,2-diphenylsilanylene-(dimethyl-TAH) (isopropylamido)] (ethyl(triethylsilyl)) (methylpropylamido) holmium; [1,1-diethyl-butylene-(propyl, 3-methylpentyl-TAH) (methylamido)] (2-methy-4-ethylphenoxy) (methylpropylphosphido) europium, [1-propyl-1-methyl-methylene-(propyl ethyl(trimethylsilyl)-TAM) (t-butylamido)] (dimethylphosphido) (propoxy) europium; [1-ethyl-1-phenyl-methylene-(phenyl, methyl-TAH) (propylamido)] (isopentyl) (methyl(triethylsilyl))erbium; [1-methyl-1-isopropyl-silanylene-(hexyl, ethyl-TAH) (indenyl)] (hexyl) (phenoxy) erbium; [1,2-diphenylsilanylene-(ethyl, isopentyl-TAH) (cyclopentadienyl)] (methylnonylphosphido) (dimethylamido) scandium.

Representative Catalyst Precursor Examples with Aza-Ligands

Different Diaza-Ligands.

[1,1-diethyl-methylene-(pentyl-DACN) (methylamido)] (hexoxy)(methyl(trimethylsilyl))yttrium; [1-methyl-1-phenyl-methylene-(isopropyl-DACN) (2,4-dimethyl-6-phenylindenyl)] (pentoxy)(phenylethylamido)yttrium; [1,1-dipropylmethylene-(isopropyl-DACN) (fluorenyl)] (propoxy) (propoxy)yttrium; [1-propyl-1-methyl-propylene-(propyl-DACN) (2,3,4-trimethyl-5-ethylcyclopentadienyl)] (3,6-dimethylphenoxy)(t-butoxy)yttrium; [1-ethyl-1-isopropyl-silanylene-(ethyl-DACN) (1-bromo-2,3,4-trimethylindenyl)] (isopropyl)(ethoxy)yttrium; [1-methyl-1-isopropyl-silanylene-(3-methylpentyl-DACN) (t-butylamido)] (t-butoxy)(butoxy)yttrium; [1,1-dipropylsilanylene-(isopropyl-DACN) (t-butylamido)] (butyl)(diphenylamido)yttrium; [1-methyl-1-ethyl-methylene-(isopropyl-DACN) (methylamido)] (t-butoxy)(diphenylphosphido) ytterbium; [1,1-dipropylgermanylene-(methyl-DACN) (perfluorocyclopentadienyl)] (methyl(triethylsilyl))(methylnonylphosphido)scandium; [1-propyl-1-phenyl-silanylene-(hexyl-DACN) (methylphosphido)] (ethyl(trimethylsilyl)) (methylethylamido)praseodymium; [1-butyl-1-methyl-methylene-(ethyl-DACN) (methylphosphido)] (2-methy-4-ethylphenoxy)(t-butoxy)neodymium; [1-methyl-1-ethyl-methylene-(methyl-DACN) (cyclopentadienyl)] (diphenylamido)(ethoxy)lutetium; [1,2-diphenylethylene-(ethyl-DACN) (2,3-dibromoindenyl)] (t-butoxy)(methylethylamido)lanthanum; [1-methyl-1-propyl-methylene-(methyl(trimethylsilyl)-DACN) (phenylamido)] (t-butyl) (ethoxy)lanthanum; [1-propyl-1-ethyl-silanylene-(methyl (trimethylsilyl)-DACN) (2,4-dimethyl-6-phenylindenyl)] (heptyl)(methyl(trimethylsilyl))lanthanum; [1-isopropyl-1-pentyl-methylene-(propyl-DACN) (propylamido)] (phenylethylamido)(ethylpentylphosphido)holmium; [1-isopropyl-1-methyl-methylene-(propyl-DACN) (ethylamido)] (propyl) (3-methylpentyl)gadolinium; [1-propyl-1-ethyl-silanylene-(octyl-DACN) (1-bromo-2,3,4-trimethylindenyl)] (methylpropylamido)(ethyl)europium; [1-isopropyl-1-propyl-methylene-(butyl-DACN) (2,3,4-trimethyl-5-ethylcyclopentadienyl)] (hexyl)(methylethylamido)cerium; [1-ethyl-1-phenyl-methylene-(isopropyl-DACN) (propylamido)] (propyl)(ethylpentylphosphido)erbium;

Different Triaza-Ligands.

[1-methyl-1-butyl-methylene-(propyl, ethyl-TACDD) (t-butylphosphido)] (isohexyl)(ethyl(triethylsilyl))scandium; [1-ethyl-1-phenyl-silanylene-(ethyl, methyl-TACDD) (perfluorocyclopentadienyl)] (ethoxy)(propyl)scandium; [1-methyl-1-phenyl-silanylene-(dipropyl-TACDD) (fluorenyl)] (methylethylamido)(ethyl(trimethylsilyl))scandium; [1-propyl-1-methyl-silanylene-(3-methylpentyl, isohexyl-TACDD) (perchloroindenyl)] (ethyl)(methyl(triethylsilyl)) praseodymium; [1-methyl-1-phenyl-silanylene-(ethyl, 3-methylpentyl-TACDD) (ethylamido)] (methylpropylamido) (hexyl)lanthanum; [1-phenyl-1-ethyl-silanylene-(isohexyl, pentyl-TACDD) (2,3,4-trimethyl-5-ethylcyclopentadienyl)] (methyl(trimethylsilyl))(phenylethylphosphido)dysprosium; [1-isopropyl-1-ethyl-methylene-(heptyl, phenyl-TACDD) (1-bromo-2,3,4-trimethylindenyl)] (isopropyl)(methylpropylamido)yttrium; [1-phenyl-1-isopropyl-methylene-(methyl(trimethylsilyl),isopropyl-TACDD) (phenylphosphido)] (heptyl)(ethylpentylphosphido)yttrium; [1-phenyl-1-isopropyl-silanylene-(methyl, propyl-TACH) (3,4,5,8-tetraphenylfluorenyl)] (isopentoxy)(ethoxy)yttrium; [1-isopropyl-1-isopentyl-methylene-(methyl(trimethylsilyl),ethyl-TACH) (1-bromo-2,3,4-trimethylindenyl)] (propoxy)(propyl)samarium; [1,1-dimethylsilanylene-(ethyl, t-butyl-TACH) (1-chloro-2,3,4-trimethylfluorenyl)] (ethyl)(phenylethylphosphido)neodymium; [1-ethyl-1-isopropyl-silanylene-(phenyl, ethyl-TACH) (methylphosphido)] (hexoxy)(phenylethylamido)lanthanum [1-ethyl-1-phenyl-silanylene-(methyl, pentyl-TACH) (fluorenyl)] (methyl(trimethylsilyl)) (hexyl)holmium; [1-isopropyl-1-propyl-germanylene-(ethyl, methyl-TACN) (fluorenyl)] (phenyl)(diphenylamido) cerium; [1-isopropyl-1-ethyl-methylene-(propyl, methyl-TACN) (2,4-dimethyl-6-phenylindenyl)) (methylpropylphosphido)(phenoxy)yttrium; [1-ethyl-1-isopropyl-methylene-(isopropyl, ethyl-TACN) (perfluorofluorenyl)] (ethyl(trimethylsilyl))(hexyl)scandium; [1-methyl-1-propyl-ethylene-(methyl(triethylsilyl),ethyl-TACN) (t-butylamido)] (ethyl(trimethylsilyl))(ethyl(trimethylsilyl)) neodymium; [1-isopropyl-1-methyl-methylene-(propyl, ethyl(trimethylsilyl)-TACN) (1-bromo-2,3,4-trimethylindenyl)] (dimethylphosphido)(methylethylphosphido)lutetium; [1-phenyl-1-methyl-methylene-(3-methylpentyl, ethyl-TACN) (tetramethycyclopentadienyl)) (methyl(trimethylsilyl))(diphenylphosphido)lanthanum; 11-butyl-1-phenyl-phenylene-(ethyl, 3-methylpentyl-TACN) (perfluorocyclopentadienyl)] (methylpropylamido)(t-butyl) lanthanum; [1-ethyl-1-propyl-silanylene-(3-methylpentyl, 3-methylpentyl-TACN) (perchloroindenyl)] (ethoxy)(methylethylphosphido)europium; [1-phenyl-1-isopentyl-methylene-(methyl, methyl(triethylsilyl)-TACN) (methylamido)] (ethoxy)(isopentoxy)erbium; [1-isopropyl-1-propyl-germanylene-(methyl(triethylsilyl),pentyl-TACN) (indenyl)] (methyl(trimethylsilyl))(methyl(trimethylsilyl))dysprosium; [1-phenyl-1-isopentyl-phenylene-(methyl, ethyl(triethylsilyl)-TAH) (3,4,5,8-tetraphenylfluorenyl)] (methylethylamido)(phenoxy)yttrium; [1-hexyl-1-propyl-ethylene-(ethyl(triethylsilyl),isopentyl-TAH) (methylphosphido)] (phenylethylphosphido)(2-methy-4-ethylphenoxy)thulium; [1-isopropyl-1-propyl-phenylene-(phenyl, butyl-TAH) (indenyl)] (ethyl)(methylethylamido)scandium; [1-methyl-1-ethyl-silanylene-(pentyl, methyl-TAH) (indenyl)] (diphenylamido)(methyl(trimethylsilyl))scandium, [1-methyl-1-hexyl-methylene-(isopropyl, propyl-TAH) (2,4-dimethyl-6-phenylindenyl)] (methylnonylphosphido) (methylnonylphosphido)europium, [1-phenyl-1-isopropyl-silanylene-(isopropyl, methyl(triethylsilyl)-TAH) (fluorenyl)] (diphenylphosphido)(ethyl)europium; [1-propyl-1-phenyl-methylene-(isopropyl, methyl-TAN) (phenylamido)] (3-methylpentyl)(pentyl)yttrium; [1-isopentyl-1-propyl-methylene-(ethyl, propyl-TAN) (t-butylamido)] (methoxy)(isohexyl)yttrium; [1-methyl-1-ethyl-silanylene-(ethyl, isopropyl-TAN) (perfluorofluorenyl)] (ethylpentylphosphido)(phenyl)yttrium; [1-isopropyl-1-butyl-silanylene-(methyl, isohexyl-TAN) (methylamido)] (methylethylamido)(methylpropylamido)yttrium; [1-phenyl-1-propyl-silanylene-(pentyl, ethyl(triethylsilyl)-TAN) (perfluorofluorenyl)] (3-methylpentyl)(phenylethylphosphido)samarium; [1-ethyl-1-methyl-silanylene-(isopentyl, isohexyl-TAN) (cyclopentadienyl)] (methyl(triethylsilyl)) (isopentyl)europium; [1-hexyl-1-propyl-methylene-(hexyl, propyl-TAN) (1-chloro-2,3,4-trimethylfluorenyl)] (diphenylphosphido)(pentoxy)erbium; [1-propyl-1-methyl-methylene-(pentyl, propyl-TNNCH) (2,3-dibromoindenyl)] (dimethylamido)(methylpropylamido)yttrium; [1-methyl-1-ethyl-methylene-(ethyl, heptyl-TNNCH) (perfluorofluorenyl)] (propyl)(methylpropylamido)yttrium; [1,2-diphenylsilanylene-(methyl(triethylsilyl),methyl-TNNCH) (methylamido)] (3,6-dimethylphenoxy)(isohexyl) yttrium; [1-ethyl-1-isopropyl-butylene-(methyl(triethylsilyl),heptyl-TNNCH) (indenyl)] (methylethylamido)(t- butoxy)lanthanum; [1-ethyl-1-propyl-silanylene-(methyl, hexyl-TNNCH) (methylphosphido)] (dimethylamido)(methylethylphosphido)holmium; [1-phenyl-1-methyl-methylene-(di-isopropyl-TNNCH) (indenyl)] (diphenylamido)(phenylethylamido)dysprosium; [1-isopropyl-1-propyl-ethylene-(pentyl, 3-methylpentyl-TNNCH) (cyclopentadienyl)] (isopentyl)(dimethylamido)yttrium; [1-propyl-1-methyl-methylene-(isohexyl, isopropyl-TNNCH) (perfluorofluorenyl)] (3,6-dimethylphenoxy)(2-methy-4-ethylphenoxy)yttrium; [1,1-diethyl-methylene-(isopropyl, phenyl-TNNCH) (methylphosphido)] (methylpropylamido)(ethyl(triethylsilyl))yttrium (1-methyl-1-isopentyl-methylene-(methyl(triethylsilyl),methyl-TNNCN) (perfluorofluorenyl)] (isopentoxy)(3,6-dimethylphenoxy)yttrium; [1-methyl-1-phenyl-silanylene-(pentyl, methyl-TNNCN) (indenyl)] (t-butoxy)(isopropyl)yttrium; [1-isopropyl-1-isopentyl-methylene-(dipropyl-TNNCN) (1-chloro-2,3,4-trimethylfluorenyl)] (ethyl)(methyl(trimethylsilyl))scandium; [1-isopropyl-1-phenyl-phenylene-(propyl, butyl-TNNCN) (2,4-dimethyl-6-phenylindenyl)] (ethoxy)(isopropoxy)scandium; [1-phenyl-1-butyl-methylene-(ethyl, butyl-TNNCN) (t-butylamido)] (pentyl)(phenylethylphosphido)lutetium

EXAMPLES

The following examples are presented to illustrate the discussion above. Although the examples may be directed toward certain invention embodiments, they do not limit the invention in any specific way. In these examples, certain abbreviations are used to facilitate the description. These include standard chemical abbreviations for the elements and certain commonly accepted abbreviations, such as: Me=methyl, Et=ethyl, Bu=butyl, Ph=phenyl, MAO=methylalumoxane, THF=tetrahydrofuran, and TACN=1,4,7-triazacyclononane. When a ligand is described as e.g. $Me_2$-TACN-$(CH_2)_2$N(tBu) this means N,N'-$Me_2$-TACN-N'''—$(CH_2)_2$N(tBu).

All parts, proportions, and percentages are by weights unless otherwise indicated. All molecular weights are weight average molecular weight unless otherwise noted. (The isolated yields of the compounds synthesized are given in mol %).

Molecular weights (weight average molecular weight (Mw) and number average molecular weight (Mn)) were measured by Gel Permeation Chromatography, unless otherwise noted, using a Waters 150 Gel Permeation Chromatograph equipped with a differential refractive index detector and calibrated using polystyrene standards. Samples were run in either THF (45° C.) or in 1,2,4-trichlorobenzene (145° C.), depending upon the sample's solubility, using three Shodex GPC AT-80 M/S columns in series. This general technique is discussed in "Liquid Chromatography of Polymers and Related Materials III" J. Cazes Ed., Marcel Decker, 1981, page 207. No column spreading corrections were employed but data on generally accepted standards, e.g. National Bureau of Standards Polyethylene 1475, demonstrated a precision with 0.1 units for $M_w/M_n$, which was calculated from elution times. Numerical analyses were performed using Expert Ease® software available from Waters Corporation.

All preparations were performed under an inert nitrogen atmosphere, using standard Schlenk or glovebox techniques, unless mentioned otherwise. Dry solvents (toluene, THF, diethyl ether, pentane, hexane) were distilled from sodium or Na/K alloy before use. The toluene used in the polymerization experiments (Aldrich anhydrous, 99.5%) was passed through columns with alumina (Fluka), supported copper scavenger (BASF R3-11) and molecular sieves (4 Å). Ethylene (AGA polymer grade) was passed through columns with supported copper scavenger (BASF R3-11) and molecular sieves (4 Å) before being passed to the reactor. Deuterated solvents were either dried on Na/K alloy and vacuum transferred before use ($C_6D_6$, THF-$d_8$, toluene-$d_8$), or degassed and dried on 4 Å molecular sieves ($C_6D_5Br$).

Example 1

Synthesis of [$Me_2$-TACN-$SiMe_2$NHBu$^t$]

To a solution of 2.20 g (13.49 mmol) of Li[$Me_2$-TACN] in hexane (50 ml) was added 2.34 g (13.50 mmol) of ClSiMe$_2$NHBu$^t$. The mixture was stirred for one hour, after which the solid LiCl precipitate was filtered off. The hexane was removed from the solution under reduced pressure to leave the title compound as light yellow oil. Yield: 3.70 g (12.9 mmol, 97.5%). The identity of the product was established by NMR spectroscopy (purity >95%) and the product was used without further purification.

$^1$H NMR (200 MHz, 20° C., $C_6D_6$) δ: 2.95-2.93 (m, 2H, NCH$_2$), 2.63-2.52 (m, 10H, NCH$_2$), 2.27 (s, 6H, NMe), 1.15 (s, 9H, Bu$^t$), 0.20 (s 6H, SiMe$_2$). $^{13}$C NMR (50.2 MHz, 20° C., $C_6D_6$) δ: 59.88 (t, $J_{CH}$=134.0 Hz, NCH$_2$), 46.47 (q, $J_{CH}$=135.00 Hz NMe$_2$), 33.83 (q, $J_{CH}$=121.3 Hz NCMe$_3$), 1.39 (q, $J_{CH}$=114.7 Hz, SiMe$_2$).

Example 2

Synthesis of Li[$Me_2$-TACN-$SiMe_2$NBu$^t$]

2.14 g (13.0 mmol) of ClSiMe$_2$NHBu$^t$ was added to a solution of 2.12 g (13.0 mmol) of Li[$Me_2$-TACN] in hexane (50 ml). The mixture was stirred for two hours, after which 5.2 mil (13.0 mmol) of Bu$^n$Li (2.5M solution in hexane) were added. The reaction mixture was stirred overnight; after that, the solid LiCl precipitate was filtered off. Hexane was removed from the solution under reduced pressure to leave a brownish oil (3.10 g, 10.6 mmol, 81%). The identity of the product was established by NMR spectroscopy. $^1$H NMR (300 MHz. 25° C., $C_6D_6$) δ: 3.05-3.00 (m, 2H, NCH$_2$), 2.23-2.20 (m, 2H, NCH$_2$), 2.08 (m, 4H, NCH$_2$, 2.05 (s 6H, NMe), 1.85-1.73 (m, 4H, NCH$_2$), 1.62 (s, 9H, Bu$^t$) 0.45 (s, 6H, SiMe$_2$). $^{13}$C NMR (300 MHz, $C_6D_6$) δ: 56.1 (t, 129.3 Hz, NCH$_2$), 53.48 (t, $J_{CH}$=134.2 Hz, NCH$_2$), 50.5 (s, Bu$^t$C), 54.8 (t, $J_{CH}$=133.0 Hz, NCH$_2$), 44.5 (q, $J_{CH}$=134.2 Hz, NMe), 39.2 (q, H$_{CH}$=123.2 Hz, NCMe3), 5.1 (q, $J_{CH}$=113.4 Hz, SiMe$_2$)

Example 3

Synthesis of [$Me_2$-TACN-$SiMe_2$NBu$^t$]Y($CH_2SiMe_3$)$_2$ a) Salt metathesis route. Li[$Me_2$-TACN-$SiMe_2$NBu$^t$] (0.35 g, 2.17 mmol) was added to a suspension of YCl$_3$(THF)$_{3.5}$ (0.96 g, 2.17 mmol) in THF (30 ml) at ambient temperature. The resulting clear solution was stirred for 2 hours. After that, LiCH$_2$SiMe$_3$ (0.40 g, 4.34 mmol) was added. After 30 minutes, the solvent was removed under reduced pressure; and the residue was stripped of residual THF by stirring with pentane (5 ml), which was subsequently removed by vacuum. Extraction with pentane (4×30 ml) and subsequent concentration and cooling of the extract to −30° C. yielded 0.51 g (43%) of analytically pure material.

b) Alkane elimination route. At ambient temperature, a solution of $Me_2$-TACN-$SiMe_2$NBu$^t$ (0.65 g, 2.28 mmol) in pentane (10 ml) was added dropwise to a solution of (Me$_3$SiCH$_2$)$_3$Y(THF)$_2$ (1.12 g, 2.28 mmol) in pentane (60 ml). The reaction mixture was stirred overnight, after which the volatiles were removed by vacuum. The residue was stripped of remaining THF by stirring with 5 ml of pentane that was subsequently removed under reduced pressure. The resulting sticky solid was then extracted with pentane (2×60 ml) and concentrated. Cooling the extract to −30° C. produced the crystalline title compound (0.92 g, 1.67 mmol, 73%). The structure of the product was corroborated by single crystal X-ray diffraction.

$^1$H NMR (300 MHz, 25° C., C$_6$D$_6$) δ: 2.85-2.76 (m, 2H, NCH$_2$), 2.30 (s, 6H, NMe), 2.25-2.11 (m, 4H, NCH$_2$), 1.88-1.62 (m 6H, NCH$_2$), 1.51 (s, 9H, Bu$^t$), 0.45 (s, 18H, CH$_2$SiMe$_3$), 0.26 (s, 6H, SiMe$_2$), −0.51 (dd, $^2J_{HH}$=10.5 Hz, $^2J_{YH}$=3.0 Hz 2H, YCHH), −0.76 (dd, $^2J_{HH}$=10.5 Hz, $^2J_{YH}$=3.0 Hz 2H, YCHH). $^{13}$C NMR (500 MHz, 25° C., C$_6$D$_6$) δ: 57.23 (t, J$_{CH}$=132.1 Hz, NCH$_2$), 55.14 (t, J$_{CH}$=128.9 Hz, NCH$_2$), 52.55 (s, Bu$^t$ C), 50.08 (q, J$_{CH}$=134.0 Hz, NMe), 45.95 (t, J$_{CH}$=133.7 Hz, NCH$_2$), 36.64 (q, J$_{CH}$=124.0 Hz, NCMe$_3$), 32.98 (dt, J$_{CH}$=96.6 Hz, J$_{YH}$=37.0 Hz, YCH$_2$), 5.20 (q, J$_{CH}$=116.0 Hz, CH$_2$SiMe$_3$), 4.11 (q, J$_{CH}$=116.0 Hz, SiMe$_2$). Elemental analysis, calculated (found) for C$_{22}$H$_{53}$N$_4$Si$_3$Y: C 48.14 (47.93); H 10.10 (10.95); N 10.21 (10.25); Y 16.20 (16.19).

Example 4

Synthesis of [Me$_2$-TACN-SiMe$_2$NBu$^t$]Nd)CH$_2$SiMe$_3$)$_2$

Solid LiCH$_2$SiMe$_3$ (0.63 g, 6.67 mmol) was added to a suspension of NdCl$_3$(THF)$_3$ (1.05 g, 2.26 mmol) in THF (60 ml, ambient temperature). Within 5 minutes, a bright blue solution was formed. The solution was stirred overnight, after which it was reacted with Me$_2$-TACN-SiMe$_2$NHBu$^t$ (0.65 g, 2.26 mmol). The resulting green solution was stirred for three hours after which the volatiles were removed by vacuum. The mixture was extracted with pentane (2×50 ml). The obtained green extract was concentrated to 20 ml and cooled (−30° C.), yielding the product (0.66 g, 1.09 mmol, 48.3%). The identity of the product was corroborated by single crystal X-ray diffraction.

Example 5

Reaction of (Me$_2$-TACN-SiMe$_2$NBu$^t$)Y(CH$_2$SiMe$_3$)$_2$ with [HNMe$_2$Ph][B(C$_6$F$_5$)$_4$]

A solution of (Me$_2$-TACN-SiMe$_2$NBu$^t$)Y(CH$_2$SiMe$_3$)$_2$ (27 mg, 49.3 μmol) in C$_6$D$_5$Br (0.6 ml) was added to [HNMe$_2$Ph][B(C$_6$F$_5$)$_4$] (39 mg, 49.3 μmol). The solution was transferred to an NMR tube and analyzed by NMR spectroscopy, which showed full conversion to the cationic species [(Me$_2$-TACN-SiMe$_2$NBu$^t$)Y(CH$_2$SiMe$_3$)][B(C$_6$F$_5$)$_4$], SiMe$_4$ and free PhNMe$_2$. $^1$H NMR (500 MHz, −30° C., C$_6$D$_5$Br) δ: 7.23 (t, $^3J_{HH}$=7.5 Hz, 2H, m-H PhNMe$_2$), 6.77 (t, $^3J_{HH}$=7.5 Hz, 1H, p-H PhNMe$_2$), 6.58 (d, $^3J_{HH}$=7.5 Hz, 2H, o-H PhNMe$_2$) 2.70-2.67 (m, 2H, NCH$_2$), 2.63 (s, 6H, PhNMe$_2$), 2.46-2.44 (m, 2H, NCH$_2$), 2.35-2.25 (m, 8H, NCH$_2$), 2.14 (s, 6H, TACN NMe), 1.18 (s, 9H, Bu$^t$), 0.04 (s, 9H, CH$_2$SiMe$_3$), 0.03 (s, 6H, SiMe$_2$), 0.01 (s, 12H, SiMe$_4$), −0.89 (br, 2H, CH$_2$SiMe$_3$). $^{13}$C NMR (125.7 MHz, −30° C., C$_6$D$_5$Br) δ: 150.12 (s, ipso-C PhNMe$_2$), 148.31 (d, $^1J_{CF}$=240.2 Hz, o-CF, B (C$_6$F$_5$)$_4$), 138.22 (d, $^1J_{CF}$=235.3 Hz, p-CF, B(C$_6$F$_5$)$_4$), 136.27 (d, $^1J_{CF}$=234.7 Hz, m-CF, B(C$_6$F$_5$)$_4$), 129.03 (d, $^1J_{CH}$=151.5 Hz, o-CH PhNMe$_2$), 124.38 (br, ipso-C, B(C$_6$Fs)$_4$), 116.32 (d, $^1J_{CH}$=159.5 Hz, p-CH PhNMe$_2$), 112.27 (d, $^1J_{CH}$=156.3 Hz, m-CH PhNMe$_2$), 56.48 (t, $^1J_{CH}$=135.4 Hz, NCH$_2$), 53.30 (s, Bu$^t$ C.), 52.94 (t, $^1J_{CH}$=140.2 Hz, NCH$_2$), 46.44 (q, $^1J_{CH}$=137.0 Hz, TACN NMe), 45.58 (t, $^1J_{CH}$=138.6 Hz, NCH$_2$), 40.11 (q, $^1J_{CH}$=140.2 Hz, NCMe$_3$), 39.71 (dt, $^1J_{CH}$=91.9 Hz, $^1J_{YC}$=42.0 Hz, YCH$_2$), 35.39 (q, $^1J_{CH}$=124.1 Hz, PhNMe$_2$), 3.96 (q, $^1J_{CH}$=117.7 Hz, YCH$_2$SiMe$_3$), 2.75 (q, $^1J_{CH}$=117.7 Hz, SiMe$_2$), 0.05 (q, $^1J_{CH}$=117.6 Hz, SiMe$_4$). $^{19}$F NMR (470 MHz, 20° C., C$_6$D$_5$Br) δ: −137.17 (d, $^3J_{FF}$=10.3 Hz, o-CF), −167.23 (t, $^3J_{FF}$=20.7 Hz, p-CF), −171.22 (t, $^3J_{FF}$=16.9 Hz, n-CF).

Example 6

Ethylene Polymerization with [Me$_2$-TACN-SiMe$_2$NBu$^t$]M(CH$_2$SiMe$_3$)$_2$(M=Y, Nd) and [HNMe$_2$Ph][B(C$_6$F$_5$)$_4$]

In a typical experiment, separate solutions of the appropriate [Me$_2$-TACN-SiMe$_2$NBu$^t$]M(CH$_2$SiMe$_3$)$_2$ compound and of an equimolar amount of [HNMe$_2$Ph][B(C$_6$F$_5$)$_4$], each in 5 ml of toluene, were made in a dry box. The solutions were each placed into serum-cap-sealed vials. Polymerization was performed in a stainless steel, 0.5 L autoclave. The autoclave was pre-dried and flushed with nitrogen, charged with 150 ml of dry toluene, equilibrated at the desired reaction temperature and pressurized with ethylene (5 bar). The [HNMe$_2$Ph][B(C$_6$F$_5$)$_4$] solution was injected into the reactor using a pneumatically operated injector assembly, and the reaction was started by subsequently injecting the [Me$_2$-TACN-SiMe$_2$NBu$^t$]M(CH$_2$SiMe$_3$)$_2$ solution. Catalyst precursor activation was accomplished in the presence of monomer. Ethylene pressure was maintained during the reaction by replenishing flow. The reactor was stirred for the specified reaction time. After collection, the polymer product was rinsed with methanol and dried in a vacuum oven. The experiments performed are listed in Table 1.

TABLE 1

Ethylene polymerization experiments with [Me$_2$-TACN-SiMe$_2$NBu$^1$]M(CH$_2$SiMe$_3$)$_2$(Ln = Y, Nd) and [HNMe$_2$Ph][B(C$_6$F$_5$)$_4$].

| Catalyst | Temperature (° C.) | Pressure (bar) | PE (g) | Productivity (kg mol$^{-1}$h$^{-1}$) | Temp. jump (° C.) | M$_w$ | M$_w$\M$_n$ |
|---|---|---|---|---|---|---|---|
| Ln = Y | 30[a] | 5 | 31.00 | 646 | 95 | 588,000 | 2.09 |
| Ln = Y | 50[b] | 5 | 10.75 | 1343 | 95 | — | — |
| Ln = Y | 80[b] | 5 | 9.06 | 1132 | 103 | — | — |
| Ln = Nd | 50[b] | 5 | 5.95 | 743 | 65 | — | — |

Conditions:
[a] 31 μmol catalyst; runtime 18 min;
[b] 10 μmol catalyst 1 equiv. of [HNMe$_2$Ph][BPh$_4$$^{F20}$], runtime 10 min, 605 rpm, 150 ml toluene, 0.5 L stainless steel autoclave

Example 7

Copolymerization of Ethylene and 1-Hexene with [(Me)$_2$-TACN-SiMe$_2$NBu$^t$])Y(CH$_2$SiMe$_3$)$_2$ and [HNMe$_2$Ph][B(C$_6$F$_5$)$_4$]

Following the general procedure of Example 6, but with the autoclave charged with a mixture of 150 ml of dry toluene and 20 ml of dry 1-hexene, ethylene (5 bar) was polymerized with [Me$_2$-TACN-SiMe$_2$NBu$^t$)]Y(CH$_2$SiMe$_3$)$_2$ (10 μmol) and an equimolar amount of [HNMe$_2$Ph][B(C6F5)4]. With an initial reaction temperature of 50° C. and a run time of 10 minutes, 8.00 g of polymer was obtained (mp. 133.2° C.). (Catalyst activity 1000 kg polymer/mol Y.atm.h.) NMR spectroscopy indicated the incorporation of 2.3 wt % of 1-hexene into the polymer. $M_w$=137500; $M_w/M_n$=9.71.

Example 8

Synthesis of [Me$_2$-TACN-SiMe$_2$NHBu$^{sec}$]

To a solution of 2.20 g (13.49 mmol) of Li[Me$_2$-TACN] in hexane (50 ml) was added 2.34 g (13.50 mmol) of ClSiMe$_2$NHBu$^{sec}$. The mixture was stirred for one hour, after which the solid LiCl precipitate was filtered off. The hexane was removed from the solution under reduced pressure to leave the title compound as light yellow oil. Yield: 3.70 g (12.9 mmol. 97.5%). The identity of the product was established by NMR spectroscopy. The product was used without further purification.

$^1$H NMR (500 MHz, 20° C., C$_6$D$_6$) δ: 2.76 (m, 1H, MeCH$_2$CHMe), 2.30 (s, 6H, NMe), 2.23-2.08 (m, 12H, NCH$_2$), 1.37 (quint, $^3J_{HH}$=6.5 Hz, 2H, MeCH$_2$CHMe), 1.11 (d, $^3J_{HH}$=5.5 Hz, 3H, MeCH$_2$CHMe), 0.95 (t, $^3J_{HH}$=7.5 Hz, 3H, MeCH$_2$CHMe), 0.21 (s, 3H, SiMe$_2$), 0.18 (s, 3H, SiMe$_2$). $^{13}$C NMR (125.7 MHz, 20° C., C$_6$D$_6$) δ: 55.1 (br NCH$_2$), 54.1 (br NCH$_2$), 53.39 (br NCH$_2$), 49.0 (d, $J_{CH}$=131.6 Hz, MeCH$_2$CHMe), 46.47 (q, $J_{CH}$=135.1 Hz, NMe), 34.4 (t, $J_{CH}$=124.6 Hz, MeCH$_2$CHMe), 25.9 (q, $J_{CH}$=124.6 Hz, MeCH$_2$CHMe), 11.2 (q, $J_{CH}$=124.6 Hz, MeCH$_2$CHMe), –2.0 (br q, $J_{CH}$=115.7 Hz, SiMe$_2$).

Example 9

Synthesis of [Me$_2$-TACN-SiMe$_2$NBu$^{sec}$]Y(CH$_2$SiMe$_3$)$_2$

At ambient temperature, a solution of Me$^2$-TACN-SiMe$_2$NHBu$^{sec}$ (0.85 g, 3.00 mmol) in pentane (10 ml) was added dropwise to a solution of (Me$_3$SiCH$_2$)$_3$Y(THF)$_2$ (1.54 g, 3.13 mmol) in pentane (60 ml). The reaction mixture was stirred overnight, after which the volatiles were removed by vacuum. The residue was stripped of remaining THF by stirring with 5 ml of pentane that was subsequently removed under reduced pressure. The resulting sticky solid was then extracted with pentane (2×50 ml) and concentrated to 20 ml. Cooling the extract to –30° C. produced the crystalline title compound (1.30 g, 2.37 mmol, 79%). The structure of the product was corroborated by single crystal X-ray diffraction.

$^1$H NMR (500 MHz, 20° C., C$_7$D$_8$) δ: 3.35 (m, 1H, MeCH$_2$, CHMe), 2.32 (s, 6H, NMe), 2.29-2.22 (m, 3H, NCH$_2$), 2.19-2.14 (m, 3H, NCH$_2$), 1.98-1.94 (m, 2H, NCH$_2$), 1.92-1.87 (m, 2H, NCH$_2$), 1.84-1.79 (m, 2H, NCH$_2$), 1.70-1.67 (m, 2H, NCH$_2$), 1.56-1.50 (m, 2H, MeCH$_2$CHMe), 1.36 (d, $^3J_{HH}$=6.5 Hz, 3H, MeCH$_2$CHMe), 1.04 (t, $^3J_{HH}$=7.0 Hz, 3H, MeCH$_2$CHMe), 0.34 (s, 18H, CH$_2$SiMe$_3$), 0.19 (s, 3H, SiMe$_2$), 0.18 (s, 3H, SiMe), –0.58 (br, 2H, CH$_2$SiMe$_3$), –0.73 (br, 2H, CH$_2$SiMe$_3$). $^{13}$C NMR (125.7 MHz, 20° C., C$_7$D$_8$) δ: 57.1 (t, $J_{CH}$=137.0 Hz, NCH$_2$), 57.0 (t, $J_{CH}$=133.4 Hz, NCH$_2$), 55.1 (t, $J_{CH}$=135.1 Hz, NCH$_2$), 55.0 (t, $J_{CH}$=133.2 Hz, NCH$_2$), 53.5 (d, $J_{CH}$=128.1 Hz. MeCH$_2$CMe), 50.1 (q, $J_{CH}$=137.0 Hz, NMe), 46.0 (t, $J_{CH}$=133.4 Hz, NCH$_2$), 45.9 (t, $J_{CH}$=133.4 Hz, NCH$_2$), 37.4 (t, $J_{CH}$=122.8 Hz, MeCH$_2$CHMe), 32.3 (dt, $^1J_{YC}$=36.8 Hz, $J_{CH}$=98.3 Hz, YCH$_2$SiMe$_3$), 27.9 (q, $J_{CH}$=124.6 Hz, MeCH$_2$CHMe), 12.7 (q, $J_{CH}$=124.7 Hz, MeCH$_2$CHMe), 5.20 (q, $J_{CH}$=117.7 Hz, CH$_2$SiMe$_3$), 2.3 (q, J=117.5 Hz. SiMe$_2$), 2.2 (q, $J_{CH}$=117.5 Hz, SiMe$_2$). $^1$H NMR (500 MHz, –50° C., C$_7$D$_8$) δ: 3.49 (m, 11, MeCH$_2$CHMe), 2.81 (m, 2H, NCH$_2$), 2.34 (s, 6H, NMe), 2.19-2.15 (m, 3H, NCH$_2$), 2.08-2.07 (m, 2H, NCH$_2$), 1.92-1.89 (m, 2H, NCH$_2$), 1.92-1.82 (m, 3H, NCH$_2$), 1.80-1.78 (m, 2H, NCH$_2$), 1.74-1.68 (m, 2H, MeCH$_2$CHMe), 1.57 (d, $^3J_{HH}$=6.0 Hz, 3H, MeCH$_2$CHMe), 1.22 (t, $^3J_{HH}$=7.5 Hz, 3H, MeCH$_2$CHMe), 0.60, 0.61 (s, 9H, CH$_2$SiMe$_3$), 0.60 (s, 9H, CH$_2$SiMe$_3$), 0.32, 0.34 (s, 6H, SiMe$_2$), –0.35 (br d, $^3J_{HH}$=10.0 Hz, 1H, CH$_2$SiMe$_3$), –040 (br d, $^3J_{HH}$=10.0 Hz, 1H, CH$_2$SiMe$_3$), –0.61 (br d, $^3J_{HH}$=10 Hz, 2H, CH$_2$SiMe$_3$). $^{13}$C NMR (125.7 MHz, –50° C., C$_7$D$_8$) δ: 56.3 (t, $J_{CH}$=133.5 Hz, NCH$_2$), 56.2 (t, $J_{CH}$=133.5 Hz, NCH$_2$), 54.2 (t, $J_{CH}$=133.5 Hz, NCH$_2$), 54.1 (t, $J_{CH}$=133.5 Hz, NCH$_2$), 53.2 (d, $J_{CH}$=130.0 Hz, MeCH$_2$CHMe), 49.9 (q, $J_{CH}$=136.9 Hz, NMe), 45.3 (t, $J_{CH}$=131.6 Hz, NCH$_2$), 45.2 (t, $J_{CH}$=131.6 Hz, NCH$_2$), 37.2 (t, $J_{CH}$=122.9 Hz, MeCH$_2$CHMe), 31.5 (dt, $^1J_{YC}$=36.8 Hz, $J_{CH}$=98.3 Hz, YCH$_2$SiMe$_3$), 31.2 (dt, $^1J_{YC}$=37.0 Hz, $J_{CH}$=100.1 Hz, YCH$_2$SiMe$_3$), 28.1 (q, $J_{CH}$=122.8 Hz, MeCH$_2$CHMe), 13.0 (q, $J_{CH}$=121.0 Hz, MeCH$_2$CHMe), 5.3 (q, $J_{CH}$=115.8 Hz, CH$_2$SiMe$_3$), 2.2 (q, $J_{CH}$=117.5 Hz, SiMe$_2$), 2.2 (q, $J_{CH}$=117.7 Hz, SiMe$_2$).

Example 10

Synthesis of [Me$_2$-TACN-SiMe$_2$NBu$^{sec}$]Sc(CH$_2$SiMe$_3$)$_2$

At ambient temperature, a solution of Me$^2$-TACN-SiMe$_2$nHBu$^{sec}$ (0.15 g, 0.51 mmol) in pentane (10 ml) was added dropwise to a solution of (Me$_3$SiCH$_2$)$_3$Y(thf)$_2$ (0.23 g. 0.51 mmol) in pentane (40 ml). The reaction mixture was stirred overnight, after which the volatiles were removed by vacuum. The residue was stripped of remaining THF by stirring with 5 ml of pentane that was subsequently removed under reduced pressure. The resulting sticky solid was then extracted with pentane (2×50 ml) and the extract was concentrated to 20 ml. Cooling the extract to –30° C. produced the crystalline title compound (0.19 g, 0.37 mmol, 75%).

$^1$H NMR (300 MHz. 20° C., C$_6$D$_6$) δ: 3.79 (m, 1H, MeCH$_2$CHMe), 2.98-2.84 (m, 2H, NCH$_2$), 2.50-2.41 (m, 2H, NCH$_2$), 2.38 (s, 3H, NMe), 2.35 (s, 3H, NMe), 2.32-2.19 (m, 2H, NCH$_2$), 2.02-1.73 (m, 6H, NCH$_2$), 1.46-1.36 (m, 2H, MeCH$_2$CHMe), 1.33 (d, $^3J_{HH}$=6.0 Hz, 3 H, MeCH$_2$CHMe), 1.03 (t, $^3J_{HH}$=7.5 Hz, 3H, MeCH$_2$CHMe), 0.40 (s, 9H, CH$_2$SiMe$_3$), 0.39 (s 9H, CH$_2$SiMe$_3$), 0.25 (s, 3H, SiMe$_2$), 0.22 (s, 3H, SiMe$_2$), –0.15 (d, $^2J_{HH}$=11.1 Hz, 1H$_1$, CH$_2$SiMe$_3$), –0.16 (d, $^2J_{HH}$=10.5 Hz, 1H, CH$_2$SiMe$_3$), –0.34 (d, $^2J_{HH}$=11.1 Hz, 1H, CH$_2$SiMe$_3$), –0.35 (d, $^2J_{HH}$=10.5 Hz, 1H, CH$_2$SiMe$_3$). $^{13}$C NMR (75.4 MHz, 20° C., C$_6$D$_6$) δ: 58.4 (t, $J_{CH}$=136.7 Hz, NCH$_2$), 57.8 (t, $J_{CH}$=136.7 Hz, NCH$_2$), 56.4 (t, $J_{CH}$=134.2 Hz, NCH$_2$), 55.9 (t, $J_{CH}$=133.8 Hz, NCH$_2$), 53.5 (d, $J_{CH}$=131.7 Hz, MeCH$_2$CHMe), 51.2 (q, $J_{CH}$=141.5 Hz, NMe), 51.0 (q, $J_{CH}$=141.5 Hz, NMe), 46.7 (t, $J_{CH}$=135.4 Hz, NCH$_2$), 45.9 (t, $J_{CH}$=135.4 Hz, NCH$_2$), 36.7 (t, $J_{CH}$=125.7 Hz, MeCH$_2$CHMe), 34.9 (br, ScCH$_2$SiMe$_3$), 26.4 (q, $J_{CH}$=124.4 Hz, MeCH$_2$CHMe), 12.8 (q, $J_{CH}$=124.4 Hz,

MeCH$_2$CHMe), 5.0 (q, J$_{CH}$=115.9 Hz, CH$_2$SiMe$_3$), 2.3 (q, J$_{CH}$=116.5 Hz, SiMe$_2$), 2.2 (q, J$_{CH}$=116.5 HZ, SiMe$_2$).

Example 11

Synthesis of [Me$_2$-TACN-SiMe$_2$NBu$^{sec}$]Nd (CH$_2$SiMe$_3$)$_2$

Solid LiCH$_2$SiMe$_3$ (1.50 g, 16.00 mmol) was added to a suspension of NdCl$_3$(THF)$_3$ (2.50 g, 5.35 mmol) in THF (60 ml, ambient temperature). Within 5 minutes a bright blue solution was formed. The solution was stirred overnight, after which it was reacted with Me$_2$-TACN-SiMe$_2$NHBu$^{sec}$ (1.40 g, 5.00 mmol). The resulting green solution was stirred for three hours after which the volatiles were removed by vacuum. The mixture was extracted with pentane (2×50 ml). The obtained green extract was concentrated to 20 ml and cooled (−30° C.), yielding the product (1.80 g, 2.90 mmol 59.6%).

Example 12

Ethylene Polymerization with [Me$_2$-TACN-SiMe$_2$NBu$^{sec}$]Nd(CH$_2$SiMe$_3$)$_2$ (M=Sc, Y, Nd) and [HNMe$_2$Ph][B(C$_6$F$_5$)$_4$]

Following the general procedure described in example 6, experiments were performed at 50° C. reactor temperature for M=Sc, Y and Nd and at 80° C. for M=Sc and Y, as shown in Table 2.

TALBE 2

Ethylene polymerization experiments with [Me$_2$-TACN-SiMe$_2$NBu$^{sec}$)]M(CH$_2$SiMe$_3$)$_2$(M = Sc, Y, Nd) and [HNMe$_2$Ph][B(C$_6$F$_5$)$_4$].

| Catalyst | Temperature (° C.) | Pressure (bar) | PE (g) | Productivity (kg mol$^{-1}$ h$^{-1}$) | Highest Temp. (° C.) |
|---|---|---|---|---|---|
| M = Sc | 50 | 5 | 1.63 | 203 | 52 |
| M = Sc | 80 | 5 | 1.96 | 245 | 82 |
| M = Y  | 50 | 5 | 5.22 | 652 | 58 |
| M = Y  | 80 | 5 | 8.54 | 1067 | 98 |
| M = Nd | 50 | 5 | 2.30 | 287 | 53 |

Conditions:
10 μmol catalyst 1 equiv. of [HNMe$_2$Ph][BPh$_4^{F20}$], runtime 10 min, 605 rpm, 150 ml toluene, 0.5 L stainless steel autoclave

Example 13

Synthesis of (Pr$^i$)$_2$-TACN-SiMe$_2$NHBu$^t$

At ambient temperature, Li[TACN(i-Pr)$_2$] (0.92 g, 4.24 mmol) was added in portions to 30 ml of neat Me$_2$SiCl$_2$. The reaction mixture turned yellow; after which it was stirred for 4 hours. Excess Me$_2$SiCl$_2$ was removed under reduced pressure, and the reaction product was dissolved in toluene (30 ml). LiNHBu$^t$ (0.33 g, 4.24 mmol), at room temperature, was added to the toluene solution. After 18 hours, the toluene was removed under vacuum. The remaining sticky residue was extracted with pentane (2×100 ml). Evaporation of the pentane yielded 0.98 g (68%) of a brownish oil. $^1$H NMR (300 MHz, 25° C., C$_6$D$_6$) δ: 3.17-3.14 (m, 2H, NCH$_2$), 3.06-3.03 (m, 2H, NCH$_2$), 2.79 (sept, $^3$J$_{HH}$=6.3 Hz, 2H, Pr$^i$ CH), 2.77-2.69 (m, 4H, NCH$_2$), 2.52 (s, 4H, NCH$_2$), 1.20 (s, 9H, Bu$^t$), 0.98 (d, $^3$J$_{HH}$=6.3 Hz, 6H, Pr$^i$ Me), 0.93 (d, $^3$J$_{HH}$=6.3 Hz, 6H, Pr$^i$ Me), 0.26 (s, 6H, Me$_2$Si).

Example 14

Synthesis of [(Pr$^i$)$_2$-TACN-SiMe$_2$NBu$^t$]Y (CH$_2$SiMe$_3$)$_2$ a) NMR-tube scale. A solution of (Me$_3$SiCH$_2$)$_3$Y(THF)$_2$ (20 mg, 40.4 μmol) in C$_6$D$_6$ (0.6 ml) was added to (Pr$^i$)$_2$-TACN-SiMe$_2$NHBu$^t$ (14 mg, 40.4 μmol). The solution was transferred to a NMR tube and analyzed with $^1$H NMR spectroscopy. The NMR showed clean conversion to the product, SiMe$_4$, and free THF.

b) Preparative scale. At ambient temperature, a solution of (Pr$^i$)$_2$-TACN-SiMe$_2$NHBu$^t$ (0.35 g, 1.00 mmol) in pentane (10 ml) was added dropwise to a solution of (Me$_3$SiCH$_2$)$_3$Y (THF)$_2$ (0.49 g, 1.00 mmol) in pentane (30 ml). The reaction mixture was stirred overnight, after which the volatiles were removed under vacuum. The residue was stripped of remaining THF by stirring with 5 ml of pentane that was subsequently removed under reduced pressure. The resulting sticky solid was then extracted with pentane (20 ml). Cooling the extract to −30° C. yielded the crystalline product (0.21 g, 0.34 mmol, 34%), which was characterized by NMR spectroscopy. $^1$H NMR (300 MHz, 25° C., C$_6$D$_6$) δ: 2.82 (sept br, 2H, Pr$^i$ CH), 2.76 (m, 2H, NCH$_2$), 2.25 (m, 2H, NCH$_2$), 1.86 (m, 2H, NCH$_2$), 1.73 (m, 2H, NCH$_2$), 1.56 (s, 9H, NBu$^t$), 1.43 (m, 2H, NCH$_2$), 0.97-0.83 (br, 12H, Pr$^i$ Me), 0.42 (s, 18H, Me$_3$SiCH$_2$), 0.28 (s, 6H, Me$_2$Si), 0.40 (br, 2H, YCHH), 0.56 (dd br, 2H, YCHH). $^{13}$C NMR (75.4 MHz, 25° C., C$_6$D$_6$) δ: 55.0 (d, J$_{CH}$=136.7, Pr$^i$ CH), 54.2 (t, J$_{CH}$=135.7 Hz, NCH$_2$), 54.1 (t br, J$_{CH}$=145 Hz, NCH$_2$), 53.1 (t br, part. overlap, NCH$_2$), 52.2 (s, Bu$^t$ C), 50.8 (t br, J$_{CH}$=130.5 Hz, NCH$_2$), 36.5 (q, J$_{CH}$=123.2, Bu$^t$ Me), 33.6 (dt, J$_{CH}$=96.3 Hz, J$_{YH}$=37.8 Hz, YCH$_2$), 18.5 (q, J$_{CH}$=125.6 Hz, Pr$^i$ Me), 5.0 (q, J$_{CH}$=115.8 Hz, Me$_3$SiCH$_2$), 3.5 (q, J$_{CH}$=117.1 Hz, Me$_2$Si).

Example 15

Reaction of [(Pr$i$)$_2$-TACN-SiMe$_2$NBu$^t$]Y (CH$_2$SiMe$_3$)$_2$ with [HNMe$_2$Ph][B(C$_6$F$_5$)$_4$]

a) In the absence of THF. A solution of [(i-Pr)$_2$-TACN-SiMe$_2$NBu$^t$]Y(CH$_2$SiMe$_3$)$_2$ (12 mg, 19.9 μmol) in C$_6$D$_5$Br (0.6 ml) was reacted with [HNMe$_2$Ph][B(C$_6$F$_5$)$_4$] (16 mg, 19.9 μmol). The solution was transferred to a NMR tube and analyzed by NMR spectroscopy, which showed evolution of two equivalents of SiMe$_4$ one equivalent of propene, and the formation of an ill-defined yttrium species.

b) In the presence of THF. A solution of [(i-Pr)$_2$-TACN-SiMe$_2$NBu$^t$]Y(CH$_2$SiMe$_3$)$_2$ (24 mg, 39.8 μmol) in C$_6$D$_5$Br (0.6 ml) with a drop of added THF-d$_8$ was reacted with [HNMe$_2$Ph][B(C$_6$F$_5$)$_4$] (32 mg, 39.8 mmol). The solution was transferred to a NMR tube and analyzed by NMR spectroscopy, which showed full conversion to the cationic species {[(i-Pr)$_2$-TACN-SiMe$_2$NBu$^t$]Y(CH$_2$SiMe$_3$)(THF-d$_8$)}[B(C$_6$F$_5$)$_4$], SiMe$_4$ and free PhNMe$_2$.

$^1$H NMR (500 MHz, 22 C, C$_6$D$_5$Br) δ: 7.23 (t, $^3$J=7.5 Hz, 2H, m-H PhNMe$_2$), 6.77 (t, $^3$J=7.5 Hz, 1H, p-H PhNMe$_2$), 6.58 (d, $^3$J=7.5 Hz, 2H, o-H PhNMe$_2$), 4.01 (sept, J$_{HH}$=6.0 Hz, 1H, Pr$^i$ CH), 2.76-2.69 (m, 4H, NCH$_2$), 2.63 (s, 6H, PhNMe$_2$), 2.56-2.24 (m, 8H, NCH$_2$), 1.20 (sept, J$_{HH}$=6.0 Hz, 1H, Pr$^i$ CH), 1.12 (d, J$_{HH}$=6.0 Hz, 6H, Pr$^i$ Me), 1.10 (s, 9H, Bu$^t$), 0.72 (br, 6H, Pr$^i$ Me), 0.22 (s, 6H SiMe$_2$), 0.01 (s, SiMe$_4$), −0.02 (s, 9H, YCH$_2$SiMe$_3$), −0.84 (d, J$_{HH}$=11.5 Hz, 1H, YCHH), −0.91 (d, J$_{HH}$=11.0 Hz, 1H, YCHH).

Example 16

Ethylene Polymerization with [iPr$_2$-TACN-SiMe$_2$NBu$^t$)]Y(CH$_2$SiMe$_3$)$_2$ and [HNMe$_2$Ph][B(C$_6$F$_5$)$_4$]

Following the general procedure described in Example 6, three separate experiments were performed, as shown in Table 3. Polyethylene could be recovered from none of the experiments, and no reaction exotherm was observed.

TABLE 3

Ethylene polymerization experiments with [iPr$_2$-TACN-SiMe$_2$NBu$^t$)]Y(CH$_2$SiMe$_3$)$_2$ and [HNMe$_2$Ph][B(C$_6$F$_5$)$_4$].

| Temp (° C.) | Ethylene Pressure (bar) | PE produced (g) | Productivity (kg mol-1 h-1 bar-1) | Highest Temp. during run (° C.) |
|---|---|---|---|---|
| 30 | 5 | 0 | 0 | 30 |
| 30a | 5 | 0 | 0 | 30 |
| 50 | 5 | 0 | 0 | 50 |

Conditions:
10 μmol catalyst, 1 equiv. of [HNMe$_2$Ph][B(C$_6$F$_5$)$_4$], run time 10 min, 150 ml toluene, 0.5 L stainless steel autoclave.
a 20 μmol catalyst

Example 17

Synthesis of Me$_2$-TACN-(CH$_2$)$_2$NHBu$^t$ a) N-tert-Butylchloroacetamide. This reaction was performed under aerobic conditions. Chloroacetyl chloride (1.5 ml, 20 mmol) was carefully added to a cold solution of triethylamine (2 ml) in 50 ml of CH$_2$Cl$_2$, placed in an ice-bath. At 0° C., tert-butylamine (2.1 ml, 20 mmol) was added and the mixture was stirred for 1 hour. The mixture was washed with dilute aqueous NaHCO$_3$, with water and once with brine, then dried (Na$_2$SO$_4$). After removal of the solvent, the residue was crystallized from petroleum ether (bp 40-60° C.) to give 1 g (33%) of product, mp 85° C. (reported mp 84° C.). $^1$H NMP (300 MHz, 25° C., CDCl$_3$): □ 1.39 (s, 9H, Bu$^t$), 3.94 (s, 2H, CH$_2$), 6.37 (br, NH).

b) N-tert-Butyl-(4,7-dimethyl-[1,4,7]triazanon-1-yl)acetamide. This reaction was performed under aerobic conditions. N-tert-butylchloroacetamide (1.49 g, 10 mmol) and sodium iodide (10 mg) were added to a solution of crude 4,7-dimethyl-1,4,7-triazacyclononane (1.54 g, 9.8 mmol) in acetonitrile (10 mL) was added. The mixture was refluxed for 1 hour, then poured into a mixture of water (100 ml) and concentrated hydrochloric acid (1 ml). This was washed three times with ether. An aqueous solution of potassium hydroxide (2 g) to the aqueous layer was added and this aqueous solution was extracted with dichloromethane After drying (Na$_2$SO$_4$) and removing the solvent, 1.72 g (6.7 mmol, 67%) of crude product was obtained. $^1$H NMR (300 MHz, 25° C., CDCl$_3$): □ 1.35 (s, 9H, Bu$^t$), 2.36 (s, 6H, NMe), 2.6 (br m, 12H, NCH$_2$), 3.11 (s, 2H, NCH$_2$CO), 8.3 (br, NH).

c) N-tert-Butyl-2-(4,7-dimethyl-[1,4,7]triazanon-1-yl)ethylamine. Lithium aluminium hydride (0.30 g, 8 mmol) to a solution of N-tert-butyl-(4,7-dimethyl-[1,4,7]triazanon-1-yl)acetamide (0.185 g, 0.7 mmol) in 7.5 ml of diglyme was added. The mixture was refluxed for 3 hours, then cooled. Water (1.2 ml) was slowly added with cooling (internal temperature kept around 20° C.). The mixture was stirred until white. After this point, the work-up was continued under aerobic conditions. Na$_2$SO$_4$ (10 g) was added and, after. 15 minutes, the solids were removed and washed with ether. The combined filtrates were concentrated, first using a rotary evaporator, and then a Kugelrohr (0.2 mmHg, 70° C.). The remainder was further purified by acid-base extraction to give 0.11 g (50%) of the product as an oil. The same reaction was also carried out on a 5-mmol scale; the isolated yield of the amine was 45%.

$^1$H NMR (300 MHz, CDCl$_3$, 20° C., δ): 2.66 (m, 4H, NCH$_2$) 2.62 (br, 8H, NCH$_2$), 2.58-2.53 (m, 4H, NCH$_2$), 2.29 (s, 6H, NMe), 1.04 (s, 9H, Bu$^t$), NH not observed. $^{13}$C NMR (75.4 MHz, CDCl$_3$, 20° C.): □ 59.5 (t, JCH=135.6 Hz, NCH$_2$), 57.4 (t, JCH=133.1 Hz, NCH$_2$), 57.3 (t., JCH=130.7 Hz, NCH$_2$), 56.5 (t, JCH=129.5 Hz, NCH$_2$), 49.9 (s, Bu$^t$ C), 46.6 (q, JCH=133.1 Hz, NMe2), 40.4 (t, JCH=133.4 Hz, NCH$_2$), 29.0 (q, JCH=123, 1 Hz, CMe3).

$^{13}$C NMR (75.4 MHz, CDCl$_3$, 20° C., δ): 59.5 (t, J$_{CH}$=134.2 Hz, NCH$_2$), 57.4 (t, J$_{CH}$=131.7 Hz, NCH$_2$), 57.3 (t, JCH=131.7 Hz, NCH$_2$), 56.5 (t, J$_{CH}$=124.2 Hz, NCH$_2$), 49.9 (d, J$_{CH}$=135.4 Hz, Pr$^i$ CH), 46.9 (q, JCH=131.7 Hz, NMe$_2$), 40.4 (t, J$_{CH}$=133.4 Hz, NCH$_2$), 30.8 (q, J$_{CH}$=123.3, Pr$^i$ Me).

Example 18

Synthesis of [Me$_2$-TACN-(CH$_2$)$_2$NBu$^t$]Y(CH$_2$SiMe$_3$)$_2$ a) NMR-tube scale. (Me$_3$SiCH$_2$)$_3$Y(THF)$_2$ (15 mg, 30.4 μmol) was dissolved in C$_6$D$_6$ (0.6 ml) and added to Me$^2$-TACN-(CH$_2$)$_2$NHBu$^t$ (7 mg, 30.4 μmol). The solution was transferred to an NMR tube and analyzed with $^1$H NMR spectroscopy, showing clean conversion to the product, SiMe$_4$, and free THF.

b) Preparative scale. A solution of Me$^2$-TACN-(CH$_2$)$_2$NH-Bu$^t$ (0.38 g, 1.63 mmol) in pentane (10 ml) was added dropwise to a solution of (Me$_3$SiCH$_2$)$_3$Y(THF)$_2$ (0.81 g, 1.63 mmol) in pentane (30 ml) at ambient temperature. The reaction mixture was stirred overnight, after which the volatiles were removed under vacuum. The residue was stripped of residual THF by stirring with pentane (5 ml) that was subsequently removed under vacuum. The sticky solid was extracted with pentane (20 ml). Cooling to −30° C. gave the product as a crystalline solid (0.21 g, 0.34 mmol, 34%). $^1$H NMR (500 MHz, −60° C., C$_7$D$_8$) δ: 3.32 (m, 1H, NCH$_2$), 3.12-3.00 (m, 2H, NCH$_2$), 2.87-2.69 (m, 3H, NCH$_2$), 2.33 (m, 1H, NCH$_2$), 2.33 (s, 3H, NMe$_2$), 2.22 (m, 1H, NCH$_2$), 2.16 (s, 3H, Me$_2$), 1.76-1.56 (m, 4H, NCH$_2$), 1.52 (s, 9H, Bu$^t$), 1.39 (m, 4H, NCH$_2$), 0.64 (s, 9H, Me$_3$SiCH$_2$), 0.57 (s, 9H, Me$_3$SiCH$_2$), −0.62 (d, J$_{HH}$=11.0 Hz, 1H, Me$_3$SiCH$_2$), −0.86 (d, J$_{HH}$=11.0 Hz, 1H, Me$_3$SiCH$_2$), −0.94 (d, J$_{HH}$=11.0 Hz, 1H, Me$_3$SiCl$_2$), −1.06 (d, J$_{HH}$=10.5 Hz, 1H, Me$_3$SiCH$_2$). The J$_{YH}$ coupling on the YCH$_2$ protons is unresolved. $^{13}$C NMR (125.7 MHz, −60° C., C$_7$D$_8$) δ: 59.8 (t, J$_{CH}$=138.9 Hz, NCH$_2$), 58.9 (t, J$_{CH}$=135.2 Hz. NCH$_2$), 57.5 (t, J$_{CH}$=135.4 Hz, NCH$_2$), 54.8 (t, J$_{CH}$=135.3 Hz, NCH$_2$), 53.9 (s, Bu$^t$ C), 53.1 (t, J$_{YC}$=129.6 Hz, NCH$_2$), 51.4 (t, J$_{CH}$=138.6 Hz, NCH$_2$), 49.3 (q, part. overlap, NMe), 48.9 (q, part. overlap, NMe), 48.4 (t, J$_{CH}$=140.4 Hz, NCH$_2$), 47.0 (t, J$_{CH}$=123.7 Hz, NCH$_2$), 30.8 (q, J$_{CH}$=123.3, Bu$^t$ Me), 29.8 (dt, J$_{YC}$=35.4 Hz, J$_{CH}$=93.3 Hz, YCH$_2$), 28.5 (dt, J$_{YC}$=38.9 Hz, J$_{CH}$=97.3 Hz. YCH$_2$), 5.2 (q, J$_{CH}$=116.9 Hz, Me$_3$SiCH$_2$Y), 5.1 (q, J$_{CH}$=116.5 Hz, Me$_3$SiCH$_2$Y).

Example 19

Synthesis of [Me$_2$-TACN-(CH$_2$)$_2$NBu$^t$]Nd(CH$_2$SiMe$_3$)$_2$

Solid LiCH$_2$SiMe$_3$ (0.31 g, 3.30 mmol) was added to a suspension of NdCl$_3$(THF)$_2$ (0.51 g, 1.09 mmol) in THF (60 ml, ambient temperature). Within 5 minutes a bright blue solution was formed. The solution was stirred overnight, after which it was reacted with Me$_2$-TACN-(CH$_2$)$_2$NHBu$^t$ (0.25 g, 1.00 mmol). The resulting green solution was stirred for three hours after which the volatiles were removed by vacuum. The mixture was extracted with pentane (2×50 ml), the obtained green extract was concentrated to 20 ml and cooled (−30° C.), yielding the product (0.26 g, 0.45 mmol 45%). The identity of the product was corroborated by single crystal X-ray diffraction. Elemental analysis calculated (found) for C$_{22}$H$_{53}$N$_4$Si$_2$Nd: C 46.03 (45.58); H 9.31 (9.15); N 9.76 (9.75); Nd 25.12 (25.08).

Example 20

Synthesis of [Me$_2$-TACN-(CH$_2$)$_2$NBu$^t$]La(CH$_2$SiMe$_3$)$_2$

Solid LiCH$_2$SiMe$_3$ (0.28 g, 3.00 mmol) was added to a suspension of LaBr$_3$(THF)$_4$ (0.67 g, 1.00 mmol) in THF (60 ml, ambient temperature). Within 5 minutes a bright yellow solution was formed. The solution was stirred overnight, after which it was reacted with Me$_2$-TACN-(CH$_2$)$_2$NHBu$^t$ (0.25 g, 1.00 mmol). The resulting green solution was stirred for three hours after which the volatiles were removed by vacuum. The mixture was extracted with pentane (2×50 ml), the obtained green extract was concentrated to 20 ml and cooled (−30° C.), yielding the product (0.25 g, 0.44 mmol, 48%).

$^1$H NMR (200 MHz, 20° C., C$_6$D$_6$) δ: 3.08 (m, 2H, NCH$_2$) 2.80 (m, 2H, NCH$_2$), 2.40-2.29 (m, 2H, NCH$_2$), 2.25 (s, 6H, NMe$_2$), 2.17-2.05 (m, 4H, NCH$_2$), 1.76-1.71 (m, 2H, NCH$_2$), 1.66-1.55 (m, 4H, NCH$_2$), 1.44 (s, 9H, Bu$^t$), 0.49 (s, 18H, Me$_3$SiCH$_2$), −0.60 (d, J$_{HH}$=9.5 Hz, 2H, Me$_3$SiCH$_2$), −0.80 (d, J$_{HH}$=10.5 Hz, 2H, Me$_3$SiCH$_2$).

$^{13}$C NMR (125.7 MHz, 20° C., C$_6$D$_6$) δ: 59.7 (t, J$_{CH}$=131.6 Hz. NCH$_2$), 55.7 (t, J$_{CH}$=135.0 Hz, NCH$_2$), 54.9 (s, Bu$^t$ C), 54.3 (t, J$_{CH}$=133.4 Hz, NCH$_2$), 52.1 (t, J$_{CH}$=129.8 Hz, NCH$_2$), 48.1 (t, J$_{CH}$=103.6 Hz, LaCH$_2$), 47.5 (t, J$_{CH}$=128.0 Hz, NCH$_2$), 47.0 (q, J$_{CH}$=135.1 Hz, NMe), 30.2 (q, J$_{CH}$=122.8, Bu$^t$ Me), 5.2 (q, J$_{CH}$=115.8 Hz, Me$_3$SiCH$_2$Y).

Example 21

Reaction of [Me$_2$-TACN-(CH$_2$)$_2$NBu$^t$]Y(CH$_2$SiMe$_3$)$_2$ with [HNMe$_2$Ph][B(C$_6$F$_5$)$_4$]

A solution of [Me$_2$-TACN-(CH$_2$)$_2$NBu$^t$]Y(CH$_2$SiMe$_3$)$_2$ (20 mg, 38.5 μmol) in C$_6$D$_5$Br (0.6 ml) was added to [HNMe$_2$Ph][B(C$_6$F$_5$)$_4$] (30 mg, 38.5 μmol). The solution was transferred to a NMR tube and analyzed by NMR spectroscopy, which showed full conversion to the cationic species {[Me$_2$-TACN-(CH$_2$)$_2$NBu$^t$]Y(CH$_2$SiMe$_3$)}[B(C$_6$F$_5$)$_4$]1, SiMe$_4$ and free PhNMe$_2$.

H NMR (500 MHz, −30° C., C$_6$D$_5$Br) δ: 7.23 (t, $^3$J$_{HH}$=8.0 Hz, 2H, m-H PhNMe$_2$), 6.78 (t, $^3$J$_{CH}$=7.0 Hz, 1H, p-H PhNMe$_2$), 6.60 (d, $^3$J$_{HH}$=8.0 Hz, 2H, o-H PhNMe$_2$), 2.64 (s, 6H, PhNMe$_2$), 2.58-2.22 (m, 16H, NCH$_2$), 2.18 (s, 6H, TACN NMe), 1.09 (s, 9H, Bu$^t$), 0.11 (s, 9H, CH$_2$SiMe$_3$), 0.01 (s, 12H, SiMe$_4$), −1.06 (br, 2H, YCH$_2$). $^{13}$C{$^1$H} NMR (125.7 MHz, C$_6$D$_5$Br, −30° C. δ): 150.14 (ipso-C, PhNMe$_2$), 148.40 (d, $^1$J$_{CF}$=243.4 Hz, o-CF, B(C$_6$F$_5$)$_4$), 138.33 (d, $^1$J$_{CF}$=233.7 Hz, p-CF, B(C$_6$F$_5$)$_4$), 136.42 (d, $^1$J$_{CH}$=248.2 Hz, m-CF, B(C$_6$F$_5$)$_4$), 129.17 (o-CH, PhNMe$_2$), 124.27 (br, ipso-C, B(C$_6$F$_5$)$_4$), 116.84 (p-CH, PhNMe$_2$), 112.68 (m-CH, PhNMe$_2$), 60.09 (NCH$_2$), 56.05 (NCH$_7$), 53.33 (Bu$^t$ C), 53.75 (NCH$_2$), 51.78 (NCH$_2$), 46.51 (TACN NMe), 46.16 (NCH$_2$), 40.50 (PhNMe$_2$), 37.02 (d, $^1$J$_{YC}$=40.7 Hz, YCH$_2$), 30.17 (Bu$^t$ Me), 4.31 (YCH$_2$SiMe$_3$), 0.05 (SiMe$_4$). $^{19}$F NMR (470 MHz, 20° C., C$_6$D$_5$Br) δ: −137.17 (d, $^3$J$_{FF}$=10.3 Hz, o-CF), −167.23 (d, $^3$J$_{FF}$=20.7 Hz, p-CF), −171.22 (d, $^3$J$_{FF}$=16.9 Hz, m-CF).

Example 22

Reaction of [Me$_2$-TACN-(CH$_2$)$_2$NBu$^t$)]La(CH$_2$SiMe$_3$)$_2$ with [HNMe$_2$Ph][B(C$_6$F$_5$)$_4$]

A solution of [Me$_2$-TACN-(CH$_2$)$_2$NBu$^t$]La(CH$_2$SiMe$_3$)$_2$ (11 mg, 20.0 μmol) in C$_6$D$_6$ (0.6 ml) was added to [HNMe$_2$Ph][B(C$_6$F$_5$)$_4$] (16 mg, 20.0 μmol). The obtained solution was transferred to a NMR tube and analyzed by NMR spectroscopy, which showed full conversion to the cationic species {[Me$_2$-TACN -(CH$_2$)$_2$NBu$^t$]La(CH$_2$SiMe$_3$)}[B(C$_6$F$_5$)$_4$], SiMe$_4$ and PhNMe$_2$.

$^1$H NMR (300 MHz, 20° C., C$_6$D$_6$) δ: 7.22 (t, $^3$J$_{HH}$=8.0 Hz, 2H, m-H PhNMe$_2$), 6.79 (t, $^3$J$_{HH}$=7.0 Hz, 1H, p-H PhNMe$_2$), 6.61 (d, $^3$J$_{HH}$=8.0 Hz, 2H, o-H PhNMe$_2$), 2.91 (m, 2H, NCH$_2$), 2.61 (m, 2H, NCH$_2$), 2.49 (s, 6H, PhNMe$_2$), 2.20 (m, 4H, NCH$_2$), 2.11 (s, 6H, TACN NMe), 1.75 (m, 4H, NCH$_2$), 1.28 (s, 9H, Bu$^t$), 0.42 (s, 9H, CH$_2$SiMe$_3$), 0.00 (s, 12H, SiMe$_4$), −0.82 (br, 2H, LaCH$_2$).

Example 23

Ethylene Polymerization with [Me$_2$-TACN-(CH$_2$)$_2$NBu$t$]M(CH$_2$SiMe$_3$)$_2$ (M=V, Nd, La) and [HNMe$_2$Ph][B(C$_6$F$_5$)$_4$]

Following the general procedure described in Example 6, experiments were performed for M=Y at 30, 50 and 80° C. reactor temperature, and at 50° C. for M=Nd and La, as shown in Table 4.

TABLE 4

Ethylene polymerization with [Me$_2$-TACN-(CH$_2$)$_2$NBu$^t$]M(CH$_2$SiMe$_3$)$_2$ (M = Y, Nd, La) and [HNMe$_2$Ph][B(C$_6$F$_5$)$_4$].

| Catalyst | Temp (°C.) | Ethylene Pressure (bar) | PE produced (g) | Productivity (kg mol$^{-1}$ h$^{-1}$ bar$^{-1}$) | Highest Temp during run (°C.) | M$_w$ | M$_w$/M$_n$ |
|---|---|---|---|---|---|---|---|
| M = Y | 30 | 5 | 5.62 | 702 | 64 | 70,700 | 3.97 |
| M = Y | 50 | 5 | 9.40 | 1175 | 82 | 25,800 | 4.91 |
| M = Y | 80 | 5 | 14.30 | 1787 | 103 | 8,400 | 5.95 |
| M = Nd | 50 | 5 | 6.46 | 702 | 71 | 5,900 | 2.25 |
| M = La | 50 | 5 | 0.00 | 0 | 50 | — | — |

Conditions:
10 μmol catalyst, 1 equiv. of [HNMe$_2$Ph][B(C$_6$F$_5$)$_4$], runtime 10 min, 605 rpm, 150 ml toluene, 0.5 L stainless steel autoclave Example 24

Synthesis of Me$_2$-TACN-(CH$_2$)$_2$NHBu$_{sec}$ a) N-2-Butyl-(4,7-dimethyl-[1,4,7]triazanon-1-yl)acetamide. To a solution of crude 4,7-dimethyl-1,4,7-triazacyclononane (2.5 g, 15.9 mmol) in acetonitrile (15 ml) was added N-2-butylchloroacetamide (2.37 g, 15.9 mmol) and 100 mg of sodium iodide. The mixture was refluxed for 3 h, then poured into a mixture of water (40 ml) and 10 ml of 2M hydrochloric acid. This was washed twice with 10 ml of ether. To the aqueous layer was added 20 ml of a 20% solution of sodium hydroxide, and this was extracted with dichloromethane (25, 10, 5 and 5 ml). The combined organic layers were washed once with 10 ml of brine, then dried (Na$_2$SO$_4$). After removal of the solvent, the remainder (about 3.8 g) was dissolved in ether (50 ml). The solution was filtered, and the filtrate was concentrated to give 3.24 g (75%) of the title compound. $^1$H NMR (CDCl$_3$) 0.85 (t, J$_{HH}$=7 Hz, 3H, CH$_2$CH$_3$), 1.05 (d, J$_{HH}$=7 Hz, 3H, CHCH$_3$), 1.39 (m, 2H, CH$_2$), 2.29 (s, 6H, NMe), 2.5-2.6 (12H total, overlapping NCH$_2$), 3.18 (s, 2H, CH$_2$), 3.22 (m, 1H, NCH), 8.8 (br, 1H, NH).

b) N-2-Butyl-2-(4,7-dimethyl-[1,4,7]triazanon-1-yl)ethylamine. To a solution of N-2-butyl-(4,7-dimethyl-[1,4,7]triazanon-1-yl)acetamide (3.24 g, 12.0 mmol) in 10 ml of diglyme was added lithium aluminum hydride (1.16 g, 30 mmol) in portions. After two hours of reflux, water (3 ml) was slowly added while cooling (internal temperature kept around 20° C.), followed by reflux till the color of the mixture was white. Subsequently, Na$_2$SO$_4$ (10 g) was added and after 15 minutes the solids were removed by filtration and washed with 150 ml of ether. The combined filtrates were concentrated using a rotary evaporator, and then a Kugelrohr apparatus (2 torr, 50° C.). The concentrate was then distilled at 120-200° C. (Kugelrohr oven-temperature) to give 2.6 g of distillate. This was distilled again using a short-path distillation apparatus at 0.5 torr with a bath temperature of 70° C., to give 2.24 g (73%) of product. $^1$H NMR (CDCl$_3$) δ 0.84 (t, J$_{HH}$=7.3 Hz, 3H, CH$_2$CH$_3$), 0.97 (d, J$_{HH}$=6.6 Hz, 3H, CHCH$_3$), 1.2-1.4 (m, 2H, CH$_2$), 2.30 (s, 6H, NMe), 2.4-2.5 (about 17H, overlapping NCH$_2$), NH not observed. $^{13}$C NMR (CDCl$_3$, APT) δ 56.8, 55.1, 54.7 and 54.1 (NCH$_2$), 52.5 (NCH), 44.2 (NMe), 43.3 (NCH$_2$), 27.3 (CH$_2$), 17.4 (Me), 8.0 (Me).

Example 25

Synthesis of [Me$_2$-TACN-(CH$_2$)$_2$NBu$^{sec}$]Y(CH$_2$SiMe$_3$)$_2$

A solution of Me$_2$-TACN-(CH$_2$)$_2$NHBu$^{sec}$ (0.65 g, 2.53 mmol) in pentane (10 ml) was added dropwise to a solution of (Me$_3$SiCH$_2$)$_3$Y(THF)$_2$ (1.25 g, 2.50 mmol) in pentane (50 ml) at ambient temperature. The reaction mixture was stirred overnight, after which the volatiles were removed by vacuum. The residue was stripped of residual THF by stirring with pentane (5 ml) that was subsequently removed by vacuum. The resulting sticky solid was extracted with pentane (3×20 ml). Concentrating and cooling the extract to –30° C. gave the title compound as a crystalline solid (1.03 g, 2.00 mmol, 80%). Low temperature solution NMR spectroscopy indicated the presence of two conformational isomers in nearly equimolar amounts.

$^1$H NMR (500 MHz, 20° C., C$_7$D$_8$) δ: 3.33-3.28 (m, 2H, NCH$_2$) 3.14 (m, 1H, MeCH$_2$CHMe), 2.87-2.76 (m, 4H, NCH$_2$), 2.31 (br s, 6H, NMe), 2.23-2.16 (m, 4H, NCH$_2$), 2.09-2.024 (m, 2H, NCH$_2$), 1.83-1.76 (m, 3H, NCH$_2$), 1.66-1.53 (m, 3H, NCH$_2$), 1.43-1.36 (m, 3H, MeCH$_2$CHMe), 1.28 (br, 3H, MeCH$_2$CHMe), 1.11 (br, 3H, MeCH$_2$CHMe), 0.56 (s, 9H, CH$_2$SiMe$_3$), 0.53 (s, 9H, CH$_2$SiMe$_3$), –0.70 (br, 1H, CH$_2$SiMe$_3$), –0.84 (br, 1H, CH$_2$SiMe$_3$), –0.95 (br, 1H, CH$_2$SiMe$_3$), –1.02 (br, 1H, CH$_2$SiMe$_3$). $^{13}$C NMR (125.7 MHz, –50° C., C$_7$D$_8$) δ: 62.2 (t, J$_{CH}$=130.8 Hz, NCH$_2$), 61.1 (t, J$_{CH}$=135.0 Hz, NCH$_2$), 60.1 (t, J$_{CH}$=135.0 Hz, NCH$_2$), 59.4 (t, J$_{CH}$=139.2 Hz, NCH$_2$), 59.3 (t, J$_{CH}$=139.1 Hz, NCH$_2$), 57.6 (t, J$_{CH}$=136.8 Hz, NCH$_2$), 57.5 (t, J$_{CH}$=136.2 Hz, NCH$_2$), 54.8 (t, J$_{CH}$=130.8 Hz, NCH$_2$), 53.3 (t, J$_{CH}$=133.5 Hz, NCH$_2$), 53.2 (t, J$_{CH}$=135.0 Hz, NCH$_2$), 52.9 (d, J$_{CH}$=130.0 Hz, MeCH$_2$CHMe), 51.9 (d, J$_{CH}$=130.7 Hz, MeCH$_2$CHMe), 51.5 (q, J$_{CH}$=135.5 Hz, NMe), 49.5 (q, J$_{CH}$=135.8 Hz, NMe), 49.0 (t, J$_{CH}$=131.6 Hz, NCH$_2$), 48.9 (t, J$_{CH}$=131.6 Hz, NCH$_2$), 48.7 (t, J$_{CH}$=132.2 Hz, NCH$_2$), 33.8 (t, J$_{CH}$=126.8 Hz, NCH$_2$), 30.2 (t, J$_{CH}$=126.1 Hz, MeCH$_2$CHMe), 29.9 (dt, $^1$J$_{YC}$=36.8 Hz, J$_{CH}$=99.1 Hz, YCH$_2$SiMe$_3$), 29.8 (dt, $^1$J$_{YC}$=35.1 Hz, J$_{CH}$=100.1 Hz, YCH$_2$SiMe$_3$), 28.8 (dt, $^1$J$_{YC}$=36.8 Hz, J$_{CH}$=98.3 Hz, YCH$_2$SiMe$_3$), 28.6 (dt, $^1$J$_{YC}$=36.8 Hz, J$_{CH}$=98.2 Hz, YCH$_2$SiMe$_3$), 22.8 (q, J$_{CH}$=124.6 Hz, MeCH$_2$CHMe), 12.7 (q, J$_{CH}$=124.7 Hz, MeCH$_2$CHMe), 12.3 (q, J$_{CH}$=122.4 Hz, MeCH$_2$CHMe), 5.3 (q, J$_{CH}$=115.9 Hz, CH$_2$SiMe$_3$), 5.2 (q, J$_{CH}$=115.9 Hz, CH$_2$SiMe$_3$). C$_{22}$H$_{53}$N$_4$Si$_2$Y: C 50.94 (50.47); H 10.30 (10.27); N 10.80 (10.74); Y 17.14 (17.06).

Example 26

Synthesis of (Me$_2$-TACN-(CH$_2$)$_2$NBu$^{sec}$]Nd(CH$_2$SiMe$_3$)$_2$

Solid LiCH$_2$SiMe$_3$ (0.50 g, 5.31 mmol) was added to a suspension of NdCl$_3$(THF)$_3$ (0.83 g, 1.77 mmol) in THF (60 ml, ambient temperature). Within 5 minutes a bright blue solution was formed. The solution was stirred overnight, after which it was reacted with Me$_2$-TACN-(CH$_2$)$_2$NHBu$^{sec}$ (0.45 g, 1.77 mmol). The resulting green solution was stirred for three hours after which the volatiles were removed by vacuum. The mixture was extracted with pentane (3×50 ml). The obtained green extract was concentrated to 20 ml and cooled (−30° C.), yielding the product (0.47 g, 0.82 mmol 46%).

Example 27

Synthesis of [Me$_2$-TACN-(CH$_2$)$_2$NBu$^{sec}$]Nd(CH$_2$SiMe$_3$)$_2$

Solid LiCH$_2$SiMe$_3$ (0.42 g, 4.50 mmol) was added to a suspension of LaBr$_3$(THF)$_4$ (1.00 g, 1.50 mmol) in THF (60 ml, ambient temperature). Within 5 minutes a bright yellow solution was formed. The solution was stirred overnight, after which it was reacted with Me$_2$-TACN-(CH$_2$)$_2$NHBu$^{sec}$ (0.38 g, 1.50 mmol). The resulting green solution was stirred for three hours after which the volatiles were removed by vacuum. The mixture was extracted with pentane (3×50 ml), the obtained green extract was concentrated to 20 ml and cooled (−30° C.), yielding the product (0.41 g, 0.73 mmol, 48%).

$^1$H NMR (500 MHz, 20° C., C$_6$D$_6$) δ: 3.12-3.06 (m, 2H, NCH$_2$), 3.80 (m, 1H. MeCH$_2$CHMe), 2.37-2.28 (m, 2H, NCH$_2$), 2.23 (br s, 6H, NMe), 2.11-1.96 (m, 6H, NCH$_2$), 1.76-1.71 (m, 2H, NCH$_2$), 1.66 (m, 6H, NCH$_2$), 1.59 (m, 3H, MeCH$_2$CHMe), 1.46 (d, J$_{HH}$=6.0 Hz, 3H. MeCH$_2$CHMe), 1.12 (t, J$_{HH}$=7.4 Hz, 3H, MeCH$_2$CHMe), 0.49 (s, 18H, CH$_2$SiMe$_3$), −0.63 (d, $^2$J$_{HH}$=10.5 Hz, 2H, CH$_2$SiMe$_3$), −0.71 (d, J$_{HH}$=11.0 Hz, 2H, CH$_2$SiMe$_3$). $^{13}$C NMR (125.7 MHz, 20° C., C$_7$D$_8$) δ: 61.3 (d, J$_{CH}$=128.00 Hz, MeCH$_2$CHMe), 59.9 (t, J$_{CH}$=131.5 Hz, NCH$_2$), 55.7 (t, J$_{CH}$=136.8 Hz, NCH$_2$), 54.2 (t, J$_{CH}$=133.2 Hz, NCH$_2$), 52.7 (t, J$_{CH}$=126.3 Hz, NCH$_2$), 52.1 (t, J$_{CH}$=133.4 Hz, NCH$_2$), 48.3 (t, J$_{CH}$=103.5 Hz, LaCH$_2$SiMe$_3$), 46.9 (q, J$_{CH}$=135.1 Hz, NMe), 30.8 (t, J$_{CH}$=124.6 Hz, MeCH$_2$CHMe), 20.9 (q, J$_{CH}$=122.8 Hz, MeCH$_2$CHMe), 11.7 (q, J$_{CH}$=121.0 Hz, MeCH$_2$CHMe), 5.2 (q, J$_{CH}$=115.8 Hz, CH$_2$SiMe$_3$).

Example 28

Reaction of [Me$_2$-TACN-(CH$_2$)$_2$NBu$^{sec}$)]La(CH$_2$SiMe$_3$)$_2$ with [HNMe$_2$Ph][B(C$_6$F$_5$)$_4$]

A solution of [Me$_2$-TACN-(CH$_2$)$_2$NBu$^{sec}$]La(CH$_2$SiMe$_3$)$_2$ (11 mg, 20.0 μmol) in C$_6$D$_6$ (0.6 ml) was added to [HNMe$_2$Ph][B(C$_6$F$_5$)$_4$] (16 mg; 20.0 μmol). The obtained solution was transferred to a NMR tube and analyzed by NMR spectroscopy, which showed full conversion to the cationic species {[Me$_2$-TACN-(CH$_2$)$_2$NBu$^{sec}$]La(CH$_2$SiMe$_3$)}[B(C$_6$F$_5$)$_4$], SiMe$_4$ and PhNMe$_2$.

$^1$H NMR (300 MHz, 20° C. C$_6$D$_6$) δ: 7.22 (t, $^3$J$_{HH}$=8.0 Hz. 2H, m-H-PhNMe$_2$), 6.79 (t, $^3$J$_{HH}$=7.0 Hz, 1H, p-H PhNMe$_2$), 6.61 (d, $^3$J$_{HH}$=8.0 Hz, 2H, o-H PhNMe$_2$), 3.01 (m, 3H, MeCH$_2$CHMe, NCH$_2$), 2.74 (m, 2H, NCH$_2$), 2.50 (s, 6H, PhNMe$_2$), 2.29 (m, 4H, NCH$_2$), 2.18 (s, 6H, TACN NMe), 2.06 (m, 4H, NCH$_2$), 1.71 (m, 5H, MeCH$_2$CHMe, NCH$_2$), 1.38 (br, 3H, MeCH$_2$CHMe), 1.07 (br, 3H, MeCH$_2$CHMe), 0.45 (s, 9H, CH$_2$SiMe$_3$), 0.00 (s, 12H, SiMe$_4$), −0.72 (br, 2H, LaCH$_2$).

Example 29

Ethylene Polymerization with [Me$_2$-TACN-(CH$_2$)$_2$NBu$^{sec}$]M(CH$_2$SiMe$_3$)$_2$ (M=Y, Nd, La) and [HNMe$_2$Ph][B(C$_6$F$_5$)$_4$]

Following the general procedure described in Example 6, experiments were performed at 50° C. reactor temperature for M=Y, Nd and La, and at 80° C. for M=Y, as shown in Table 5. Only for M=Y and Nd was polyethylene produced and a reaction exotherm observed.

TABLE 5

Ethylene polymerization with [Me$_2$-TACN-(CH$_2$)$_2$NBu$^{sec}$]M(CH$_2$SiMe$_3$)$_2$ (M = Y, Nd, La) and [HNMe$_2$Ph][B(C$_6$F$_5$)$_4$].

| Catalyst | Temp. (° C.) | Ethylene Pressure (bar) | PE produced (g) | Productivity (kg mol$^{-1}$ h$^{-1}$ bar$^{-1}$) | Highest Temp during run (° C.) | M$_w$ | M$_w$/M$_n$ |
|---|---|---|---|---|---|---|---|
| M = Y | 50 | 5 | 10.65 | 1331 | 96 | 89,800 | 3.87 |
| M = Y | 80 | 5 | 16.13 | 2016 | 105 | 54,400 | 2.32 |
| M = Nd | 50 | 5 | 4.50 | 562 | 55 | — | — |
| M = La | 50 | 5 | 0.0 | 0 | 50 | — | — |

Conditions:
10 μmol catalyst, 1 equiv. of [HNMe$_2$Ph][B(C$_6$F$_5$)$_4$], runtime 10 min, 605 rpm, 150 ml toluene, 0.5 L stainless steel autoclave

Example 30

Synthesis of Me$_2$-TACN-(CH$_2$)$_2$NHBu$^n$ a) N-1-Butyl-(4,7-dimethyl-[1,4,7]triazanon-1-yl)acetamide. This compound was prepared analogously to the procedure described in Example 24 from N-1-butylchloroacetamide (2.37 g) and 4,7-dimethyl-1,4,7-triazanonane in a yield of 2.97 g (69%). $^1$H NMR,(CDCl$_3$) $^1$H NMR (CDCl$_3$) 0.86 (t, J=7 Hz, 3H, CH$_2$CH$_3$), 1.03 (m, 2H, CH$_2$), 1.42 (m, 2H, CH$_2$), 2.30 (s, 6H, NMe), 2.54 (m, 4H, CH$_2$), 2.57 (m, 8H, CH$_2$), 3.17 (m, 2H NCH$_2$), 3.19 (s, 2H, CH$_2$), 9.2 (br, NH).

b) N-1-Butyl-2-(4,7-dimethyl-[1,4,7]triazanon-1-yl)ethylamine. To a solution of N-1-butyl-(4,7-dimethyl-[1,4,7]triazanon-1-yl)acetamide (2.97 g, 11.0 mmol) in 10 ml of diglyme was added lithium aluminum hydride (1 g, 26 mmol) in portions. After one hour of reflux, water (2.5 ml) was slowly added while cooling (maintaining an internal temperature of about 20° C.), followed by reflux till the color of the mixture was white. $Na_2SO_4$ (10 g) was added to the mixture. After 15 minutes the solids were removed by filtration and washed with 150 ml of ether. The combined filtrates were concentrated using a rotary evaporator and, subsequently, a Kugelrohr apparatus (2 torr, 50° C.). The concentrate was then distilled at 120-200° C. (Kugelrohr oven-temperature) to give 3.33 g of distillate. This was distilled again using a short-path distillation apparatus at 0.75 torr, with a bath temperature of 70-80° C., to give 1.7 g (60%) of product. $^1$H NMR (CDCl$_3$) δ 0.85 (t, J=7.3 Hz, 3H, CH$_2$CH$_3$), 1.3 (m, 2H, CH2), 1.4 (m, 211, CH2), 2.29 (s, 6H, NMe), 2.45-2.65 (188H total, overlapping NCH$_2$), NH not observed. $^{13}$C NMR (CDCl$_3$, APT) δ 56.5, 55.1, 54.7, 54.2, 47.3 and 45.8 (NCH$_2$), 44.2 (NMe), 29.9 (CH$_2$), 18.0 (CH$_2$), 11.5 (CH$_3$)

Example 31

Synthesis of [Me$_2$-TACN-(CH$_2$)$_2$NBu$^n$]Y(CH$_2$SiMe$_3$)$_2$

A solution of Me$_2$-TACN-(CH$_2$)$_2$NHBu$^n$ (0.76 g, 2.96 mmol) in pentane (10 ml) was added dropwise to a solution of (Me$_3$SiCH$_2$)$_3$Y(THF)$_2$ (1.46 g, 2.96 mmol) in pentane (50 ml) at ambient temperature. The reaction mixture was stirred overnight, after which the volatiles were removed by vacuum. The residue was stripped of residual THF by stirring with pentane (5 ml) that was subsequently removed by vacuum. The resulting sticky solid was extracted with pentane (4×20 ml). Concentrating and cooling the extract to –30° C. gave the product as a crystalline solid (1.08 g, 2.10 mmol, 71%).

$^1$H NMR (500 MHz, 20° C., C$_7$D$_8$) δ: 3.29 (t, $^2J_{HH}$=7.5 Hz, 2H, CH$_2$QH$_2$CH$_2$Me), 3.04 (m, 2H, NCH$_2$), 2.26 (s, 6H, NMe), 2.08 (m, 8H, NCH$_2$), 1.74 (m, 6H, NCH$_2$), 1.57 (m, 2H, CH$_2$CH$_2$CH$_2$Me), 1.54 (m, 2H, CH$_2$CH$_2$CH$_2$Me), 1.09 (t, $^2J_{HH}$=7.0 Hz, 3H, CH$_2$CH$_2$CH$_2$Me), 0.40 (s, 18H, CH$_2$SiMe$_3$), –0.79 (d, $^2J_{HH}$=10.5 Hz, 2H, CH$_2$SiMe$_3$), –0.94 (d, $^2J_{HH}$=10.5 Hz, 2H, CH$_2$SiMe$_3$). The $J_{YH}$ coupling on the YCH$_2$ protons is unresolved. $^{13}$C NMR (125.7 MHz, –40° C., C$_7$D$_8$) δ: 60.1 (t, $J_{CH}$=134.1 Hz, NCH$_2$CH$_2$CH$_2$Me), 59.0 (t, $J_{CH}$=138.4 Hz, NCH$_2$), 57.0 (t, $J_{CH}$=132.0 Hz, NCH$_2$), 54.8 (t, $J_{CH}$=127.6 Hz, NCH$_2$), 54.7 (t, $J_{CH}$=128.1 Hz, NCH$_2$), 54.4 (t, $J_{CH}$=136.3 Hz, NCH$_2$), 52.9 (t, $J_{CH}$=132.0 Hz, NCH$_2$), 51.1 (t, $J_{CH}$=132.2 Hz, NCH$_2$), 49.4 (t, $J_{CH}$=134.1 Hz. NCH$_2$), 48.6 (q, $J_{CH}$=136.3 Hz, NMe), 34.7 (t, $J_{CH}$=126.1 Hz, NCH$_2$CH$_2$CH$_2$Me), 29.6 (dt, $^1J_{YC}$=36.5 Hz, $J_{CH}$=97.2 Hz, YCH$_2$SiMe$_3$), 27.5 (dt, $^1J_{YC}$=37.6 Hz, $J_{CH}$=99.5 Hz, YCH$_2$SiMe$_3$), 22.0 (t, $J_{CH}$=125.6 Hz, NCH$_2$CH$_2$CH$_2$Me), 15.3 (q, $J_{CH}$=123.0 Hz, NCH$_2$CH$_2$CH$_2$Me), 12.3 (q, $J_{CH}$=122.4 Hz, MeCH$_2$CHMe), 5.4 (q, $J_{CH}$=117.0 Hz, CH$_2$SiMe$_3$), 5.2 (q, $J_{CH}$=117.0 Hz, CH$_2$SiMe$_3$). C$_{22}$H$_{53}$N$_4$Si$_2$Y: C 50.94 (50.91); H 10.30 (10.33); N 10.80 (10.80); Y 17.14 (17.12).

Example 32

Ethylene Polymerization with [Me$_2$-TACN-(CH$_2$)$_2$NBu$^n$]Y(CH$_2$SiMe$_3$)$_2$ and [HNMe$_2$Ph][B(C$_6$F$_5$)$_4$]

Following the general procedure described in Example 6, a polymerization experiment was performed at 80° C. reactor temperature with 10 µmol catalyst and 1 equiv. of [HNMe$_2$Ph][B(C$_6$F$_5$)$_4$] in toluene, 5 bar ethylene pressure and 10 min run time. Yield: 3.91 g polyethylene (M$_w$=91,500, M$_w$/M$_n$=1.8), catalyst activity 488 kg polymer/mol Y.bar.h.

Example 33

Synthesis of (iPr)$_2$-TACN-(CH$_2$)$_2$NHBu$^t$

Method A:
1.2 g (5.63 mmol) of solid Li[(Pr$^i$)$_2$-TACN] was added to a suspension of 0.73 g (2.81 mmol) HBr.Bu$^t$HN(CH$_2$)$_2$Br (powdered); in 10 ml THF. After 2 hours, the reaction mixture became clear. The mixture was stirred overnight. This solution was then poured into 1 M NaOH (50 ml). The mixture was extracted with CHCl$_3$ (3×50 ml) and the combined organic layers were dried over MgSO$_4$. The solvent was removed under reduced pressure to give a yellow oil. Four, sequential, short-pass distillations of the oil (60° C., 0.01 torr) gave 0.20 g (22%) of product.

Method B:
a) N-tert-Butyl-(4,7-diisopropyl-[1,4,7]triazanon-1-yl)acetamide. N-tert-butylchloroacetamide (0.335 g, 2.25 mmol) was added to a solution of crude 4,7-diisopropyl-1,4,7-triazacyclononane (0.49 g, 2.25 mmol) in dimethylformamide (1 ml). After 2 hours of reflux and work up by using acid-base extraction, a semi-solid material was obtained. This was purified by column chromatography (alumina activity II-III, eluens ether), giving 0.19 g (27%) of product. $^1$H NMR (CDCl$_3$) δ 0.91 (d, 12H), 1.30 (s, 9H), 2.5-2.7 (m, 12H), 2.83 (m, 2H), 3.04 (s, 2H), 7.9 (br, NH).

b) N-tert-Butyl-2-(4,7-diisopropyl-[1,4,7]triazanon-1-yl) ethylamine. Lithium aluminum hydride (0.5 g, 12.5 mmol) was added to a solution of N-tert-butyl-(4,7-diisopropyl-[1,4,7]triazanon-1-yl)acetamide (0.19 g, 0.6 mmol) in 10 ml of dimethoxyethane (DME) was added. After 100 hours reflux and work up (see above), 0.17 g (0.54 mmol, 90%) of crude product was obtained (containing 10% of the acetamide starting material). $^1$H NMR (300 MHz, 25° C., C$_6$D$_6$) δ: 2.82 (sept, $^3J_{HH}$=6.6 Hz, 2H, Pr$^i$ CH), 2.76-2.73 (m, 4H, NCH$_2$), 2.62-2.54 (m, 8H, NCH$_2$), 2.51(s, 4H, NCH$_2$), 1.06 (s, 9H, Bu$^t$), 0.91 (d, $^3J_{HH}$=6.6 Hz, 12H, Pr$^i$ Me), NH not observed. $^{13}$C NMR (75.4 MHz, 25° C., C$_6$D$_6$) δ: 58.7 (d, $J_{CH}$=134 Hz, Pr$^i$ CH), 56.1 (t, $J_{CH}$=131.7, NCH$_2$), 54.6 (t, $J_{CH}$=132 Hz, NCH$_2$), 52.8 (t, $J_{CH}$=128.1 Hz, NCH$_2$), 52.6 (t, $J_{CH}$=128.1 Hz, NCH$_2$), 49.9 (Bu$^t$ C.), 40.3 (t, $J_{CH}$=133.0 Hz, NCH$_2$), 29.0 (q, $J_{CH}$=124.4 Hz, Bu$^t$ Me), 18.3 (q, $J_{CH}$=124.4 Hz, Pr$^i$ Me).

Example 34

Synthesis of [(Pr$^i$)$_2$-TACN-(CH$_2$)$_2$NBu$^t$]Y(CH$_2$SiMe$_3$)$_2$ a) NMR-tube scale (Me$_3$SiCH$_2$)$_3$Y(THF)$_2$ (20 mg, 40.4 µmol) was dissolved in C$_6$D$_6$ (0.6 ml) and added to (Pr$^i$)$_2$-TACN-(CH$_2$)$_2$NHBu$^t$ (12 mg, 40.4 µmol). The solution was transferred to an NMR tube and analyzed with NMR spectroscopy, showing clean conversion to the product, SiMe$_4$, and free THF.

b) Preparative scale. At ambient temperature, a solution of (Pr$^i$)$_2$-TACN-(CH$_2$)$_2$NHBu$^t$ (0.16 g 0.50 mmol) in pentane (10 ml) was added dropwise to a solution of (Me$_3$SiCH$_2$)$_3$Y(THF)$_2$ (0.25 g, 0.52 mmol) in pentane (30 ml). The reaction mixture was stirred overnight, after which the volatiles were removed under vacuum. The residue was stripped of residual THF by stirring with pentane (5 ml), that was subsequently removed under vacuum. The sticky solid was extracted with pentane (20 ml). Cooling to −30° C. gave crystalline product (0.80 g, 0.14 mmol, 28%). The structure of the complex was verified by single crystal X-ray diffraction.

$^1$H NMR (300 MHz, 25° C., $C_6D_6$) δ: 3.77 (sept, $J_{HH}$=6.6 Hz, 1H, Pr$^i$ CH), 3.42 (partially overlapped, Pr$^i$ CH), 3.40 (m, 1H, NCH$_2$), 3.23 (dt, $J_{HH}$=12.0, 3.9 Hz, 1H, NCH$_2$), 3.19-3.09 (m, 2H, NCH$_2$), 2.81 (dt, $J_{HH}$=12.9, 5.1 Hz, 1H, NCH$_2$), 2.50 (dt, $J_{HH}$=12.9, 4.8 Hz, 1H, NCH$_2$), 2.20 (dd, $J_{HH}$=10.8, 3.3 Hz, 1H, NCH$_2$), 2.06-1.97 (m, 3H, NCH$_2$), 1.77 (dd, $J_{HH}$=12.9, 3.9 Hz, 2H, NCH$_2$), 1.71 (m, 1H, NCH$_2$), 1.55 (s, 9H, Bu$^t$), 1.48 (m, 1H, NCH$_2$), 1.31 (d, $J_{HH}$=6.6 Hz, 3H, Pr$^i$ Me), 1.14 (d, $J_{HH}$=6.6 Hz, 3H, Pr$^i$ Me), 0.58 (d, $J_{HH}$=6.6 Hz, 3H, Pr$^i$ Me), 0.48 (s, 9H, Me$_3$SiCH$_2$), 0.47 (d, $J_{HH}$=6.6 Hz, 3H, Pr$^i$ Me), 0.41 (s, 9H, Me$_3$SiCH$_2$), −0.26 (dd, $J_{HH}$=10.5 Hz, $J_{YH}$=3.3 Hz, 1H, YCHH), −0.53 (dd, $J_{HH}$=10.8 Hz, $J_{YH}$=2.1 Hz, 1H, YCHH), −0.83 (dd, $J_{HH}$=10.8 Hz, $J_{YH}$=30 Hz, 1H, YCHH), −1.00 (dd, $J_{HH}$=10.8 Hz, $J_{YH}$=2.1 Hz, 1H, YCHH). $^{13}$C NMR (125.7 MHz, $C_6D_6$, δ): 57.7 (t, $J_{CH}$=128.9 Hz, NCH$_2$), 56.0 (t, $J_{CH}$=132.2 Hz, NCH$_2$), 54.9 (d, $J_{CH}$=138.6 Hz, Pr$^i$ CH), 54.5 (d, $J_{CH}$=143.4 Hz, Pr$^i$ CH), 53.8 (s, Bu$^t$ C), 52.2 (t, $J_{CH}$=138.6 Hz, NCH$_2$), 51.5 (t, $J_{CH}$=137.0 Hz, NCH$_2$), 51.1 (t, $J_{CH}$=135.7 Hz, NCH$_2$), 44.8 (t, $J_{CH}$=128.8 Hz, NCH$_2$), 41.6 (t, $J_{CH}$=130.4 Hz, NCH$_2$), 41.5 (t, $J_{CH}$=127.3 Hz, NCH$_2$), 33.7 (dt, $J_{YC}$=36.9 Hz, $J_{CH}$=95.1 Hz, YCH$_2$), 31.2 (q, $J_{CH}$=122.4, Bu$^t$ Me), 31.0 (t, $J_{YC}$=38.7 Hz, $J_{CH}$=95.0 Hz, YCH$_2$), 23.5 (q, $J_{CH}$=127.3 Hz, Pr$^i$ Me), 23.0 (q, $J_{CH}$=125.7 Hz, Pr$^i$ Me), 13.1 (q, $J_{CH}$=125.7 Hz, Pr$^i$ Me), 12.7 (q, $J_{CH}$=125.7 Hz, Pr$^i$ Me), 5.4 (q, $J_{CH}$=117.6 Hz, Me$_3$SiCH$_2$Y), 5.2 (q, $J_{CH}$=116.0 Hz, Me$_3$SiCH$_2$Y).

Example 35

Reaction of [(Pr$^i$)$_2$-TACN-(CH$_2$)$_2$NBu$^t$]Y(CH$_2$SiMe$_3$)$_2$ with [HNMe$_2$Ph][B(C$_6$F$_5$)$_4$]

a) In the absence of THF. A solution of [(Pr$^i$)$_2$-TACN-(CH$_2$)$_2$NBu$^t$]Y(CH$_2$SiMe$_3$)$_2$ (12 mg, 20.8 μmol) in C$_6$D$_5$Br (0.6 ml) was added to [HNMe$_2$Ph][B(C$_6$F$_5$)$_4$] (17 mg, 20.8 μmol). The solution was transferred to a NMR tube and analyzed by NMR spectroscopy, which showed evolution of two equivalents of SiMe$_4$ one equivalent of propene, and the formation of an ill-defined yttrium species.

b) In the presence of THF. A solution of [(Pr$^i$)$_2$-TACN(CH$_2$)$_2$NBu$^t$]Y(CH$_2$SiMe$_3$)$_2$ (24 mg, 41.6 μmol) in C$_6$D$_5$Br (0.6 ml) with three drops of additional THF-d$_8$ was added to [HNMe$_2$Ph][B(C$_6$F$_5$)$_4$] (34 mg, 41.6 μmol). The solution was transferred into a NMR tube and analyzed by NMR spectroscopy, which showed full conversion to the cationic species, SiMe$_4$, free PhNMe$_2$, and {[(Pr$^i$)$_2$-TACN-(CH$_2$)$_2$NBu$^t$]Y(CH$_2$SiMe$_3$)(THF-d$_8$)}[B(C$_6$Fs)$_4$].

$^1$H NMR (500 MHz, −30° C., C$_6$D$_5$Br) δ: 7.23 (t, $^3$J=7.5 Hz, 2H, m-H PhNMe$_2$), 6.77 (t, $^3$J=7.5 Hz, 1H, p-H PhNMe$_2$), 6.58 (d, $^3$J=7.5 Hz, 2H, o-H PhNMe$_2$), 3.48 (sept, $J_{HH}$=6.0 Hz, 1H, Pr$^i$ CH), 3.40 (t, $J_{HH}$=13.0 Hz, 1H, NCH$_2$), 2.79-2.75 (m, 2H, NCH$_2$), 2.72 (s, 6H, PhNMe$_2$), 2.68-2.59 (m, 3H, NCH$_2$), 2.55-2.48 (m, 2H, NCH$_2$), 2.42-2.29 (m, 3H, NCH$_2$), 2.25-2.17 (m, 3H, NCH$_2$), 1.27 (br, 1H, Pr$^i$ CH), 1.18 (d, $J_{HH}$=6.0 Hz, 6H, Pr$^i$ Me), 1.15 (s, 9H, Bu$^t$), 0.84 (d, $J_{HH}$=5.5 Hz, 3H, Pr$^i$ Me), 0.80 (d, $J_{HH}$=5.5 Hz, 3H, Pr$^i$ Me), 0.09 (s, 9H, Me$_3$SiCH$_2$), 0.07 (s, 12H, Me$_4$Si), −1.29 (dd, $J_{HH}$=11.0 Hz, $J_{YH}$=3.0 Hz, 1H, YCHH), −1.35 (dd, $J_{11}$=11.0 Hz, $J_{YH}$=3.0 Hz, 1H, YCHH).

Example 36

Ethylene Polymerization with [(Pr$^i$)$_2$-TACN-(CH$_2$)$_2$NBu$^t$]Y(CH$_2$SiMe$_3$)$_2$ and [HNMe$_2$Ph][B(C$_6$F$_5$)$_4$]

Following the general procedure of Example 6, ethylene was polymerized with [(Pr$^i$)$_2$-TACN-(CH$_2$)$_2$NBu$^t$]Y(CH$_2$SiMe$_3$)$_2$ (10 mol) and an equimolar amount of [HNMe$_2$Ph][B(C$_6$F$_5$)$_4$]. The reactor used 150 ml of toluene; a 30° C., initial reactor temperature; and a 15-minute run time. 11.95 grams of polyethylene were extracted. (Catalyst activity 956 kg polymer/mol Y.atm.h.)

Example 37

Synthesis of N-tert-butylaminoethyl-bis-(2dimethylamino ethyl)amine a) N-tert-Butyl-bis-(2-dimethylamino-ethyl)-amino acetamide. A mixture of bis-(2-dimethylamino-ethyl)amine (4 g, 25 mmol), N-tert-butylchloroacetamide (3.8 g, 26 mmol), acetonitrile (10 ml), potassium iodide (0.3 g) and 4 g of powdered K$_2$CO$_3$ was stirred at room temperature for 20 hours. The solids were filtered off and washed with ether (3×25 mL). The filtrates were combined and concentrated. The residue was extracted with three 25 mL portions of warm ether. The extracts were combined and, after removal of the solvent under reduced pressure, distilled using a Kugelrohr apparatus (oven 180° C., 0.4 torr), to give 2.1 g (37%) of product. $^1$H NMR (CDCl$_3$) δ 1.29 (s, 91-1, Bu$^t$), 2.16 (s, 12H, NMe$_2$), 2.27 (t, J=7 Hz, 4H, NCH$_2$), 2.57 (t, J=7 Hz, 4H, NCH$_2$), 2.95 (s, 2H, NCH$_2$), 7.9 (br, 1H, NH). $^3$C NMR (CDCl$_3$, APT) δ 168.9 (C=O), 57.2, 55.1 and 51.7 (NCH$_2$), 45.1 (CMe$_3$), 43.2 (NMe), 26.1 (CMe$_3$).

b) N-tert-Butylaminoethyl-bis-(2-dimethylamino ethyl) amine.

A solution of the N-tert-t-Butyl-bis-(2-dimethylamino-ethyl)-amino acetamide (1.5 g, 5.5 mmol) was reduced with 1 g of LiAlH$_4$ in 10 mL of dimethoxyethane (18 hours at reflux). After work-up following a procedure as described e.g. in Example 24, 1.5 g (83%) of [Me$^2$N(CH$_2$)$_2$]$_2$N(CH$_2$)$_2$NH-Bu$^t$ was obtained as a colorless oil (Kugelrohr distillation, 1.5 torr, 150° C.). $^1$H NMR (CDCl$_3$) δ 1.03 (s, 9H, Bu$^t$), 2.16 (s, 12H, NMe), 2.3 and 2.5 (m, 12H total, NCH$_2$), NH not observed. $^{13}$C NMR (CDCl$_3$, APT) δ 56.8, 55.0, 52.7 and 50.3 (NCH$_2$), 43.4 (NMe), 37.6 (CMe$_3$), 26.5 (CMe$_3$). MS (CI); for C$_{14}$H$_{34}$N$_4$ m/z 259 (M+H)$^+$.

Example 38

Synthesis of [{Me$_2$N—(CH$_2$)$_2$}$_2$N(CH$_2$)$_2$NBu$^t$]Y(CH$_2$SiMe$_3$)$_2$ A solution of [Me$_2$N(CH$_2$)$_2$]$_2$N(CH$_2$)$_2$NHBu$^t$ (0.51 g, 2.00 mmol) in pentane (10 ml) was added dropwise to a solution of (Me$_3$SiCH$_2$)$_3$Y(THF)$_2$ (0.98 g, 2.00 mmol) in pentane (50 ml) at ambient temperature. The reaction mixture was stirred for 4 hours, after which the volatiles were removed by vacuum. The residue was stripped of residual THF by stirring with pentane (5 ml), that was subsequently removed by vacuum. The resulting sticky solid was extracted with pentane (2×50 ml). Concentrating and cooling the extract to −30° C. gave the product as a crystalline solid (0.70 g, 1.36 mmol, 68%). The structure of the complex was verified by single crystal X-ray diffraction.

$^1$H NMR (500 MHz. 20° C., C$_6$D$_6$) δ: 3.34 (m, 1H, NCH$_2$), 3.23 (m, 1H, NCH$_2$), 3.08 (t, J$_{HH}$=6.00 Hz, 2H, NCH$_2$), 2.57 (m, 2H, NCH$_2$), 2.02 (s, 12H, NMe$_2$), 1.59-1.52 (m, 6H, NCH$_2$), 1.46 (s, 9H, Bu$^t$), 0.43 (s, 18H, Me$_3$SiCH$_2$), −0.54 (br, 2H, Me$_3$SiCH$_2$), −0.81 (br, 2H, Me$_3$SiCH$_2$). The J$_{YH}$ coupling on the YCH$_2$ protons is unresolved. $^{13}$C{$^1$H} NMR (75.4 MHz, 20° C., C$_6$D$_6$) δ: 71.6 (NCH$_2$) 70.1 (NCH$_2$), 59.0 (NCH$_2$), 57.0 (NCH), 55.9 (NCH$_2$), 53.7 (s, Bu$^t$ C), 50.9 (NMe$_2$), 47.3 (NMe$_2$), 44.4 (NCH$_2$), 30.9 (d, J$_{YC}$=36.6 Hz, YCH$_2$), 29.9 (Bu$^t$ Me), 5.2 (Me$_3$SiCH$_2$Y).

Example 39

Ethylene Polymerization with [{Me$_2$N—(CH$_2$)$_2$}$_2$N (CH$_2$)$_2$N Bu$^t$]Y(CH$_2$SiMe$_3$)$_2$ and [HNMe$_2$Ph][B (C$_6$F$_5$)$_4$] and [Ph$_3$C][B(C$_6$F$_5$)$_4$]

Following the general procedure of Example 6, ethylene was polymerized with [{Me$_2$N—(CH$_2$)$_2$}$_2$N(CH$_2$)$_2$NBu$^t$]Y (CH$_2$SiMe$_3$)$_2$ (10 μmol) and an equimolar amount of [Ph$_3$C] [B(C$_6$F$_5$)$_4$]. With 150 ml of toluene as solvent, an initial reactor temperature of 50° C., and a run time of 18 minutes, 0.12 g of polyethylene was obtained. (Catalyst activity 7.2 kg polymer/mol Y.atm.h.). Ethylene polymerization was not observed when the combination of [{Me$_2$N—(CH$_2$)$_2$}$_2$N (CH$_2$)$_2$N Bu$^t$]Y(CH$_2$SiMe$_3$)$_2$ with [HNMe$_2$Ph][B(C$_6$F$_5$)$_4$] was applied.

While certain representative embodiments and details have been shown to illustrate the invention, it will be apparent to skilled artisans that various process and product changes from those this document discloses may be made without departing from this invention's scope.

All patents, test procedures, and other cited documents are fully incorporated by reference to the extent that this material is consistent with this specification and for all jurisdictions in which such incorporation is permitted. All documents to which priority is claimed are fully incorporated by reference for all jurisdictions in which such incorporation is permitted. Although dependent claims have single dependencies in accordance with U.S. practice, each of the features in any of the dependent claims can be combined with each of the features of one or more of the other dependent claims dependent upon the same independent claim or claims.

Certain features of the present invention are described in terms of a set of numerical upper limits and a set of numerical lower limits. It should be appreciated that ranges formed by any combination of these limits are within the scope of the invention unless otherwise indicated.

What is claimed is:

1. A polymerization catalyst precursor comprising:
   a) a metal from the Group-3 or lanthanide metals;
   b) a neutral, multidentate ligand comprising at least two Group-15 moieties wherein at least one of the Group-15 moieties connects to the metal;
   c) a monoanion connected to the metal;
   d) a bridge, wherein the bridge connects the monoanion to the multidentate ligand;
   e) an abstractable ligand; and
   f) an olefin insertion ligand.

2. The catalyst precursor of claim 1 wherein at least one Group-15 moiety connects to a substituted or unsubstituted organic group.

3. The catalyst precursor of claim 2 further comprising at least one Group-14 moiety connected between at least two of the Group-15 moieties.

4. The catalyst precursor of claim 1 wherein the multidentate ligand contains a ring comprising at least two of the Group-15 moieties.

5. The catalyst precursor of claim 4 wherein the ring comprises at least three Group-15 moieties.

6. The catalyst precursor of claim 5 wherein the ring further comprises at least one Group-14 moiety connected between at least two of the Group-15 moieties.

7. The catalyst precursor of claim 1 wherein the bridge comprises at least one Group-13-to-16 element.

8. The catalyst precursor of claim 7 wherein the metal is a lanthanide.

9. The catalyst precursor of claim 7 wherein the metal is a Group-3 transition metal.

10. The catalyst precursor of claim 1 wherein the abstractable ligand is a radical independently selected from hydride, hydrocarbyl, alkoxide, aryloxide, amide, or phosphide radicals.

11. The catalyst precursor of claim 1 wherein the olefin insertion ligand is a radical independently selected from hydride, hydrocarbyl, alkoxide, aryloxide, amide, or phosphide radicals.

12. The catalyst precursor of claim 10 wherein the abstractable ligand is independently one of 3-methylpentyl, butoxy, butyl, dimethylamido, 3,6-dimethylphenoxy, dimethylphosphido, diphenylamido, diphenylphosphido, ethoxy, diethyl(tri ethylsilyl), ethyl(trimethylsilyl), ethylpentylphosphido, heptyl, hexoxy, hexyl, isohexyl, isopentoxy, isopentyl, isopropoxy, isopropyl, methoxy, dimethyl(triethylsilyl), methyl(trimethylsilyl), methylethylamido, 2-methy-4-ethylphenoxy, methylethylphosphido, methylnonylphosphido, methylpropylamido, methylpropylphosphido octyl, pentoxy, pentyl, phenoxy, diphenylethylamido, phenylethylphosphido, propoxy, propyl, t-butoxy, and t-butyl.

13. The catalyst precursor of claim 1 wherein the abstractable ligand is independently one of methyl(triethylsilyl), methyl(trimethylsilyl), phenyl, neopentyl, and benzyl.

14. The catalyst precursor of claim 1 wherein the abstractable ligand is a divalent anionic chelating ligand.

15. The catalyst precursor of claim 14 wherein the abstractable ligand is an alkylidenyl or a cyclometallated hydrocarbyl radical.

16. The catalyst precursor of claim 1 wherein the abstractable ligand is a diene.

17. An olefin polymerization process comprising:
   a) providing monomer;
   b) providing a polymerization catalyst precursor comprising:
      (i) a metal from Group-3 or lanthanide metals;
      (ii) a multidentate ligand comprising:
         a first ligand part comprising at least two Group-15 moieties, wherein at least two Group 15 moieties connect to each other through at least one Group-14 moiety wherein the first ligand part connects to the metal and wherein each Group-15 moiety is optionally bonded to a substituted or unsubstituted organic group;
         a monoanion connected to the metal;
         a bridge that connects the monoanion to the first ligand part;
         at least one abstractable ligand; and
         at least one olefin insertion ligand;
   c) activating the catalyst precursor; and
   d) contacting the monomer with the catalyst under suitable polymerization conditions.

18. The process of claim 17 wherein the multidentate ligand contains a ring comprising at least two of the Group-15 moieties.

19. The process of claim 18 wherein the multidentate ligand contains a ring comprising the three Group-15 moieties.

20. The process of claim 17 wherein the bridge comprises at least one Group-13-to-16 element.

21. A catalyst precursor comprising a metal complex with the formula:

$$M(LTE)(Q)_nL'_w$$

where
a) M is a Group-3 or lanthanide metal;
b) LTE is a multidentate ligand wherein L is $$C_6H_{12-x}Pn_3R_2R''_x$$

and
(i) R" is independently selected from $C_1$-$C_{20}$ hydrocarbyl radicals; $C_1$-$C_{20}$ substituted hydrocarbyl radicals having at least one hydrogen group wherein one of the at least one hydrogen groups is substituted by a halogen; amido; phosphido; alkoxy; or aryloxy group; and $C_1$-$C_{20}$ hydrocarbyl-substituted Group-13-14 metalloid radicals;
(ii) R is independently selected from hydrogen; $C_1$-$C_{20}$ hydrocarbyl radicals; $C_1$-$C_{20}$ substituted hydrocarbyl radicals having at least one hydrogen group wherein one of the at least one hydrogen groups is substituted by a halogen; amido; phosphido; alkoxy; or aryloxy group; and $C_1$-$C_{20}$ hydrocarbyl-substituted Group-13-14 metalloid radicals;
(iii) Pn is a pnictide; and
(iv) x is the number of R" substituents;
E is an anion; and T is a group connecting L and E; and
c) Q are radical ligands independently selected from hydride, hydrocarbyl, alkoxide, aryloxide, amide or phosphide radicals; an alkylidenyl or a cyclometallated hydrocarbyl radical; and a diene;
d) n is 1 or 2;
e) L' is an optional Lewis base; and
f) w=0, 1, or 2.

22. The catalyst precursor of claim 21 wherein Pn is selected from phosphorous or nitrogen.

23. The catalyst precursor of claim 21 wherein T comprises at least one Group-14 or -15 element.

24. The catalyst precursor of claim 22 wherein E comprises at least one Group-14-to-16 element.

25. The catalyst precursor of claim 24 wherein E is selected from cyclopentadienyl, substituted amido, substituted phosphido, oxygen, sulfur, or selenium moieties.

26. The catalyst precursor of claim 22 wherein x=2.

27. A catalyst comprising an activator and a metal complex with the following formula $$(C_6H_{12-x}N_3R_2R''_xTNR')MQ_2L_w' \text{ or } (C_4H_{8-x}N_3R_4R''_xTNR')MQ_2L_w'$$

wherein
a) M is a Group-3 or lanthanide metal;
b) N is nitrogen;
c) T is a covalent bridging group comprising at least one Group-14 or -15 atom;
d) R is independently selected from
(i) hydrogen;
(ii) $C_1$-$C_{20}$ hydrocarbyl radicals;
(iii) $C_1$-$C_{20}$—substituted hydrocarbyl radicals having at least one hydrogen group wherein one of the at least one hydrogen groups is substituted by a halogen; amido; phosphido; alkoxy; or aryloxy group; and
(iv) $C_1$-$C_{20}$ hydrocarbyl-substituted Group-13-14 metalloid radicals;
e) R' and R" are independently selected from
(i) $C_1$-$C_{20}$ hydrocarbyl radicals;
(ii) $C_1$-$C_{20}$—substituted hydrocarbyl radicals having at least one hydrogen group wherein one of the at least one hydrogen groups is substituted by a halogen; amido; phosphido; alkoxy; or aryloxy group; and
(iii) $C_1$-$C_{20}$ hydrocarbyl-substituted Group-13-14 metalloid radicals;
f) Q are radicals independently selected from hydride hydrocarbyl, alkoxide, aryloxide, amide or phosphide radicals; or two Q are an alkylidenyl or a cyclometallated hydrocarbyl radical, or a diene;
g) L' are Lewis basic ligands; and
h) w is 0, 1, or 2; and
i) x is the number of R" substituents.

28. A catalyst comprising an activator and a metal complex with the following formula $$(C_6H_{12-x}N_3R_2R''_xTCp)MQ_2L_w' \text{ or } (C_4H_{8-x}N_3R_2R''_xTCp)MX_2L_w'$$

wherein
a) M is a Group-3 or lanthanide metal;
b) R is independently selected from
(i) hydrogen;
(ii) $C_1$-$C_{20}$ hydrocarbyl radicals;
(iii) $C_1$-$C_{20}$ substituted hydrocarbyl radicals having at least one hydrogen group wherein one of the at least one hydrogen groups is substituted by a halogen; amido; phosphido; alkoxy; or aryloxy group; and
(iv) $C_1$-$C_{20}$ hydrocarbyl-substituted Group-13-14 metalloid radicals;
c) R" is independently selected from
(i) $C_1$-$C_{20}$ hydrocarbyl radicals;
(ii) $C_1$-$C_{20}$—substituted hydrocarbyl radicals having at least one hydrogen group wherein one of the at least one hydrogen groups is substituted by a halogen; amido; phosphido; alkoxy; or aryloxy group; and
(iii) $C_1$-$C_{20}$ hydrocarbyl-substituted Group-13-14 metalloid radicals;
d) T is a covalent bridging group comprising at least one Group-14 or -15 atom;
e) Q are radicals independently selected from hydride, hydrocarbyl, alkoxide, aryloxide, amide or phosphide radicals; or two Q are an alkylidenyl or a cyclometallated hydrocarbyl radical, or a diene;
f) L' are Lewis basic ligands;
g) Cp is a cyclopentadienyl ligand;
h) N is nitrogen;
i) w is 0, 1, or 2; and
j) x is the number of R" substituents.

29. A catalyst comprising an activator and a metal complex wherein the metal complex has the formula shown in I or II

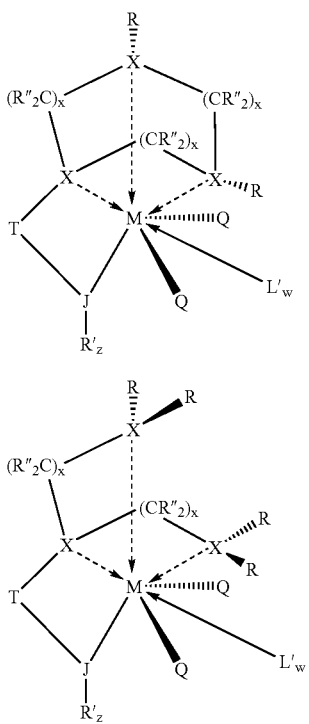

wherein
a) M is a Group-3 or lanthanide metal;
b) T is a covalent bridging group comprising at least one Group-14 or -15 atom;
c) R and R" are independently selected from
   (i) hydrogen;
   (ii) $C_1$-$C_{20}$ hydrocarbyl radicals;
   (iii) $C_1$-$C_{20}$ substituted hydrocarbyl radicals having at least one hydrogen group wherein one of the at least one hydrogen groups is substituted by a halogen; amido; phosphido; alkoxy; or aryloxy group; and
   (iv) $C_1$-$C_{20}$ hydrocarbyl-substituted Group-13-14 metalloid radicals;
d) R' is independently selected from
   (i) $C_1$-$C_{20}$ hydrocarbyl radicals;
   (ii) $C_1$-$C_{20}$ substituted hydrocarbyl radicals having at least one hydrogen group wherein one of the at least one hydrogen groups is substituted by a halogen; amido; phosphido; alkoxy; or aryloxy group; and
   (iii) $C_1$-$C_{20}$ hydrocarbyl-substituted Group-13-14 metalloid radicals;
e) Q is a radical independently selected from hydride, hydrocarbyl, alkoxide, aryloxide, amide or phosphide radicals; an alkylidenyl or a cyclometallated hydrocarbyl radical; or a diene;
f) L' are Lewis basic ligands;
g) w is 0, 1, or 2;
h) X is a Group-15 atom;
i) J is a Group-15 atom when z=1 or a Group-16 atom when z=0; and
j) x is the number of $CR_2$" groups.

30. A catalyst comprising an activator and a metal complex with the formula I or II:

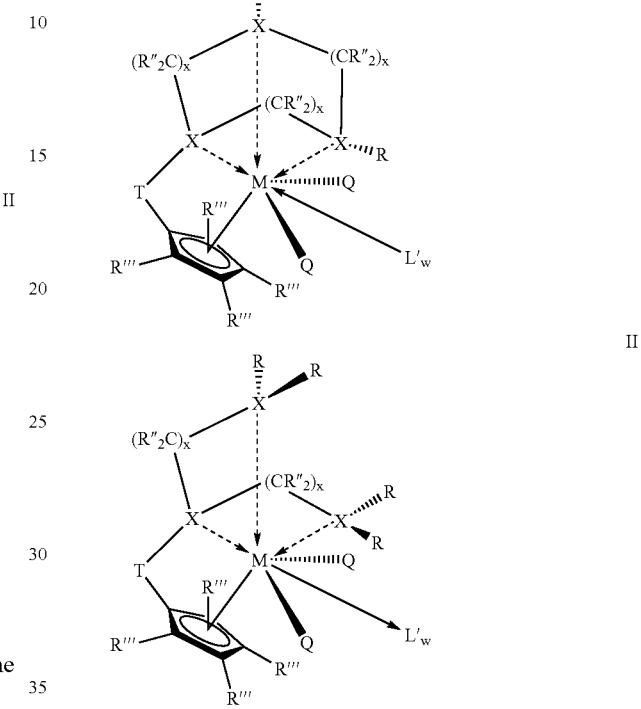

wherein
a) M is a Group-3 or lanthanide metal;
b) R, R", and R'" are independently selected from
   (i) hydrogen;
   (ii) $C_1$-$C_{20}$ hydrocarbyl radicals;
   (iii) $C_1$-$C_{20}$ substituted hydrocarbyl radicals having at least one hydrogen group wherein one of the at least one hydrogen groups is substituted by a halogen; amido; phosphido; alkoxy; or aryloxy group; and
   (iv) $C_1$-$C_{20}$ hydrocarbyl-substituted Group-13-14 metalloid radicals;
c) T is a covalent bridging group comprising at least one Group-14 or -15 atom;
d) Q is a radical independently selected from hydride, hydrocarbyl, alkoxide, aryloxide, amide or phosphide radicals; an alkylidenyl or a cyclometallated hydrocarbyl radical; or a diene;
e) X is a Group-15 metal;
f) L' are Lewis basic ligands;
g) w is 0, 1, or 2; and
h) x is the number of $CR"_2$ groups.

* * * * *